United States Patent [19]

Takeshiba et al.

[11] Patent Number: 5,134,152

[45] Date of Patent: Jul. 28, 1992

[54] OXETANE DERIVATIVES AND THEIR USE AS ANTI-FUNGAL OR FUNGICIDAL AGENTS

[75] Inventors: Hideo Takeshiba; Junzo Tobitsuka; Kazuo Sato; Hisaki Kajino; Hiroyuki Itoh; Yukiyoshi Takahi; Hiroshi Ohta, all of Shiga; Sadao Oida, Tokyo; Noriko Takeda, Tokyo; Toshiyuki Konosu, Tokyo; Hiroshi Yasuda, Tokyo, all of Japan

[73] Assignee: Sankyo Company, Limited, Tokyo, Japan

[21] Appl. No.: 621,840

[22] Filed: Dec. 4, 1990

[51] Int. Cl.$^5$ ................. A01N 43/653; A61K 31/41; C07D 249/08
[52] U.S. Cl. ................. 514/383; 548/267.8; 548/268.6; 548/268.8
[58] Field of Search ............ 514/383; 548/268.8, 548/267.8, 268.6

[56] References Cited

U.S. PATENT DOCUMENTS 4,503,063 3/1985 Richardson et al. ............... 514/383

FOREIGN PATENT DOCUMENTS 318214 5/1989 European Pat. Off. .

*Primary Examiner*—Patricia L. Morris
*Attorney, Agent, or Firm*—Frishauf, Holtz, Goodman & Woodward

[57] ABSTRACT

Compounds of formula (I):

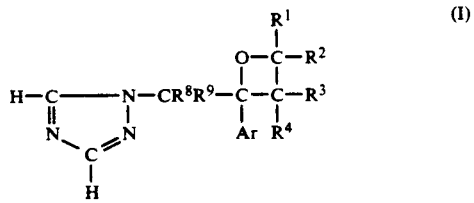

[in which: $R^1$ and $R^2$ are hydrogen or alkyl, or together are cycloalkyl; $R^3$ and $R^4$ are hydrogen, alkyl or phenyl, or together are cycloalkyl; or $R^1$ and $R^3$ together are cycloalkyl fused to the oxetane ring; Ar is phenyl substituted by $R^5$, $R^6$ and $R^7$, where $R^5$, $R^6$ and $R^7$ are hydrogen, halogen, alkyl, alkoxy, halogenated alkyl or halogenated alkoxy; and $R^8$ and $R^9$ are hydrogen or alkyl] and salts thereof have valuable agricultural and pharmaceutical anti-fungal or fungicidal activity. They may be prepared by a variety of processes.

46 Claims, No Drawings

OXETANE DERIVATIVES AND THEIR USE AS ANTI-FUNGAL OR FUNGICIDAL AGENTS

BACKGROUND TO THE INVENTION

The present invention relates to a series of new oxetane derivatives, whose molecular structure is characterized by a four-membered ring containing an oxygen atom (i.e. an oxetane ring) and which have agricultural and pharmaceutical anti-fungal or fungicidal activity. The invention also provides a process for preparing these compounds as well as methods and compositions containing them for the protection of animals, including humans, and plants from fungal attack.

Although many different types of triazole derivative having agricultural anti-fungal or fungicidal activities are already known, almost all of them lack the oxetane skeleton which is a characteristic of the compounds of the present invention.

European Patent Publication No. 106 515 discloses the use of certain 2-(triazolylmethyl)oxetan-4-one derivatives as intermediates in a process for the preparation of anti-fungal agents (which are not oxetane derivatives), but these intermediates are structurally different from the compounds of the present invention and they have not, in themselves, been found to have any anti-fungal activity.

Additionally, European Patent Publication No. 318 214 discloses the use of a limited number of 2-(triazolylmethyl)oxetane derivatives as, inter alia, anti-fungal agents, although this prior specification is mainly concerned with the corresponding tetrahydrofuranyl compounds, and the 2-(triazolylmethyl)oxetane derivatives specifically disclosed in it differ from those of the present invention in the nature of the substituent on the 4-position of the oxetane ring.

We have now discovered a series of novel triazole compounds having an oxetane skeleton, which differ structurally from known triazole derivatives, and which possess excellent pharmaceutical and agricultural anti-fungal or fungicidal activities.

BRIEF SUMMARY OF INVENTION

It is an object of the present invention to provide, as new compositions of matter, a series of novel oxetane derivatives.

It is a further object of the present invention to provide a method for preparing these compounds.

It is a still further object of the present invention to provide compositions comprising these compounds and suitable for use as either pharmaceutical or agricultural anti-fungal or fungicidal agents and to provide methods of using these compounds and compositions for pharmaceutical and agricultural purposes.

The novel oxetane derivatives of the present invention may be represented by the formula (I):

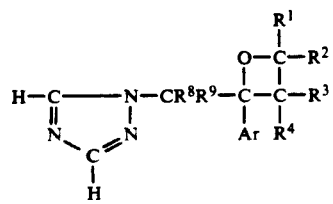

in which:

$R^1$ and $R^2$ are independently selected from the group consisting of hydrogen atoms and alkyl groups having from 1 to 6 carbon atoms, or $R^1$ and $R^2$, together with the carbon atom to which they are attached, form a cycloalkyl group having from 3 to 6 carbon atoms;

$R^3$ and $R^4$ are independently selected from the group consisting of hydrogen atoms, alkyl groups having from 1 to 6 carbon atoms and phenyl groups, or $R^3$ and $R^4$, together with the carbon atom to which they are attached, form a cycloalkyl group having from 3 to 6 carbon atoms; or $R^1$ and $R^3$ and the carbon atoms to which they attached together form a cycloalkyl group having 5 or 6 ring atoms and fused to the oxetane ring; $R^2$ is selected from the group consisting of hydrogen atoms and alkyl groups having from 1 to 6 carbon atoms; and $R^4$ is selected from the group consisting of hydrogen atoms, alkyl groups having from 1 to 6 carbon atoms and phenyl groups Ar represents a phenyl group substituted by $R^5$, $R^6$ and $R^7$, where $R^5$, $R^6$ and $R^7$ are independently selected from the group consisting of hydrogen atoms, halogen atoms, alkyl groups having from 1 to 6 carbon atoms, alkoxy groups having from 1 to 6 carbon atoms, halogenated alkyl groups having from 1 to 6 carbon atoms and halogenated alkoxy groups having from 1 to 6 carbon atoms; and $R^8$ and $R^9$ are independently selected from the group consisting of hydrogen atoms and alkyl groups having from 1 to 4 carbon atoms;

and salts thereof.

The invention also provides a pharmaceutical composition for the prevention or treatment of fungal infections, which comprises a fungicidally or fungistatically effective amount of an anti-fungal agent, wherein the anti-fungal agent is selected from the group consisting of compounds of formula (I) and pharmaceutically acceptable salts thereof, as defined above.

The invention still further provides a method for the prevention or treatment of fungal infections, which comprises applying or administering a fungicidally or fungistatically effective amount of an anti-fungal agent to an animal, e.g. a mammal, which may be human, wherein the anti-fungal agent is selected from the group consisting of compounds of formula (I) and pharmaceutically acceptable salts thereof, as defined above.

The invention also provides an agricultural composition for the protection of plants and plant reproductive matter from fungal attack, which composition comprises a fungicidally or fungistatically effective amount of a compound of formula (I) or a salt thereof, as defined above, in admixture with an agricultural carrier or diluent.

The invention still further provides a method of protecting plants and plant reproductive matter from fungal attack, which method comprises applying to said plants or plant reproductive matter or to a locus including the same a fungicidally or fungistatically effective amount of a compound of formula (I) or a salt thereof, as defined above.

The invention also provides several novel methods of preparing the compounds of the present invention, which are described in more detail hereafter.

DETAILED DESCRIPTION OF INVENTION

In the compounds of the present invention, where $R^1$, $R^2$, $R^3$, $R^4$, $R^5$, $R^6$ or $R^7$ represents an alkyl group, this may be a straight or branched chain alkyl group having from 1 to 6 carbon atoms. Examples of such groups include the methyl, ethyl, propyl, isopropyl, butyl, isobutyl, sec-butyl, t-butyl, pentyl, isopentyl, t-pentyl, neopentyl, hexyl, isohexyl, 2-methylbutyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl and 2,3-dimethylbutyl groups, of which we prefer those alkyl groups containing from 1 to 4 carbon atoms.

Where $R^1$ and $R^2$ or $R^3$ and $R^4$, together with the carbon atom to which they are attached, form a cycloalkyl group having from 3 to 6 carbon atoms, this forms a spiro double ring system with the oxetane ring. Such cycloalkyl groups include the cyclopropyl, cyclobutyl, cyclopentyl and cyclohexyl groups, of which the cyclopentyl and cyclohexyl groups are preferred and the cyclohexyl group is most preferred. Preferably only one of $R^1$ and $R^2$ or $R^3$ and $R^4$ forms such a spiro system, and more preferably this is $R^3$ and $R^4$.

Where $R^1$ and $R^3$, together with the carbon atoms to which they are attached, form a cycloalkyl group, this is a cyclopentyl or cyclohexyl group fused to the oxetane ring, and is preferably a cyclohexyl group. The remaining groups, $R^2$ and $R^4$ may be hydrogen atoms or alkyl groups, r, in the case of $R^4$, a phenyl group.

Of the groups and atoms which may be represented by $R^1$, $R^2$, $R^3$ and $R^4$, we especially prefer that they should be the same or different and each represent a hydrogen atom or an alkyl group containing from 1 to 4 carbon atoms. More preferably one of $R^1$ and $R^2$ should represent a hydrogen atom and the other should represent an alkyl group containing from 1 to 4 carbon atoms, and one of $R^3$ and $R^4$ should represent a hydrogen atom or an alkyl group containing from 1 to 4 carbon atoms and the other should represent an alkyl group containing from 1 to 4 carbon atoms. Still more preferably, one of $R^1$ and $R^2$ should represent a hydrogen atom and the other should represent a methyl or ethyl group, and one of $R^3$ and $R^4$ should represent a hydrogen atom or a methyl group and the other should represent a methyl group. Most preferably: $R^1$ and $R^4$ both represent methyl groups and $R^2$ and $R^3$ both represent hydrogen atoms; or $R^1$ represents an ethyl group, $R^4$ represents a methyl group and $R^2$ and $R^3$ both represent hydrogen atoms; or $R^1$ and $R^2$ both represent hydrogen atoms and $R^3$ and $R^4$ both represent methyl groups; or $R^1$, $R^3$ and $R^4$ all represent methyl groups and $R^2$ represents a hydrogen atom.

Ar represents a phenyl group having from 1 to 3 substituents represented by $R^5$, $R^6$ and $R^7$, i.e. it may be a substituted or unsubstituted phenyl group which has 1,2 or 3 substituents. Where there are two or three of these substituents, they may be the same or different.

Where $R^5$, $R^6$ or $R^7$ represents a halogen atom, this may be a fluorine, chlorine, bromine or iodine atom, and is preferably a fluorine atom or a chlorine atom.

Where $R^5$, $R^6$ or $R^7$ represents an alkyl group, this may be as defined above.

Where $R^5$, $R^6$ or $R^7$ represents an alkoxy group, this may be a straight or branched chain alkoxy group having from 1 to 6 carbon atoms. Examples of such groups include the methoxy, ethoxy, propoxy, isopropoxy, butoxy, isobutoxy, sec-butoxy, t-butoxy, pentyloxy, isopentyloxy, t-pentyloxy, neopentyloxy, hexyloxy, isohexyloxy, 2-methylbutoxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups. Of these, we prefer those alkoxy groups containing from 1 to 4 carbon atoms.

Where $R^5$, $R^6$ or $R^7$ represents a halogenated alkyl group, this has from 1 to 6 carbon atoms and may be a straight or branched chain alkyl group having one or more, preferably from 1 to 5 (or less if there are fewer substitutable positions), more preferably from 1 to 3, halogen substituents. Examples include any of the alkyl groups exemplified above, but more preferably those having from 1 to 4 and most preferably 1 or 2 carbon atoms, in which one or more hydrogen atoms is replaced by a halogen atom (e.g. a fluorine, chlorine, bromine or iodine atom). Specific examples include the trifluoromethyl, trichloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl and 2,2-dibromoethyl groups, of which we prefer the trifluoromethyl, trichloromethyl, difluoromethyl, 2-bromoethyl, 2-chloroethyl and 2-fluoroethyl groups, especially the trifluoromethyl group.

Where $R^5$, $R^6$ or $R^7$ represents a halogenated alkoxy group, this has from 1 to 6 carbon atoms and may be a straight or branched chain alkoxy group having one or more, preferably from 1 to 5 (or less if there are fewer substitutable positions), more preferably from 1 to 3, halogen substituents. Examples include any of the alkoxy groups exemplified above in which one or more hydrogen atoms is replaced by a halogen atom (e.g. a fluorine, chlorine, bromine or iodine atom). Specific examples include the trifluoromethoxy, trichloromethoxy, difluoromethoxy, dichloromethoxy, dibromomethoxy, fluoromethoxy, chloromethoxy, bromomethoxy, iodomethoxy, bromodifluoromethoxy, chlorodifluoromethoxy, 2,2,2-trichloroethoxy, 2,2,2-trifluoroethoxy, 2-bromoethoxy, 2-chloroethoxy, 2-fluoroethoxy and 2,2-dibromoethoxy groups, of which we prefer the trifluoromethoxy group.

Where the phenyl group of Ar has a single substituent, this is preferably in the 2- (ortho-) or 4-(para-) position, more preferably the 4-position. Where there are two such substituents, these are preferably in the 2,4- or 2,6- positions, more preferably the 2,4-position. Where there are three such substituents, these are preferably in the 2,4,5- or 2,4,6- positions, more preferably the 2,4,6-position. We prefer that there should be one or two such substituents.

Of the groups and atoms which may be represented by $R^5$, $R^6$ and $R^7$, we especially prefer that they should be independently selected from the group consisting of hydrogen atoms, halogen atoms and halogenated alkyl groups having from 1 to 4 carbon atoms, more preferably from the group consisting of hydrogen atoms and halogen atoms, in which case they are preferably hydrogen, chlorine, fluorine or bromine atoms. In one preferred class of such compounds, one of $R^5$, $R^6$ and $R^7$ represents a hydrogen atom and the two are the same or different and each represents halogen atom or a halogenated alkyl group having from 1 to 4 carbon atoms; more prefer ably, one of $R^5$, $R^6$ and $R^7$ represents a hydrogen atom and the other two are the same or different and each represents a halogen atom; still more preferably, one of $R^5$, $R^6$ and $R^7$ represents a hydrogen and the other two are the same or different and represents a chlorine, fluorine or bromine atom.

The more preferred groups represented by Ar are the o-chlorophenyl, p-chlorophenyl, p-fluorophenyl, p-bromophenyl, 2,4-difluorophenyl, 2,6-difluorophenyl, 2,4-dichlorophenyl, 2-chloro-4-fluorophenyl, 4-chloro-2-fluorophenyl, 6-chloro-2-fluorophenyl, 4-trifluoromethylphenyl and 4-trifluoromethoxyphenyl groups, of which the p-chlorophenyl, p-fluorophenyl, 2,4-difluorophenyl, 2,4-dichlorophenyl, 2-chloro-4-fluorophenyl and 4-chloro-2-fluorophenyl groups are most preferred.

Where $R^8$ or $R^9$ represents an alkyl group, this may be a straight or branched chain alkyl group having from 1 to 4 carbon atoms. Examples of such groups include the methyl, ethyl, propyl, isopropyl, butyl, isobutyl, sec-butyl and t-butyl groups, of which we prefer those alkyl groups containing 1 or 2 carbon atoms. More preferably, one of $R^8$ and $R^9$ represents a hydrogen atom and the other represents a hydrogen atom or an alkyl group having from 1 to 4 carbon atoms, and still more preferably both of $R^8$ and $R^9$ represent hydrogen atoms.

The compounds of the present invention include several basic nitrogen atoms and can, therefore, form acid addition salts. There is no particular restriction on the nature of these salts, provided that, where they are intended for therapeutic use, they are pharmaceutically acceptable and, where they are intended for agricultural use, they are agriculturally acceptable. Where they are intended for non-therapeutic or non-agricultural uses, e.g. as intermediates in the preparation of other, and possibly more active, compounds, even this restriction need not apply. Examples of such acid addition salts include: salts with a mineral acid, especially a hydrohalic acid (such as hydrochloric acid, hydrofluoric acid, hydrobromic acid or hydroiodic acid), or another mineral acid (such as sulfuric acid, nitric acid, perchloric acid or phosphoric acid); salts with an organic carboxylic acid, such as oxalic acid, maleic acid, sucoinic acid or citric acid; and salts with a sulfonio acid, e.g. an alkanesulfonic or haloalkanesulfonic acid, such as methanesulfonic acid, trifluoromethanesulfonic acid or ethanesulfonic acid, or with an arylsulfonic acid, such as benzenesulfonic acid or p-toluenesulfonic acid. The nitrates and oxalates are preferred.

The compounds of the present invention necessarily contain several asymmetric carbon atoms in their molecules, each of which can exist in the R-configuration or the S-configuration, and can thus form stereoisomers. Although these are all represented herein by a single molecular formula, the present invention includes both the individual, isolated isomers and mixtures, including racemates, thereof. Where stereospecific synthesis techniques are employed, individual isomers may be prepared directly; on the other hand, if a mixture of isomers is prepared, the individual isomers may be obtained by conventional resolution techniques.

The stereochemistry of the 4-position of the oxetane ring does not appear to affect the activity of the compounds of the present invention. However, the stereochemistry of the 3-position does seem to be significant. Where a compound has two substituents, one on the 3-position and one on the 4-position of the oxetane ring, e.g. a 3,4-dimethyloxetane compound, the preferred configuration is the (2R, 3S) configuration or the diastereomerio (2S, 3R) configuration, or a racemate (1:1 mixture) of the two diastereoisomers, which may be represented as either (2R*, 3S*) or (2S*, 3R*), more preferably the (2R, 3S, 4R) configuration or the diastereomeric (2S, 3R, 4S) configuration, or a racemate of the two diastereoisomers, which may be represented as either (2R*, 3S*, 4R*) or (2S*, 3R*, 4S*).

Examples of specific compounds of the invention are given in the following formulae (I-1), (I-2) and (I-3), in which the substituents are as defined in the corresponding one of Tables 1 to 3, respectively, i.e. Table 1 relates to formula (I-1), Table 2 relates to formula (I-2) and Table 3 relates to formula (I-3).

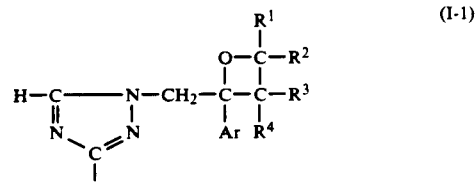

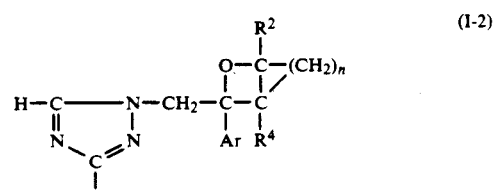

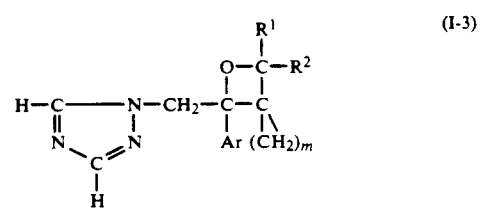

In the Tables, the following abbreviations are used:

| | |
|---|---|
| Bu | butyl |
| Et | ethyl |
| Me | methyl |
| Ph | phenyl |
| Pr | propyl |
| iPr | isopropyl |

TABLE 1

| Cpd. No. | $R^1$ | $R^2$ | $R^3$ | $R^4$ | Ar |
|---|---|---|---|---|---|
| 1-1 | H | H | H | H | 2,4-diFPh |
| 1-2 | Me | H | H | H | 2,4-diFPh |
| 1-3 | Me | Me | H | H | 2,4-diFPh |
| 1-4 | Me | Et | H | H | 2,4-diFPh |
| 1-5 | Me | Pr | H | H | 2,4-diFPh |
| 1-6 | Me | Bu | H | H | 2,4-diFPh |
| 1-7 | Me | H | Me | H | 2,4-diFPh |
| 1-8 | Me | H | Me | Me | 2,4-diFPh |
| 1-9 | Me | H | Me | Pr | 2,4-diFPh |
| 1-10 | Me | H | Me | iPr | 2,4-diFPh |
| 1-11 | Me | H | Et | H | 2,4-diFPh |
| 1-12 | Me | H | Et | Me | 2,4-diFPh |
| 1-13 | Me | H | Et | Et | 2,4-diFPh |
| 1-14 | Me | H | Et | Pr | 2,4-diFPh |
| 1-15 | Me | H | Et | iPr | 2,4-diFPh |
| 1-16 | Me | H | Pr | H | 2,4-diFPh |
| 1-17 | Me | H | Pr | Pr | 2,4-diFPh |
| 1-18 | Me | H | Pr | iPr | 2,4-diFPh |
| 1-19 | Me | H | iPr | H | 2,4-diFPh |
| 1-20 | Me | Me | Me | H | 2,4-diFPh |
| 1-21 | Me | Me | Me | Me | 2,4-diFPh |
| 1-22 | Me | Me | Me | Et | 2,4-diFPh |
| 1-23 | Me | Me | Me | Pr | 2,4-diFPh |
| 1-24 | Me | Me | Me | iPr | 2,4-diFPh |

TABLE 1-continued

| Cpd. No. | R¹ | R² | R³ | R⁴ | Ar |
|---|---|---|---|---|---|
| 1-25 | Me | Me | Et | H | 2,4-diFPh |
| 1-26 | Me | Me | Et | Et | 2,4-diFPh |
| 1-27 | Me | Me | Et | Pr | 2,4-diFPh |
| 1-28 | Me | Me | Et | iPr | 2,4-diFPh |
| 1-29 | Me | Me | Pr | H | 2,4-diFPh |
| 1-30 | Me | Me | Pr | Pr | 2,4-diFPh |
| 1-31 | Me | Me | iPr | H | 2,4-diFPh |
| 1-32 | Me | Et | Me | H | 2,4-diFPh |
| 1-33 | Me | Et | Me | Me | 2,4-diFPh |
| 1-34 | Me | Et | Me | Et | 2,4-diFPh |
| 1-35 | Me | Et | Me | Pr | 2,4-diFPh |
| 1-36 | Me | Et | Me | iPr | 2,4-diFPh |
| 1-37 | Me | Et | Et | H | 2,4-diFPh |
| 1-38 | Me | Et | Et | Me | 2,4-diFPh |
| 1-39 | Me | Et | Et | Et | 2,4-diFPh |
| 1-40 | Me | Et | Et | Pr | 2,4-diFPh |
| 1-41 | Me | Et | Et | iPr | 2,4-diFPh |
| 1-42 | Me | Et | Pr | H | 2,4-diFPh |
| 1-43 | Me | Et | Pr | Me | 2,4-diFPh |
| 1-44 | Me | Et | Pr | Et | 2,4-diFPh |
| 1-45 | Me | Et | Pr | Pr | 2,4-diFPh |
| 1-46 | Me | Et | iPr | H | 2,4-diFPh |
| 1-47 | Me | Et | iPr | Me | 2,4-diFPh |
| 1-48 | Me | Et | iPr | Et | 2,4-diFPh |
| 1-49 | Me | Pr | Me | H | 2,4-diFPh |
| 1-50 | Me | Pr | Me | Me | 2,4-diFPh |
| 1-51 | Me | Pr | Me | Et | 2,4-diFPh |
| 1-52 | Me | Pr | Me | Pr | 2,4-diFPh |
| 1-53 | Me | Pr | Me | iPr | 2,4-diFPh |
| 1-54 | Me | Pr | Et | H | 2,4-diFPh |
| 1-55 | Me | Pr | Et | Et | 2,4-diFPh |
| 1-56 | Me | Pr | Et | Pr | 2,4-diFPh |
| 1-57 | Me | Pr | Et | iPr | 2,4-diFPh |
| 1-58 | Me | Pr | Pr | H | 2,4-diFPh |
| 1-59 | Me | Pr | Pr | Pr | 2,4-diFPh |
| 1-60 | Me | Pr | iPr | H | 2,4-diFPh |
| 1-61 | Me | Bu | Me | H | 2,4-diFPh |
| 1-62 | Me | Bu | Me | Me | 2,4-diFPh |
| 1-63 | Me | Bu | Me | Et | 2,4-diFPh |
| 1-64 | Me | Bu | Me | Pr | 2,4-diFph |
| 1-65 | Me | Bu | Me | iPr | 2,4-diFPh |
| 1-66 | Me | Bu | Et | H | 2,4-diFPh |
| 1-67 | Me | Bu | Et | Et | 2,4-diFPh |
| 1-68 | Me | Bu | Et | Pr | 2,4-diFPh |
| 1-69 | Me | Bu | Et | iPr | 2,4-diFPh |
| 1-70 | Me | Bu | Pr | H | 2,4-diFPh |
| 1-71 | Me | Bu | Pr | Pr | 2,4-diFPh |
| 1-72 | Me | Bu | iPr | H | 2,4-diFPh |
| 1-73 | Et | H | H | H | 2,4-diFPh |
| 1-74 | Et | Et | H | H | 2,4-diFPh |
| 1-75 | Et | Pr | H | H | 2,4-diFPh |
| 1-76 | Et | H | Me | Me | 2,4-diFPh |
| 1-77 | Et | Et | Me | H | 2,4-diFPh |
| 1-78 | Et | Et | Me | Me | 2,4-diFPh |
| 1-79 | Et | Et | Me | Et | 2,4-diFPh |
| 1-80 | Et | Et | Me | Pr | 2,4-diFPh |
| 1-81 | Et | Et | Me | iPr | 2,4-diFPh |
| 1-82 | Et | Et | Et | H | 2,4-diFPh |
| 1-83 | Et | Et | Et | Et | 2,4-diFPh |
| 1-84 | Et | Et | Et | Pr | 2,4-diFPh |
| 1-85 | Et | Et | Et | iPr | 2,4-diFPh |
| 1-86 | Et | Et | Pr | H | 2,4-diFPh |
| 1-87 | Pr | H | Me | Me | 2,4-diFPh |
| 1-88 | Et | Et | iPr | H | 2,4-diFPh |
| 1-89 | Et | Pr | Me | H | 2,4-diFPh |
| 1-90 | iPr | H | Me | Me | 2,4-diFPh |
| 1-91 | Et | Pr | Me | Et | 2,4-diFPh |
| 1-92 | Et | Pr | Me | Pr | 2,4-diFPh |
| 1-93 | Et | Pr | Me | iPr | 2,4-diFPh |
| 1-94 | Et | Pr | Et | H | 2,4-diFPh |
| 1-95 | Et | Pr | Et | Et | 2,4-diFPh |
| 1-96 | Et | Pr | Et | Pr | 2,4-diFPh |
| 1-97 | Et | Pr | Et | iPr | 2,4-diFPh |
| 1-98 | Et | Pr | Pr | H | 2,4-diFPh |
| 1-99 | Et | Pr | Pr | Pr | 2,4-diFPh |
| 1-100 | Et | Pr | iPr | H | 2,4-diFPh |
| 1-101 | Et | Bu | Me | H | 2,4-diFPh |
| 1-102 | Et | Bu | Me | Me | 2,4-diFPh |
| 1-103 | Et | Bu | Me | Et | 2,4-diFPh |
| 1-104 | Et | Bu | Me | Pr | 2,4-diFPh |
| 1-105 | Et | Bu | Me | iPr | 2,4-diFPh |
| 1-106 | Et | Bu | Et | H | 2,4-diFPh |
| 1-107 | Et | Bu | Et | Et | 2,4-diFPh |
| 1-108 | Et | Bu | Et | Pr | 2,4-diFPh |
| 1-109 | Et | Bu | Et | iPr | 2,4-diFPh |
| 1-110 | Et | Bu | Pr | H | 2,4-diFPh |
| 1-111 | Et | Bu | Pr | Pr | 2,4-diFPh |
| 1-112 | iPr | H | Me | H | 2,4-diFPh |
| 1-113 | H | H | Me | H | 2,4-diFPh |
| 1-114 | H | H | Me | Me | 2,4-diFPh |
| 1-115 | H | H | Me | Et | 2,4-diFPh |
| 1-116 | H | H | Me | Pr | 2,4-diFPh |
| 1-117 | H | H | Me | iPr | 2,4-diFPh |
| 1-118 | H | H | Et | H | 2,4-diFPh |
| 1-119 | H | H | Et | Et | 2,4-diFPh |
| 1-120 | H | H | Et | Pr | 2,4-diFPh |
| 1-121 | H | H | Et | iPr | 2,4-diFPh |
| 1-122 | H | H | Pr | H | 2,4-diFPh |
| 1-123 | H | H | Pr | Pr | 2,4-diFPh |
| 1-124 | H | H | iPr | H | 2,4-diFPh |
| 1-125 | Et | H | Me | H | 2,4-diFPh |
| 1-126 | Et | H | Et | H | 2,4-diFPh |
| 1-127 | Et | H | Pr | H | 2,4-diFPh |
| 1-128 | Et | H | iPr | H | 2,4-diFPh |
| 1-129 | Pr | H | H | H | 2,4-diFPh |
| 1-130 | Pr | H | Me | H | 2,4-diFPh |
| 1-131 | Pr | H | Et | H | 2,4-diFPh |
| 1-132 | Pr | H | Pr | H | 2,4-diFPh |
| 1-133 | Pr | H | iPr | H | 2,4-diFPh |
| 1-134 | iPr | H | H | H | 2,4-diFPh |
| 1-135 | iPr | H | Me | H | 2,4-diFPh |
| 1-136 | iPr | H | Et | H | 2,4-diFPh |
| 1-137 | iPr | H | Pr | H | 2,4-diFPh |
| 1-138 | iPr | H | iPr | H | 2,4-diFPh |
| 1-139 | H | H | H | H | 2,4-diClPh |
| 1-140 | Me | H | H | H | 2,4-diClPh |
| 1-141 | Me | Me | H | H | 2,4-diClPh |
| 1-142 | Me | Et | H | H | 2,4-diClPh |
| 1-143 | Me | Pr | H | H | 2,4-diClPh |
| 1-144 | Me | Bu | H | H | 2,4-diClPh |
| 1-145 | Me | H | Me | H | 2,4-diClPh |
| 1-146 | Me | H | Me | Me | 2,4-diClPh |
| 1-147 | Me | H | Me | Pr | 2,4-diClPh |
| 1-148 | Me | H | Me | iPr | 2,4-diClPh |
| 1-149 | Me | H | Et | H | 2,4-diClPh |
| 1-150 | Me | H | Et | Me | 2,4-diClPh |
| 1-151 | Me | H | Et | Et | 2,4-diClPh |
| 1-152 | Me | H | Et | Pr | 2,4-diClPh |
| 1-153 | Me | H | Et | iPr | 2,4-diClPh |
| 1-154 | Me | H | Pr | H | 2,4-diClPh |
| 1-155 | Me | H | Pr | Pr | 2,4-diClPh |
| 1-156 | Me | H | iPr | H | 2,4-diClPh |
| 1-157 | Me | Me | Me | H | 2,4-diClPh |
| 1-158 | Me | Me | Me | Me | 2,4-diClPh |
| 1-159 | Me | Me | Me | Et | 2,4-diClPh |
| 1-160 | Me | Me | Me | Pr | 2,4-diClPh |
| 1-161 | Me | Me | Me | iPr | 2,4-diClPh |
| 1-162 | Me | Me | Et | H | 2,4-diClPh |
| 1-163 | Me | Me | Et | Et | 2,4-diClPh |
| 1-164 | Me | Me | Et | Pr | 2,4-diClPh |
| 1-165 | Me | Me | Et | iPr | 2,4-diClPh |
| 1-166 | Me | Me | Pr | H | 2,4-diClPh |
| 1-167 | Me | Me | Pr | Pr | 2,4-diClPh |
| 1-168 | Me | Me | iPr | H | 2,4-diClPh |
| 1-169 | Me | Et | Me | H | 2,4-diClPh |
| 1-170 | Me | Et | Me | Me | 2,4-diClPh |
| 1-171 | Me | Et | Me | Et | 2,4-diClPh |
| 1-172 | Me | Et | Me | Pr | 2,4-diClPh |
| 1-173 | Me | Et | Me | iPr | 2,4-diClPh |
| 1-174 | Me | Et | Et | H | 2,4-diClPh |
| 1-175 | Me | Et | Et | Et | 2,4-diClPh |
| 1-176 | Me | Et | Et | Pr | 2,4-diClPh |
| 1-177 | Me | Et | Et | iPr | 2,4-diClPh |
| 1-178 | Me | Et | Pr | H | 2,4-diClPh |
| 1-179 | Me | Et | Pr | Pr | 2,4-diClPh |
| 1-180 | Me | Et | iPr | H | 2,4-diClPh |
| 1-181 | Me | Pr | Me | H | 2,4-diClPh |
| 1-182 | Me | Pr | Me | Me | 2,4-diClPh |
| 1-183 | Me | Pr | Me | Et | 2,4-diClPh |
| 1-184 | Me | Pr | Me | Pr | 2,4-diClPh |

TABLE 1-continued

| Cpd. No. | R¹ | R² | R³ | R⁴ | Ar |
|---|---|---|---|---|---|
| 1-185 | Me | Pr | Me | iPr | 2,4-diClPh |
| 1-186 | Me | Pr | Et | H | 2,4-diClPh |
| 1-187 | Me | Pr | Et | Et | 2,4-diClPh |
| 1-188 | Me | Pr | Et | Pr | 2,4-diClPh |
| 1-189 | Me | Pr | Et | iPr | 2,4-diClPh |
| 1-190 | Me | Pr | Pr | H | 2,4-diClPh |
| 1-191 | Me | Pr | Pr | Pr | 2,4-diClPh |
| 1-192 | Me | Pr | iPr | H | 2,4-diClPh |
| 1-193 | Me | Bu | Me | H | 2,4-diClPh |
| 1-194 | Me | Bu | Me | Me | 2,4-diClPh |
| 1-195 | Me | Bu | Me | Et | 2,4-diClPh |
| 1-196 | Me | Bu | Me | Pr | 2,4-diClPh |
| 1-197 | Me | Bu | Me | iPr | 2,4-diClPh |
| 1-198 | Me | Bu | Et | H | 2,4-diClPh |
| 1-199 | Me | Bu | Et | Et | 2,4-diClPh |
| 1-200 | Me | Bu | Et | Pr | 2,4-diClPh |
| 1-201 | Me | Bu | Et | iPr | 2,4-diClPh |
| 1-202 | Me | Bu | Pr | H | 2,4-diClPh |
| 1-203 | Me | Bu | Pr | Pr | 2,4-diClPh |
| 1-204 | Me | Bu | iPr | H | 2,4-diClPh |
| 1-205 | Et | H | H | H | 2,4-diClPh |
| 1-206 | Et | Et | H | H | 2,4-diClPh |
| 1-207 | Et | Pr | H | H | 2,4-diClPh |
| 1-208 | Et | Bu | H | H | 2,4-diClPh |
| 1-209 | Et | Et | Me | H | 2,4-diClPh |
| 1-210 | Et | Et | Me | Me | 2,4-diClPh |
| 1-211 | Et | Et | Me | Et | 2,4-diClPh |
| 1-212 | Et | Et | Me | Pr | 2,4-diClPh |
| 1-213 | Et | Et | Me | iPr | 2,4-diClPh |
| 1-214 | Et | Et | Et | H | 2,4-diClPh |
| 1-215 | Et | H | Me | H | 2,4-diClPh |
| 1-216 | Et | Et | Et | Pr | 2,4-diClPh |
| 1-217 | Et | Et | Et | iPr | 2,4-diClPh |
| 1-218 | Et | Et | Pr | H | 2,4-diClPh |
| 1-219 | Et | Et | Pr | Pr | 2,4-diClPh |
| 1-220 | Et | Et | Pr | H | 2,4-diClPh |
| 1-221 | Et | Pr | Me | H | 2,4-diClPh |
| 1-222 | Et | Pr | Me | Me | 2,4-diClPh |
| 1-223 | Et | Pr | Me | Et | 2,4-diClPh |
| 1-224 | Et | Pr | Me | Pr | 2,4-diClPh |
| 1-225 | Et | Pr | Me | iPr | 2,4-diClPh |
| 1-226 | Et | Pr | Et | H | 2,4-diClPh |
| 1-227 | Et | Pr | Et | Et | 2,4-diClPh |
| 1-228 | Et | Pr | Et | Pr | 2,4-diClPh |
| 1-229 | Et | Pr | Et | iPr | 2,4-diClPh |
| 1-230 | Et | Pr | Pr | H | 2,4-diClPh |
| 1-231 | Et | Pr | Pr | Pr | 2,4-diClPh |
| 1-232 | Et | Pr | iPr | H | 2,4-diClPh |
| 1-233 | Et | H | Me | Me | 2,4-diClPh |
| 1-234 | Pr | H | Me | Me | 2,4-diClPh |
| 1-235 | iPr | H | Me | Me | 2,4-diClPh |
| 1-236 | Et | Bu | Me | Pr | 2,4-diClPh |
| 1-237 | Et | Bu | Me | iPr | 2,4-diClPh |
| 1-238 | Et | Bu | Et | H | 2,4-diClPh |
| 1-239 | Et | Bu | Et | Et | 2,4-diClPh |
| 1-240 | Et | Bu | Et | Pr | 2,4-diClPh |
| 1-241 | iPr | H | Me | H | 2,4-diClPh |
| 1-242 | Et | Bu | Pr | H | 2,4-diClPh |
| 1-243 | Pr | H | Me | H | 2,4-diClPh |
| 1-244 | Et | Bu | iPr | H | 2,4-diClPh |
| 1-245 | H | H | Me | H | 2,4-diClPh |
| 1-246 | H | H | Me | Me | 2,4-diClPh |
| 1-247 | H | H | Me | Et | 2,4-diClPh |
| 1-248 | H | H | Me | Pr | 2,4-diClPh |
| 1-249 | H | H | Me | iPr | 2,4-diClPh |
| 1-250 | H | H | Et | H | 2,4-diClPh |
| 1-251 | H | H | Et | Et | 2,4-diClPh |
| 1-252 | H | H | Et | Pr | 2,4-diClPh |
| 1-253 | H | H | Et | iPr | 2,4-diClPh |
| 1-254 | H | H | Pr | H | 2,4-diClPh |
| 1-255 | H | H | Pr | Pr | 2,4-diClPh |
| 1-256 | H | H | iPr | H | 2,4-diClPh |
| 1-257 | Et | H | Me | H | 2,4-diClPh |
| 1-258 | Et | H | Et | H | 2,4-diClPh |
| 1-259 | Et | H | Pr | H | 2,4-diClPh |
| 1-260 | Et | H | iPr | H | 2,4-diClPh |
| 1-261 | Pr | H | H | H | 2,4-diClPh |
| 1-262 | Pr | H | Me | H | 2,4-diClPh |
| 1-263 | Pr | H | Et | H | 2,4-diClPh |
| 1-264 | Pr | H | Pr | H | 2,4-diClPh |
| 1-265 | Pr | H | iPr | H | 2,4-diClPh |
| 1-266 | iPr | H | H | H | 2,4-diClPh |
| 1-267 | iPr | H | Me | H | 2,4-diClPh |
| 1-268 | iPr | H | Et | H | 2,4-diClPh |
| 1-269 | iPr | H | Pr | H | 2,4-diClPh |
| 1-270 | iPr | H | iPr | H | 2,4-diClPh |
| 1-271 | H | H | H | H | 2-Cl-4-FPh |
| 1-272 | Me | H | H | H | 2-Cl-4-FPh |
| 1-273 | Me | Me | H | H | 2-Cl-4-FPh |
| 1-274 | Me | Et | H | H | 2-Cl-4-FPh |
| 1-275 | Me | Pr | H | H | 2-Cl-4-FPh |
| 1-276 | Me | Bu | H | H | 2-Cl-4-FPh |
| 1-277 | Me | H | Me | H | 2-Cl-4-FPh |
| 1-278 | Me | H | Et | H | 2-Cl-4-FPh |
| 1-279 | Me | H | Pr | H | 2-Cl-4-FPh |
| 1-280 | Me | H | iPr | H | 2-Cl-4-FPh |
| 1-281 | Et | H | H | H | 2-Cl-4-FPh |
| 1-282 | Et | Et | H | H | 2-Cl-4-FPh |
| 1-283 | iPr | H | Me | H | 2-Cl-4-FPh |
| 1-284 | iPr | H | Me | Me | 2-Cl-4-FPh |
| 1-285 | H | H | Me | H | 2-Cl-4-FPh |
| 1-286 | H | H | Me | Me | 2-Cl-4-FPh |
| 1-287 | H | H | Me | Et | 2-Cl-4-FPh |
| 1-288 | Pr | H | Me | Me | 2-Cl-4-FPh |
| 1-289 | H | H | Me | iPr | 2-Cl-4-FPh |
| 1-290 | H | H | Et | H | 2-Cl-4-FPh |
| 1-291 | H | H | Et | Et | 2-Cl-4-FPh |
| 1-292 | H | H | Et | Pr | 2-Cl-4-FPh |
| 1-293 | H | H | Et | iPr | 2-Cl-4-FPh |
| 1-294 | H | H | Pr | H | 2-Cl-4-FPh |
| 1-295 | Et | H | Me | Me | 2-Cl-4-FPh |
| 1-296 | H | H | iPr | H | 2-Cl-4-FPh |
| 1-297 | Et | H | Me | H | 2-Cl-4-FPh |
| 1-298 | Et | H | Et | H | 2-Cl-4-FPh |
| 1-299 | Et | H | Pr | H | 2-Cl-4-FPh |
| 1-300 | Et | H | iPr | H | 2-Cl-4-FPh |
| 1-301 | Pr | H | H | H | 2-Cl-4-FPh |
| 1-302 | Pr | H | Me | H | 2-Cl-4-FPh |
| 1-303 | Pr | H | Et | H | 2-Cl-4-FPh |
| 1-304 | Pr | H | Pr | H | 2-Cl-4-FPh |
| 1-305 | Pr | H | iPr | H | 2-Cl-4-FPh |
| 1-306 | iPr | H | H | H | 2-Cl-4-FPh |
| 1-307 | iPr | H | Me | H | 2-Cl-4-FPh |
| 1-308 | iPr | H | Et | H | 2-Cl-4-FPh |
| 1-309 | iPr | H | Pr | H | 2-Cl-4-FPh |
| 1-310 | iPr | H | iPr | H | 2-Cl-4-FPh |
| 1-311 | H | H | H | H | 4-Cl-2-FPh |
| 1-312 | Me | H | H | H | 4-Cl-2-FPh |
| 1-313 | Me | Me | H | H | 4-Cl-2-FPh |
| 1-314 | Me | Et | H | H | 4-Cl-2-Fph |
| 1-315 | Me | Pr | H | H | 4-Cl-2-FPh |
| 1-316 | Me | Bu | H | H | 4-Cl-2-FPh |
| 1-317 | Me | H | Me | H | 4-Cl-2-FPh |
| 1-318 | Me | H | Et | H | 4-Cl-2-FPh |
| 1-319 | Me | H | Pr | H | 4-Cl-2-FPh |
| 1-320 | Me | H | iPr | H | 4-Cl-2-FPh |
| 1-321 | Et | H | H | H | 4-Cl-2-FPh |
| 1-322 | Et | Et | H | H | 4-Cl-2-FPh |
| 1-323 | Et | Pr | H | H | 4-Cl-2-FPh |
| 1-324 | Et | Bu | H | H | 4-Cl-2-FPh |
| 1-325 | H | H | Me | H | 4-Cl-2-FPh |
| 1-326 | H | H | Me | Me | 4-Cl-2-FPh |
| 1-327 | H | H | Me | Et | 4-Cl-2-FPh |
| 1-328 | H | H | Me | Pr | 4-Cl-2-FPh |
| 1-329 | H | H | Me | iPr | 4-Cl-2-FPh |
| 1-330 | H | H | Et | H | 4-Cl-2-FPh |
| 1-331 | H | H | Et | Et | 4-Cl-2-FPh |
| 1-332 | H | H | Et | Pr | 4-Cl-2-FPh |
| 1-333 | H | H | Et | iPr | 4-Cl-2-FPh |
| 1-334 | H | H | Pr | H | 4-Cl-2-FPh |
| 1-335 | H | H | Pr | Pr | 4-Cl-2-FPh |
| 1-336 | H | H | iPr | H | 4-Cl-2-FPh |
| 1-337 | Et | H | Me | H | 4-Cl-2-FPh |
| 1-338 | Et | H | Et | H | 4-Cl-2-FPh |
| 1-339 | Et | H | Pr | H | 4-Cl-2-FPh |
| 1-340 | Et | H | iPr | H | 4-Cl-2-FPh |
| 1-341 | Pr | H | H | H | 4-Cl-2-FPh |
| 1-342 | Pr | H | Me | H | 4-Cl-2-FPh |
| 1-343 | Pr | H | Et | H | 4-Cl-2-FPh |
| 1-344 | Pr | H | Pr | H | 4-Cl-2-FPh |

TABLE 1-continued

| Cpd. No. | R¹ | R² | R³ | R⁴ | Ar |
|---|---|---|---|---|---|
| 1-345 | Pr | H | iPr | H | 4-Cl-2-FPh |
| 1-346 | iPr | H | H | H | 4-Cl-2-FPh |
| 1-347 | iPr | H | Me | H | 4-Cl-2-FPh |
| 1-348 | iPr | H | Et | H | 4-Cl-2-FPh |
| 1-349 | iPr | H | Pr | H | 4-Cl-2-FPh |
| 1-350 | iPr | H | iPr | H | 4-Cl-2-FPh |
| 1-351 | H | H | H | H | 2-ClPh |
| 1-352 | Me | H | H | H | 2-ClPh |
| 1-353 | Me | Me | H | H | 2-ClPh |
| 1-354 | Me | Et | H | H | 2-ClPh |
| 1-355 | Me | H | Me | H | 2-ClPh |
| 1-356 | Me | H | Et | H | 2-ClPh |
| 1-357 | Et | H | H | H | 2-ClPh |
| 1-358 | Et | Me | H | H | 2-ClPh |
| 1-359 | Et | Et | H | H | 2-ClPh |
| 1-360 | H | H | Me | H | 2-ClPh |
| 1-361 | H | H | Me | Me | 2-ClPh |
| 1-362 | H | H | Me | Et | 2-ClPh |
| 1-363 | H | H | Et | H | 2-ClPh |
| 1-364 | H | H | Et | Et | 2-ClPh |
| 1-365 | Et | H | Me | H | 2-ClPh |
| 1-366 | Et | H | Et | H | 2-ClPh |
| 1-367 | Et | H | Pr | H | 2-ClPh |
| 1-368 | Et | H | iPr | H | 2-ClPh |
| 1-369 | Pr | H | H | H | 2-ClPh |
| 1-370 | Pr | H | Me | H | 2-ClPh |
| 1-371 | Pr | H | Et | H | 2-ClPh |
| 1-372 | Pr | H | Pr | H | 2-ClPh |
| 1-373 | Pr | H | iPr | H | 2-ClPh |
| 1-374 | iPr | H | H | H | 2-ClPh |
| 1-375 | iPr | H | Me | H | 2-ClPh |
| 1-376 | iPr | H | Et | H | 2-ClPh |
| 1-377 | iPr | H | Pr | H | 2-ClPh |
| 1-378 | iPr | H | iPr | H | 2-ClPh |
| 1-379 | H | H | H | H | 4-ClPh |
| 1-380 | Me | H | H | H | 4-ClPh |
| 1-381 | Me | Me | H | H | 4-ClPh |
| 1-382 | Me | Et | H | H | 4-ClPh |
| 1-383 | Me | H | Me | H | 4-ClPh |
| 1-384 | Me | H | Et | H | 4-ClPh |
| 1-385 | Et | H | H | H | 4-ClPh |
| 1-386 | Et | Me | H | H | 4-ClPh |
| 1-387 | Et | Et | H | H | 4-ClPh |
| 1-388 | H | H | Me | H | 4-ClPh |
| 1-389 | H | H | Me | Me | 4-ClPh |
| 1-390 | H | H | Me | Et | 4-ClPh |
| 1-391 | H | H | Et | H | 4-ClPh |
| 1-392 | H | H | Et | Et | 4-ClPh |
| 1-393 | Et | H | Me | H | 4-ClPh |
| 1-394 | Et | H | Et | H | 4-ClPh |
| 1-395 | Et | H | Pr | H | 4-ClPh |
| 1-396 | Et | H | iPr | H | 4-ClPh |
| 1-397 | Pr | H | H | H | 4-ClPh |
| 1-398 | Pr | H | Me | H | 4-ClPh |
| 1-399 | Pr | H | Et | H | 4-ClPh |
| 1-400 | Pr | H | Pr | H | 4-ClPh |
| 1-401 | Pr | H | iPr | H | 4-ClPh |
| 1-402 | iPr | H | H | H | 4-ClPh |
| 1-403 | iPr | H | Me | H | 4-ClPh |
| 1-404 | iPr | H | Et | H | 4-ClPh |
| 1-405 | iPr | H | Pr | H | 4-ClPh |
| 1-406 | iPr | H | iPr | H | 4-ClPh |
| 1-407 | H | H | H | H | 2,6-diFPh |
| 1-408 | Me | H | H | H | 2,6-diFPh |
| 1-409 | Me | H | Me | H | 2,6-diFPh |
| 1-410 | H | H | Me | H | 2,6-diFPh |
| 1-411 | H | H | Me | Me | 2,6-diFPh |
| 1-412 | Et | H | Me | H | 2,6-diFPh |
| 1-413 | Me | H | Et | H | 2,6-diFPh |
| 1-414 | Et | H | Pr | H | 2,6-diFPh |
| 1-415 | Et | H | iPr | H | 2,6-diFPh |
| 1-416 | Pr | H | H | H | 2,6-diFPh |
| 1-417 | Pr | H | Me | H | 2,6-diFPh |
| 1-418 | Pr | H | Et | H | 2,6-diFPh |
| 1-419 | Pr | H | Pr | H | 2,6-diFPh |
| 1-420 | Pr | H | iPr | H | 2,6-diFPh |
| 1-421 | iPr | H | H | H | 2,6-diFPh |
| 1-422 | iPr | H | Me | H | 2,6-diFPh |
| 1-423 | iPr | H | Et | H | 2,6-diFPh |
| 1-424 | iPr | H | Pr | H | 2,6-diFPh |
| 1-425 | iPr | H | iPr | H | 2,6-diFPh |
| 1-426 | H | H | H | H | 6-Cl-2-FPh |
| 1-427 | Me | H | H | H | 6-Cl-2-FPh |
| 1-428 | Me | H | Me | H | 6-Cl-2-FPh |
| 1-429 | H | H | Me | H | 6-Cl-2-FPh |
| 1-430 | H | H | Me | Me | 6-Cl-2-FPh |
| 1-431 | Et | H | Me | H | 6-Cl-2-FPh |
| 1-432 | Me | H | Et | H | 6-Cl-2-FPh |
| 1-433 | Et | H | Pr | H | 6-Cl-2-FPh |
| 1-434 | Et | H | iPr | H | 6-Cl-2-FPh |
| 1-435 | Pr | H | H | H | 6-Cl-2-FPh |
| 1-436 | Pr | H | Me | H | 6-Cl-2-FPh |
| 1-437 | Pr | H | Et | H | 6-Cl-2-FPh |
| 1-438 | Pr | H | Pr | H | 6-Cl-2-FPh |
| 1-439 | Pr | H | iPr | H | 6-Cl-2-FPh |
| 1-440 | iPr | H | H | H | 6-Cl-2-FPh |
| 1-441 | iPr | H | Me | H | 6-Cl-2-FPh |
| 1-442 | iPr | H | Et | H | 6-Cl-2-FPh |
| 1-443 | iPr | H | Pr | H | 6-Cl-2-FPh |
| 1-444 | iPr | H | iPr | H | 6-Cl-2-FPh |
| 1-445 | H | H | H | H | 4-TfmPh |
| 1-446 | Me | H | H | H | 4-TfmPh |
| 1-447 | Me | H | Me | H | 4-TfmPh |
| 1-448 | H | H | Me | H | 4-TfmPh |
| 1-449 | H | H | Me | Me | 4-TfmPh |
| 1-450 | Et | H | Me | H | 4-TfmPh |
| 1-451 | Me | H | Et | H | 4-TfmPh |
| 1-452 | Et | H | Pr | H | 4-TfmPh |
| 1-453 | Et | H | iPr | H | 4-TfmPh |
| 1-454 | Pr | H | H | H | 4-TfmPh |
| 1-455 | Pr | H | Me | H | 4-TfmPh |
| 1-456 | Pr | H | Et | H | 4-TfmPh |
| 1-457 | Pr | H | Pr | H | 4-TfmPh |
| 1-458 | Pr | H | iPr | H | 4-TfmPh |
| 1-459 | iPr | H | H | H | 4-TfmPh |
| 1-460 | iPr | H | Me | H | 4-TfmPh |
| 1-461 | iPr | H | Et | H | 4-TfmPh |
| 1-462 | iPr | H | Pr | H | 4-TfmPh |
| 1-463 | iPr | H | iPr | H | 4-TfmPh |
| 1-464 | H | H | H | H | 4-TfmOPh |
| 1-465 | Me | H | H | H | 4-TfmOPh |
| 1-466 | Me | H | Me | H | 4-TfmOPh |
| 1-467 | H | H | Me | H | 4-TfmOPh |
| 1-468 | H | H | Me | Me | 4-TfmOPh |
| 1-469 | Et | H | Me | H | 4-TfmOPh |
| 1-470 | Me | H | Et | H | 4-TfmOPh |
| 1-471 | Et | H | Pr | H | 4-TfmOPh |
| 1-472 | Et | H | iPr | H | 4-TfmOPh |
| 1-473 | Pr | H | H | H | 4-TfmOPh |
| 1-474 | Pr | H | Me | H | 4-TfmOPh |
| 1-475 | Pr | H | Et | H | 4-TfmOPh |
| 1-476 | Pr | H | Pr | H | 4-TfmOPh |
| 1-477 | Pr | H | iPr | H | 4-TfmOPh |
| 1-478 | iPr | H | H | H | 4-TfmOPh |
| 1-479 | iPr | H | Me | H | 4-TfmOPh |
| 1-480 | iPr | H | Et | H | 4-TfmOPh |
| 1-481 | iPr | H | Pr | H | 4-TfmOPh |
| 1-482 | iPr | H | iPr | H | 4-TfmOPh |
| 1-483 | Et | H | Me | H | 4-FPh |
| 1-484 | H | H | H | H | 4-FPh |
| 1-485 | H | H | Me | Me | 4-FPh |
| 1-486 | Me | H | Me | H | 4-FPh |
| 1-487 | Me | H | Me | Me | 4-FPh |
| 1-488 | Me | Me | Me | Me | 4-FPh |
| 1-489 | Et | H | H | H | 4-FPh |
| 1-490 | Et | H | Et | H | 4-FPh |
| 1-491 | Et | H | Pr | H | 4-FPh |
| 1-492 | Et | H | iPr | H | 4-FPh |
| 1-493 | Me | H | Me | Me | 4-ClPh |
| 1-494 | Et | H | Me | H | 4-BrPh |
| 1-495 | H | H | H | H | 4-BrPh |
| 1-496 | H | H | Me | Me | 4-BrPh |
| 1-497 | Me | H | Me | H | 4-BrPh |
| 1-498 | Me | H | Me | Me | 4-BrPh |
| 1-499 | Me | Me | Me | Me | 4-BrPh |
| 1-500 | H | H | Et | H | 4-BrPh |
| 1-501 | Et | H | Et | H | 4-BrPh |
| 1-502 | Et | H | Pr | H | 4-BrPh |
| 1-503 | Et | H | iPr | H | 4-BrPh |
| 1-504 | Et | H | Me | H | Ph |

TABLE 1-continued

| Cpd. No. | R¹ | R² | R³ | R⁴ | Ar |
| --- | --- | --- | --- | --- | --- |
| 1-505 | H | H | H | H | Ph |
| 1-506 | H | H | Me | Me | Ph |
| 1-507 | Me | H | Me | H | Ph |
| 1-508 | Me | H | Me | Me | Ph |
| 1-509 | Me | Me | Me | Me | Ph |
| 1-510 | Et | H | H | H | Ph |
| 1-511 | Et | H | Et | H | Ph |
| 1-512 | Et | H | Pr | H | Ph |
| 1-513 | Et | H | iPr | H | Ph |

TABLE 2

| Cpd. No. | R² | R⁴ | n | Ar |
| --- | --- | --- | --- | --- |
| 2-1 | H | H | 3 | 2,4-diFPh |
| 2-2 | Me | H | 3 | 2,4-diFPh |
| 2-3 | Me | Me | 3 | 2,4-diFPh |
| 2-4 | H | Me | 3 | 2,4-diFPh |
| 2-5 | H | H | 4 | 2,4-diFPh |
| 2-6 | Me | H | 4 | 2,4-diFPh |
| 2-7 | Me | Me | 4 | 2,4-diFPh |
| 2-8 | H | Me | 4 | 2,4-diFPh |
| 2-9 | H | H | 3 | 2,4-diClPh |
| 2-10 | Me | H | 3 | 2,4-diClPh |
| 2-11 | Me | Me | 3 | 2,4-diClPh |
| 2-12 | H | Me | 3 | 2,4-diClPh |
| 2-13 | H | H | 4 | 2,4-diClPh |
| 2-14 | Me | H | 4 | 2,4-diClPh |
| 2-15 | Me | Me | 4 | 2,4-diClPh |
| 2-16 | H | Me | 4 | 2,4-diClPh |
| 2-17 | H | H | 3 | 2-Cl-4-FPh |
| 2-18 | Me | H | 3 | 2-Cl-4-FPh |
| 2-19 | Me | Me | 3 | 2-Cl-4-FPh |
| 2-20 | H | Me | 3 | 2-Cl-4-FPh |
| 2-21 | H | H | 4 | 2-Cl-4-FPh |
| 2-22 | Me | H | 4 | 2-Cl-4-FPh |
| 2-23 | Me | Me | 4 | 2-Cl-4-FPh |
| 2-24 | H | Me | 4 | 2-Cl-4-FPh |
| 2-25 | H | H | 3 | 4-Cl-2-FPh |
| 2-26 | Me | H | 3 | 4-Cl-2-FPh |
| 2-27 | Me | Me | 3 | 4-Cl-2-FPh |
| 2-28 | H | Me | 3 | 4-Cl-2-FPh |
| 2-29 | H | H | 4 | 4-Cl-2-FPh |
| 2-30 | Me | H | 4 | 4-Cl-2-FPh |
| 2-31 | Me | Me | 4 | 4-Cl-2-FPh |
| 2-32 | H | Me | 4 | 4-Cl-2-FPh |
| 2-33 | H | H | 3 | 2-ClPh |
| 2-34 | Me | H | 3 | 2-ClPh |
| 2-35 | Me | Me | 3 | 2-ClPh |
| 2-36 | H | Me | 3 | 2-ClPh |
| 2-37 | H | H | 4 | 2-ClPh |
| 2-38 | Me | H | 4 | 2-ClPh |
| 2-39 | Me | Me | 4 | 2-ClPh |
| 2-40 | H | Me | 4 | 2-ClPh |
| 2-41 | H | H | 3 | 4-ClPh |
| 2-42 | Me | H | 3 | 4-ClPh |
| 2-43 | Me | Me | 3 | 4-ClPh |
| 2-44 | H | Me | 3 | 4-ClPh |
| 2-45 | H | H | 4 | 4-ClPh |
| 2-46 | Me | H | 4 | 4-ClPh |
| 2-47 | Me | Me | 4 | 4-ClPh |
| 2-48 | H | Me | 4 | 4-ClPh |
| 2-49 | H | H | 3 | Ph |
| 2-50 | Me | H | 3 | Ph |
| 2-51 | Me | Me | 3 | Ph |
| 2-52 | H | Me | 3 | Ph |
| 2-53 | H | H | 4 | Ph |
| 2-54 | Me | H | 4 | Ph |
| 2-55 | Me | Me | 4 | Ph |
| 2-56 | H | Me | 4 | Ph |

TABLE 3

| Cpd. No. | R¹ | R² | m | Ar |
| --- | --- | --- | --- | --- |
| 3-1 | H | H | 5 | 2,4-diFPh |
| 3-2 | Me | H | 5 | 2,4-diFPh |
| 3-3 | Me | Me | 5 | 2,4-diFPh |
| 3-4 | H | H | 4 | 2,4-diFPh |
| 3-5 | Me | H | 4 | 2,4-diFPh |
| 3-6 | Me | Me | 4 | 2,4-diFPh |
| 3-7 | H | H | 5 | 2,4-diClPh |
| 3-8 | Me | H | 5 | 2,4-diClPh |
| 3-9 | Me | Me | 5 | 2,4-diClPh |
| 3-10 | H | H | 4 | 2,4-diClPh |
| 3-11 | Me | H | 4 | 2,4-diClPh |
| 3-12 | Me | Me | 4 | 2,4-diClPh |
| 3-13 | H | H | 5 | 2-Cl-4-FPh |
| 3-14 | Me | H | 5 | 2-Cl-4-FPh |
| 3-15 | Me | Me | 5 | 2-Cl-4-FPh |
| 3-16 | H | H | 4 | 2-Cl-4-FPh |
| 3-17 | Me | H | 4 | 2-Cl-4-FPh |
| 3-18 | Me | Me | 4 | 2-Cl-4-FPh |
| 3-19 | H | H | 5 | 4-Cl-2-FPh |
| 3-20 | Me | H | 5 | 4-Cl-2-FPh |
| 3-21 | Me | Me | 5 | 4-Cl-2-FPh |
| 3-22 | H | H | 4 | 4-Cl-2-FPh |
| 3-23 | Me | H | 4 | 4-Cl-2-FPh |
| 3-24 | Me | Me | 4 | 4-Cl-2-FPh |
| 3-25 | H | H | 5 | 2-ClPh |
| 3-26 | Me | H | 5 | 2-ClPh |
| 3-27 | Me | Me | 5 | 2-ClPh |
| 3-28 | H | H | 4 | 2-ClPh |
| 3-29 | Me | H | 4 | 2-ClPh |
| 3-30 | Me | Me | 4 | 2-ClPh |
| 3-31 | H | H | 5 | 4-ClPh |
| 3-32 | Me | H | 5 | 4-ClPh |
| 3-33 | Me | Me | 5 | 4-ClPh |
| 3-34 | H | H | 4 | 4-ClPh |
| 3-35 | Me | H | 4 | 4-ClPh |
| 3-36 | Me | Me | 4 | 4-ClPh |
| 3-37 | H | H | 5 | Ph |
| 3-38 | Me | H | 5 | Ph |
| 3-39 | Me | Me | 5 | Ph |
| 3-40 | H | H | 4 | Ph |
| 3-41 | Me | H | 4 | Ph |
| 3-42 | Me | Me | 4 | Ph |

Of the compounds illustrated above, Compounds No. 1-7, 1-21, 1-114, 1-118, 1-145, 1-146, 1-246, 1-277, 1-317, 1-355, 1-383, 1-393, 1-409, 1-447, 1-470, 1-483, 1-486, 1-487, 1-493, 1-497 and 1-508 are preferred, and Compounds No. 1-7, 1-114, 1-145, 1-146, 1-246, 1-277, 1-317, 1-383, 1-447, 1-483 and 1-486 are more preferred.

The most preferred compounds are Compounds No.:

1-7. 2-(2,4-difluorophenyl)-3,4-dimethyl-2-[(1H-1,2,4-triazol-1-yl)methyl]oxetane, especially the (2R*,3S*,4R*)-2-(2,4-difluorophenyl)-3,4-dimethyl-2-[(1H-1,2,4-triazol-1-yl)methyl]oxetane isomer;

1-383. 2-(4-chlorophenyl)-3,4-dimethyl-2-[(1H-1,2,4-triazol-1-yl)methyl]oxetane, especially the (2R*,3S*,4R*)-2-(4-chlorophenyl)-3,4-dimethyl-2-[(1H-1,2,4-triazol-1-yl)methyl]oxetane isomer;

1-483. 4-ethyl-2-(4-fluorophenyl)-3-methyl-2-[(1H-1,2,4-triazol-1-yl)methyl]oxetane, especially the (2R*,3S*,4S*)-4-ethyl-2-(4-fluorophenyl)-3-methyl-2-[(1H-1,2,4-triazol-1-yl)methyl]oxetane isomer;

1-486. 2-(4-fluorophenyl)-3,4-dimethyl-2-[(1H-1,2,4-triazol-1-yl)methyl]oxetane, especially the (2R*,3S*,4R*)-2-(4-fluorophenyl)-3,4-dimethyl-2-[(1H-1,2,4-triazol-1-yl)methyl]oxetane isomer;

Also preferred are salts, especially the nitrates and oxalates, of the above compounds.

The compounds of the present invention can be prepared by a variety of methods, some of which may be well known in the art for the preparation of compounds of this type. For example, in general terms, the compounds may be prepared by any of the following Methods A, B, C and D, which are novel methods and themselves form part of the present invention.

Method A

In this process, a compound of formula (II):

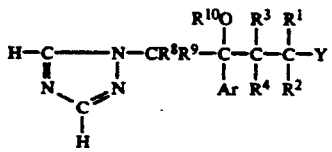

(II)

(in which:

$R^1$, $R^2$, $R^3$, $R^4$, $R^8$, $R^9$ and Ar are as defined above;

$R^{10}$ represents a hydrogen atom or a hydroxy-protecting group; and

Y represents a nucleophilic leaving group or atom)

is treated with a base, to cause cyclisation and give a compound of formula (I), which may, if desired, then be salified.

Method B

An alternative method of preparing the compounds of the present invention comprises reacting a compound of formula (III):

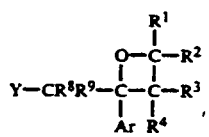

(III)

(in which $R^1$, $R^2$, $R^3$, $R^4$, $R^8$, $R^9$, Ar and Y are as defined above) with a compound of formula (IV):

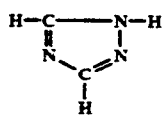

(IV)

i.e. 1H-1,2,4-triazole, in the presence of a base, to give a compound of formula (I), which may, if desired, then be salified.

Method C

A still further method of preparing the compounds of the present invention comprises reacting a compound of formula (V):

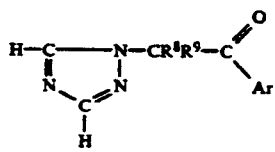

(V)

(in which $R^8$, $R^9$ and Ar are as defined above) with a compound of formula (VI):

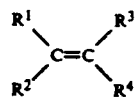

(VI)

(in which $R^1$, $R^2$, $R^3$ and $R^4$ are as defined above) or with a functional equivalent thereof, to give a compound of formula (I), which may, if desired, then be salified.

Method D

A further method comprises ring expansion of a corresponding epoxy compound of formula (VII):

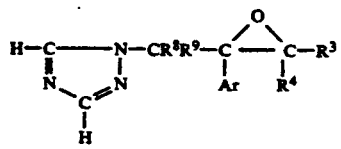

(VII)

(in which $R^3$, $R^4$, $R^8$, $R^9$ and Ar are as defined above), and then, if desired, salification of the resulting compound.

These reactions will now be described in greater detail.

Method A

In method A, a compound of formula (II) is cyclised by treatment with a base.

In the compound of formula (II), the hydroxy-protecting group represented by $R^{10}$ may be any such group commonly used in reactions of this type, and, since it does not remain in the final product, its nature is not critical, and it can be chosen from the wide range of such protecting groups which are known, on the basis solely of its functionality in the reaction. Examples of such groups include:

aliphatic acyl groups, preferably: alkanoyl groups having from 1 to 25 carbon atoms, more preferably from 1 to 20 carbon atoms, and most preferably from 1 to 6 carbon atoms, (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part preferably has from 1 to 3 carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, and most preferably 6 or 10, ring carbon atoms and is a carbocyclic group, which is unsubstituted or has from 1 to 5, preferably from 1 to 3 substituents, preferably: unsubstituted groups (such as the benzoyl, α-naphthoyl and β-naphthoyl groups); halogenated arylcarbonyl groups (such as the 2-bromobenzoyl and 4-chlorobenzoyl groups);

lower alkyl-substituted arylcarbonyl groups, in which the or each alkyl substituent preferably has from 1 to 4 carbon atoms (such as the 2,4,6-trimethylbenzoyl and 4-toluoyl groups); lower alkoxy-substituted arylcarbonyl groups, in which the or each alkoxy substituent preferably has from 1 to 4 carbon atoms (such as the 4-anisoyl group); nitro-substituted arylcarbonyl group (such as the 4-nitrobenzoyl and 2-nitrobenzoyl groups); lower alkoxycarbonyl-substituted arylcarbonyl groups, in which the or each alkoxycarbonyl substituent preferably has from 2 to 5 carbon atoms [such as the 2-(methoxycarbonyl)-benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);

tri-substituted silyl groups, in which all three or two or one of the substituents are alkyl groups having from 1 to 4 carbon atoms, and none, one or two of the substituents are aryl groups, as defined above, but preferably phenyl or substituted phenyl groups, preferably: tri(lower alkyl)silyl groups (such as the trimethylsilyl, triethysilyl, isopropyldimethylsilyl, t-butyldimethylsilyl, methyldiisopropylsilyl, methyldi-t-butylsilyl and triisopropylsilyl groups); and tri(lower alkyl)silyl groups in which one or two of the alkyl groups have been replaced by aryl groups (such as the diphenylmethylsilyl, deiphenylbutylsilyl, diphenyl-t-butylsilyl, diphenylisopropylsilyl, diphenyl-t-butylsilyl, diphenylisopropylsilyl and phenyldiisopropylsilyl groups);

alkoxyalkyl groups, in which the alkoxy and alkyl parts each have from 1 to 4 carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, 1,1-dimethyl-1-methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy)methyl groups] and lower alkoxy-substituted ethyl groups (such as the 1-ethoxyethyl and 1-isopropoxyethyl groups);

other substituted ethyl groups, preferably halogenated ethyl groups (such as the 2,2,2-trichloroethyl group); and arylselenyl-substituted ethyl groups, in which the aryl part is as defined above [such as the 2-(phenylselenyl)ethyl group];

aralkyl groups, preferably alkyl groups having from 1 to 4, more preferably from 1 to 3 and most preferably 1 or 2, carbon atoms which are substituted with from 1 to 3 aryl groups, as defined and exemplified above, which may be unsubstituted (such as the benzyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, in which the alkyl and alkoxy groups may be as defined and exemplified above and the alkylenedioxy group is preferably a methylenedioxy group, [such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)-methyl and piperonyl groups);

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups); and aralkyloxycarbonyl groups, in which the aralkyl part is as defined and exemplified above, and in which the aryl ring, if substituted, preferably has one or two lower alkoxy or nitro substituents (such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups).

Of these, we prefer the aralkyl and tri(lower alkyl)silyl groups, most preferably the benzyl and trimethylsilyl groups.

Examples of nucleophilic leaving groups and atoms which may be represented by Y include:

halogen atoms, such as the chlorine, bromine and iodine atoms);

lower alkanesulfonyloxy groups in which the alkyl part has from 1 to 6, preferably from 1 to 4, carbon atoms, (such as the methanesulfonyloxy and ethanesulfonyloxy groups);

halogenated lower alkanesulfonyloxy groups in which the alkyl part has from 1 to 6, preferably from 1 to 4, carbon atoms and is substituted with at least one halogen atom and may be perhalogenated (such as the trifluoromethanesulfonyloxy and pentafluoroethanesulfonyloxy groups); and arylsulfonyloxy groups in which the aryl part is as defined and exemplified above (such as the benzenesulfonyloxy and p-toluenesulfonyloxy groups).

Of these, we prefer the lower alkanesulfonyloxy groups and the halogen atoms, and more preferably the methanesulfonyloxy group and the chlorine atom.

The reaction in this Method comprises cyclising the compound of formula (II) by treating it with a base, preferably with more than one equivalent of a base, and normally and preferably in a solvent to cause ring-closure.

Where $R^{10}$ represents a hydroxy-protecting group which can be removed under basic conditions, the reaction in this step can be carried out using a starting material of formula (II) having such a hydroxy-protecting group. Otherwise, it is necessary to use a compound free from such a group, in which case, depending on how the compound of formula (II) was prepared, it may be necessary first to remove the hydroxy-protecting group.

The reaction is normally and preferably effected in the presence of a solvent, the nature of which is not critical, provided that it has no adverse effect upon the reaction and that it can dissolve the starting material at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, including both aliphatic and aromatic halogenated hydrocarbons, such as methylene chloride, chloroform, carbon tetrachloride, the dichloroethanes, chlorobenzene and the dichlorobenzenes; ethers such as diethyl ether, diisopropyl ether, tetrahydrofuran, dioxane, dimethoxyethane and diethylene glycol dimethyl ether; alcohols such as methanol, ethanol, propanol, isopropanol, butanol, isobutanol, t-butanol, isoamyl alcohol, diethylene glycol, glycerin, octanol, cyclohexanol and ethylene glycol monomethyl ether (e.g. as sold under the trade name "Methyl Cellosolve"); nitro compounds such as nitroethane and nitrobenzene; nitriles such as acetonitrile and isobutyronitrile; amides such as formamide, dimethylformamide, dimethylacetamide, hexamethylphosphoric triamide and 1,3-dimethyl-2-imidazolidinone; and sulfoxides such as dimethyl sulfoxide and sulfolane.

There is likewise no particular limitation upon the nature of the base used for the reaction, and any base commonly used in reactions of this type may equally be used here. Examples of preferred bases include inorganic bases, such as: alkali metal carbonates (e.g. sodium carbonate or potassium carbonate); alkali metal hydrogencarbonates (e.g. sodium hydrogencarbonate or potassium hydrogencarbonate); alkali metal hydrides (e.g. lithium hydride, sodium hydride or potassium hydride); alkali metal hydroxides (e.g. sodium hydroxide, potassium hydroxide or barium hydroxide); alkali metal cyanides (e.g. sodium cyanide or potassium cyanide); alkali metal alkoxides (e.g. sodium methoxide, sodium ethoxide or potassium t-butoxide); alkali metal azides (e.g. lithium azide or sodium azide); and alkali metal mercaptides (e.g. sodium methylmercaptide or sodium ethylmercaptide). Other preferred bases include: organic bases, especially tertiary amines, such as triethylamine, tributylamine, diisopropylethylamine, N-methylmorpholine, pyridine, 4-(N,N-dimethylamino)-pyridine, N,N-dimethylaniline, N,N-diethylaniline, 1,5-diazabicyclo[4.3.0]non-5-ene, 1,4-diazabicyclo-[2.2.2]octane (DABCO) and 1,8-diazabicyolo[5.4.0]-undec-7-ene; and organic metal bases, such as butyllithium and lithium diisopropylamide.

In order to promote the reaction more effectively, it may be carried out in the presence of one or more quaternary ammonium salts, such as benzyltriethylammonium chloride or tetrabutylammonium chloride, or crown ethers, such as dibenzo-18-crown-6.

The reaction will take place over a wide range of temperatures, and the precise reaction temperature chosen is not critical to the invention. In general, we find it convenient to carry out the reaction at a temperature in the range of from −78° C. to the boiling point of the solvent employed, preferably from −20° C. to 100° C. The time required for the reaction may likewise vary widely, depending on many factors, notably the reaction temperature and the nature of the reagents or solvents employed. However, in most cases, a period of from 10 minutes to 24 hours will normally suffice.

After completion of this reaction, the desired product may be recovered from the reaction mixture by conventional means. An example of such a technique comprises: adding a water-immiscible organic solvent to the reaction mixture; washing the organic phase with water; drying the washed organic phase; and finally distilling off the organic solvent to give the desired product. If necessary, the resulting compound can be further purified by various conventional techniques, such as recrystallization, reprecipitation or the various chromatography techniques, notably column chromatography or preparative thin layer chromatography.

Method B

In this Method, a compound of formula (I) is prepared by reacting a compound of formula (III) with 1H-1,2,4-triazole, in the presence of a base.

The reaction is a substitution reaction of the same kind as the reaction in Method A, and may be carried out using the same reagents and reaction conditions. The reaction is preferably additionally carried out in the presence of an inorganic salt, especially an alkali metal halide, such as sodium iodide or lithium bromide.

Method C

In this Method, a compound of formula (I) is prepared by reacting a compound of formula (V) with an ethylenically unsaturated compound of formula (VI), preferably using a photochemical reaction, and normally and preferably in the presence of a solvent.

The reaction is preferably effected by irradiating the reaction mixture with light, whose wavelength will depend on the nature of the olefin of formula (VI) and the ketone of formula (V), but is preferably from 280 to 350 nm. It is preferred to eliminate light having a wavelength less than 280 nm, e.g. by using a suitable filter or by carrying out the reaction in a solvent which hinders transmission of light of this wavelength, for example benzene or toluene or a mixture thereof. This apart, there is no particular restriction on the nature of the solvent to be employed, provided that it has no adverse effect on the reaction or on the reagents involved. Examples of suitable solvents include: hydrocarbons, especially aromatic hydrocarbons, such as benzene, toluene or xylene; alcohols, such as methanol, ethanol or isopropanol; nitriles, such as acetonitrile or benzonitrile; ethers, such as diethyl ether or tetrahydrofuran; and lower aliphatic and cycloaliphatic hydrocarbons, such as pentane, hexane or cyclohexane. A single one of these solvents or a mixture of any two or more of them may be used.

The reaction can take place over a wide range of temperatures, and the precise reaction temperature is not critical to the invention. In general, we find it convenient to carry out the reaction at a temperature of from −20° C. to +80° C., more preferably from 10° C. to 40° C. The time required for the reaction may also vary widely, depending on many factors, notably the reaction temperature and the nature of the reagents. However, provided that the reaction is effected under the preferred conditions outlined above, a period of from 1 hour to 4 days will usually suffice.

Method D

The ring expansion reaction employed in this Method may be achieved by reacting the compound of formula (VII) with a reagent of the type known for ring expansion of compounds of this kind, for example: a Corley reagent, such as dimethylsulfoxonium methylide; or a trimethylsulfoxonium halide, such as trimethylsulfoxonium chloride or trimethylsulfoxonium iodide; or by means of a nucleophilic methylene transfer reaction, e.g. in the presence of sodium dimethyl N-(p-toluenesulfonyl)sulfoximine [J. Am. Chem. Soc., (1973), pp 4287 et seq.]. The ring exapansion reagent is preferably employed in an amount of 2 equivalents or more per equivalent of the compound of formula (VII), more preferably from 2 to 3 equivalents. The reaction is preferably effected in the presence of a base, preferably a basic alkali metal compound, for example: an alkali metal hydride, such as sodium hydride; an alkali metal hydroxide, such as sodium hydroxide or potassium hydroxide; or an alkali metal alkoxide, such as potassium t-butoxide.

There is no particular restriction on the nature of the solvent to be employed, provided that it has no adverse effect on the reaction or on the reagents involved. Examples of suitable solvents include: sulfoxides, such as dimethyl sulfoxide; and ethers, such as tetrahydrofuran.

The reaction can take place over a wide range of temperatures, and the precise reaction temperature is not critical to the invention. In general, we find it convenient to carry out the reaction at a temperature of from $-20°$ C. to $+130°$ C., more preferably of from 0.C to ambient temperature.

In any of the methods described above, where a racemate is synthesized, this may be resolved optically by any known method, for example by forming a crystalline salt with an optically active acid such as 1-camphorsulfonic acid and then separating one optically active compound from the racemate.

After completion of any of the reactions described above, the desired compound may be recovered from the reaction mixture by conventional means. An example of such a technique comprises: adding a water-immiscible organic solvent to the reaction mixture; washing the organic phase with water; drying the washed organic phase; and finally distilling off the organic solvent to give the desired product. If necessary, the resulting compound can be further purified, using conventional purification techniques, for example recrystallization, reprecipitation or the various chromatography techniques, notably column chromatography or preparative thin layer chromatography.

Preparation of Starting Materials

The starting material used in Method A, the compound of formula (II) where $R^2$ represents a hydrogen atom, that is a compound of formula (IIa), may be prepared as shown in the following Reaction Scheme A:

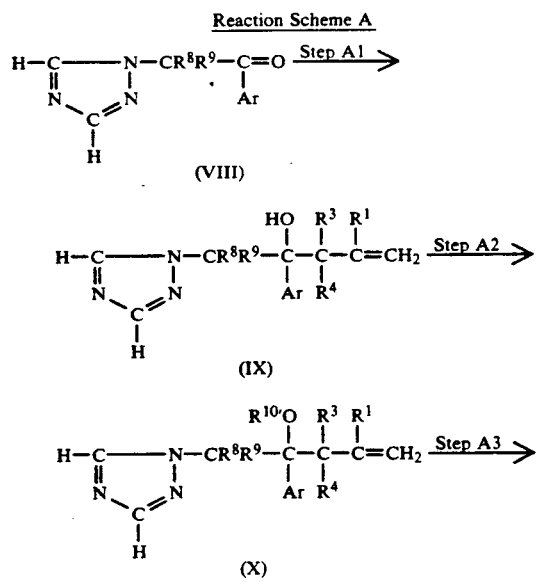

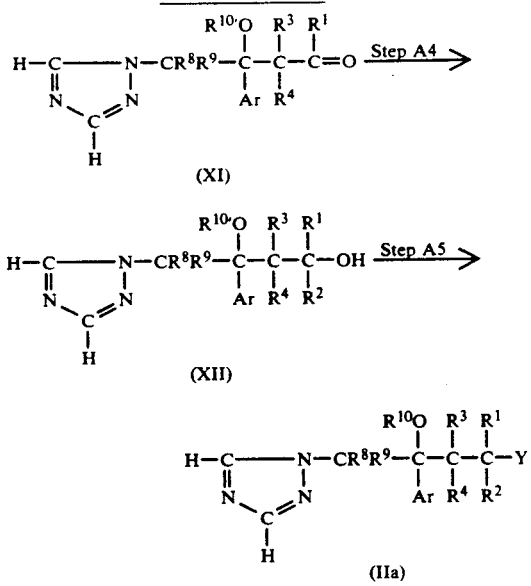

In the above formulae; $R^1$, $R^2$, $R^3$, $R^4$, $R^8$, $R^9$, $R^{10}$, Y and Ar are as defined above; and $R^{10'}$, represents a hydroxy-protecting group, which may be any of those hydroxy-protecting groups defined and exemplified above in relation to $R^{10}$.

In step A1 of this Reaction Scheme, a ketonic compound of formula (VIII) is reacted with an ethylenically unsaturated Grignard compound of formula (XIII):

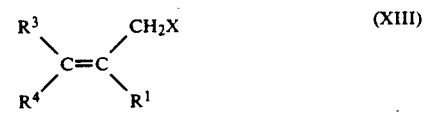

(in which $R^1$, $R^3$ and $R^4$ are as defined above and X represents —MgZ, in which Z represents a halogen atom, e.g. a chlorine, fluorine, bromine or iodine atom) to give a compound of formula (IX).

This reaction is normally and preferably effected in the presence of a solvent. There is no particular limitation upon the nature of the solvent used, provided that it has no adverse effect upon the reaction and that it can dissolve the starting material, at least to some extent. Examples of preferred solvents include ethers, such as diethyl ether, diisopropyl ether, tetrahydrofuran, dioxane, dimethoxyethane and diethylene glycol dimethyl ether.

The reaction can take place over a wide range of temperatures, and the precise reaction temperature is not critical to the invention. In general, we find it convenient to carry out the reaction at a temperature of from $-20°$ C. to $+30°$ C. The time required for the reaction may also vary widely, depending on many factors, notably the reaction temperature and the nature of the reagents and solvent used. However, provided that the reaction is effected under the preferred conditions outlined above, a period of from 30 minutes to 3 hours will usually suffice.

In some cases, the reaction may more preferably be carried out in the presence of a Lewis acid, such as zinc chloride, tin chloride, titanium chloride, boron trifluoride etherate or diethylaluminum chloride.

The starting materials used in this Step can easily be prepared according to the method described in Japanese Patent Provisional Publication No. Sho 63-46075 or Japanese Patent Publication No. Sho 63-5390, the disclosure of which is incorporated herein by reference.

In Step A2 of the Reaction Scheme, the hydroxy group in the compound of formula (IX) is protected with a suitable protecting group. There is no particular limitation on the nature of the protecting group introduced, provided that it protects the hydroxy group and prevents it from participating in the reactions of subsequent Steps. Any protecting group known for reactions of this type may equally be used here, and details of such groups and the methods employed to introduce them may be found in Green et al., "Protective Groups in Organic Synthesis", Chapter 2, published by Wiley-Interscience (1981), the disclosure of which is incorporated herein by reference.

Examples of such protecting groups have been given above, and the method chosen for the introduction of such a protecting group will, of course, depend on the nature of the group to be introduced and is well known. They may be found in "Protective Groups in Organic Synthesis", referred to above.

In Step A3, the carbonyl compound of formula (XI) is prepared by oxidative cleavage of a vinyl compound of formula (X), prepared as described in Step A2.

This reaction is normally and preferably effected in the presence of a solvent. There is no particular limitation upon the nature of the solvent employed, provided that it has no adverse effect upon the reaction and that it can dissolve the starting material at least to some extent. Examples of preferred solvents include: halogenated hydrocarbons, especially halogenated aliphatic hydrocarbons, such as methylene chloride or chloroform; esters, such as ethyl acetate or propyl acetate; ketones, such as acetone; or ethers, such as diethyl ether, tetrahydrofuran, dioxane or dimethoxyethane.

There is also no particular limitation upon the nature of the reagent used for the oxidation, provided that it can oxidatively cleave a double bond to afford a carbonyl group, and any oxidizing agent known for reactions of this type may equally be used here. The reaction may preferably be carried out by passing ozone through a solvent (such as a halogenated hydrocarbon or an ester) at a suitable temperature, for example a temperature of from $-78°$ C. to room temperature, and then treating the product with a sulfide, such as dimethyl sulfide. Alternatively, the reaction may be carried out at a suitable temperature, for example a temperature of from 0° to 50° C., using from 2 to 4 equivalents of an alkali metal salt of metaperiodic acid, such as sodium metaperiodate, in suitable solvent, for example a mixture of water and an ether or a ketone, and in the presence of a catalytic amount of an osmium oxide such as osmium tetraoxide. The time required for the reaction may vary widely, depending mainly upon the reaction temperature and upon the nature of the starting material and the solvent used, but the reaction is generally complete within a period of from 3 hours to 10 hours.

In Step A4, an alcohol of formula (XII) is prepared by reducing the carbonyl compound of formula (XI) or by using a Grignard compound.

This reduction reaction is normally and preferably effected in the presence of a solvent. There is no particular limitation upon the nature of the solvent used, provided that it has no adverse effect on the reaction and that it can dissolve the starting material at least to some extent. Examples of preferred solvents include: ethers, such as tetrahydrofuran, dioxane or dimethoxyethane; and alcohols, such as methanol, ethanol or propanol.

The reduction may be carried out according to conventional means and preferably by using conventional reducing agents such as metal hydrides, preferably alkali metal borohydrides (e.g. sodium borohydride).

The reaction can take place over a wide range of temperatures, and the precise reaction temperature is not critical to the invention. In general, we find it convenient to carry out the reaction at a temperature from $-30°$ C. to room temperature. The time required for the reaction may also vary widely, depending on many factors, notably the reaction temperature and the nature of the reagents and solvent used. However, provided that the reaction is effected under the preferred conditions outlined above, a period of from 5 minutes to 3 hours will usually suffice.

The reaction using a Grignard reagent may be conducted with, for example, a Grignard reagent of formula $R^{12}$-X, in which $R^{12}$ represents an alkyl group having from 1 to 4 carbon atoms (e.g. a methyl, ethyl, propyl, isopropyl, butyl, isobutyl, sec-butyl or t-butyl group), and X represents —MgZ, where Z represents a halogen atom. This reaction is normally and preferably effected in a solvent and may be carried out according to conventional means.

There is no particular restriction on the nature of the solvent to be employed, provided that it has no adverse effect on the reaction or on the reagents involved and that it can dissolve the reagents, at least to some extent. Examples of suitable solvents include ethers such as diethyl ether, diisopropyl ether, tetrahydrofuran, dioxane, dimethoxyethane or diethylene glycol dimethyl ether.

The reaction can take place over a wide range of temperatures, and the precise reaction temperature is not critical to the invention. In general, we find it convenient to carry out the reaction at a temperature of from $-20°$ C. to $+30°$ C. The time required for the reaction may also vary widely, depending on many factors, notably the reaction temperature and the nature of the reagents. However, provided that the reaction is effected under the preferred conditions outlined above, a period of from 30 minutes to 3 hours will usually suffice.

In Step A5, a compound of formula (IIa) is prepared by converting the free hydroxy group of the alcoholic compound of formula (XII) to a nucleophilic leaving group, Y. This reaction is normally and preferably effected in a solvent in the presence or absence of a base. At the same time, if desired, the hydroxy-protecting group, $R^{10'}$, may also be removed.

The nature of the reaction will, of course, depend upon the nature of the nucleophilic leaving group which it is desired to introduce.

For example, in the case of halogenation, the reaction may be carried out by reacting the compound of formula (XII) with a conventional halogenating agent of a type well known for halogenation reactions of this kind. Examples of preferred halogenating agents include: thionyl halides, such as thionyl chloride, thionyl bromide or thionyl iodide; sulfonyl halides, such as sulfonyl chloride or sulfonyl bromide; phosphorus trihalides, such as phosphorus trichloride or phosphorus tribromide; phosphorus pentahalides, such as phosphorus pentachloride, phosphorus pentabromide or phosphorus pentaiodide; and phosphorus oxyhalides, such as phosphorus oxychloride or phosphorus oxybromide. Of these, we prefer the phosphorus oxyhalides and thionyl halides.

In the case of sulfonylation, the reaction may be carried out by reacting the compound of formula (XII) with a compound of formula $R^{11}SO_2$—O—$SO_2R^{11}$ [wherein $R^{11}$ represents a lower alkyl group, preferably having from 1 to 4 carbon atoms (such as a methyl or ethyl group), a halogenated lower alkyl group, preferably having from 1 to 4 carbon atoms (such as a trifluoromethyl or pentafluoroethyl group) or an aryl group (such as a benzene or p-toluene group)] or with a compound of formula $R^{11}SO_2$-Y (wherein $R^{11}$ and Y are as defined above, and Y is preferably a halogen, e.g. chlorine, atom).

This reaction is normally and preferably effected in the presence of a solvent. There is no particular limitation upon the nature of the solvent used, provided that it has no adverse effect on the reaction and that it can dissolve the starting material at least to some extent. Examples of preferred solvents include: aromatic hydrocarbons, such as benzene, toluene or xylene; halogenated hydrocarbons, especially halogenated aliphatic hydrocarbons, such as methylene chloride or chloroform; esters, such as ethyl acetate or propyl acetate; ethers, such as diethyl ether, tetrahydrofuran, dioxane or dimethoxyethane; and amides, especially fatty acid amides, such as dimethylformamide, dimethylacetamide or hexamethylphosphoric triamide.

There is likewise no particular limitation upon the nature of the base used, provided that it can be used as a base in conventional reactions of this kind. Examples of preferred bases include: inorganic bases, especially basic alkali metal compounds, such as alkali metal hydrides (e.g. lithium hydride, sodium hydride or potassium hydride); organic bases, especially tertiary amines, such as triethylamine, diisopropylethylamine, N-methylmorpholine, pyridine, 4-(N,N-dimethylamino)-pyridine, N,N-dimethylaniline, 1,5-diazabicyclo[4.3.0]-non-5-ene, 1,4-diazabicyclo[2.2.2]octane, 1,8-diazabicyclo[5.4.0]undec-7-ene (DBU); and organic metal, especially alkali metal, bases, such as butyllithium or lithium diisopropylamide.

The reaction can take place over a wide range of temperatures, and the precise reaction temperature is not critical to the invention. In general, we find it convenient to carry out the reaction at a temperature of from $-20°$ C. to $50°$ C. and more preferably at from $-15°$ C. to room temperature. The time required for the reaction may also vary widely, depending on many factors, notably the reaction temperature and the nature of the reagents and solvents employed. However, provided that the reaction is effected under the preferred conditions outlined above, a period of from 5 minutes to 10 hours will usually suffice.

If desired, the hydroxy-protecting group may be removed either at this time or immediately prior to Step A5, to provide a compound of formula (IIa) in which $R^{10}$ represents a hydrogen atom.

Although the reaction conditions for deprotection of a hydroxy-protecting group will vary depending upon the nature of the protecting group, the reaction can be carried out according to methods well-known in the art, for example as follows.

Where a silyl group is used as the hydroxy-protecting group, it may generally be removed by treating the compound with a compound capable of forming a fluorine anion, such as tetrabutylammonium fluoride. This reaction is normally and preferably effected in the presence of a solvent. There is no particular limitation upon the nature of the solvent used for the reaction, provided that it has no adverse effect upon the reaction and that it can dissolve the starting material, at least to some extent. Preferred solvents include ethers, such as tetrahydrofuran or dioxane.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents. However, provided that the reaction is effected under the preferred conditions outlined above, a period of from 10 to 18 hours will usually suffice.

Where an aralkyl group or an aralkyloxycarbonyl group is employed as the hydroxy-protecting group, it can usually be removed by contacting the protected compound with a reducing agent. For example, the reaction may be carried out by subjecting the protected compound to catalytic reduction at room temperature using a catalyst such as palladium on charcoal, platinum or Raney nickel, preferably in the presence of a solvent. There is no particular limitation upon the nature of the solvent used for the reaction, provided that it has no adverse effect upon the reaction and that it can dissolve the starting material, at least to some extent. Examples of preferred solvents include: alcohols, such as methanol or ethanol; ethers, such as tetrahydrofuran or dioxane; and fatty acids, such as acetic acid; or a mixture of one or more of these organic solvents and water.

The reaction can take place over a wide range of temperatures, and the precise reaction temperature is not critical to the invention. In general, we find it convenient to carry out the reaction at a temperature of from $0°$ C. to room temperature. The time required for the reaction may also vary widely, depending on many factors, notably the reaction temperature and the nature of the reagents. However, provided that the reaction is effected under the preferred conditions outlined above, a period of from 5 minutes to 12 hours will usually suffice.

Alternatively, the aralkyl or aralkyloxycarbonyl protecting group can be removed by treating the protected compound with metallic lithium or sodium in liquid ammonia or an alcohol, such as methanol or ethanol, at a temperature of from $-78°$ C. to $-20°$ C.

Alternatively, the aralkyl or aralkyloxycarbonyl protecting group can be removed by reacting the protected compound with a combination of aluminum chloride and sodium iodide or an alkylsilyl halide such as trimethylsilyl iodide. The reaction is normally and preferably conducted in the presence of a solvent. There is no particular limitation upon the nature of the solvent used for the reaction, provided that it has no adverse effect upon the reaction and that it can dissolve the starting material, at least to some extent. Examples of preferred solvents include: nitriles, such as acetonitrile; and halogenated hydrocarbons, especially halogenated aliphatic hydrocarbons, such as methylene chloride or chloroform; and mixtures of any two or more thereof.

The reaction can take place over a wide range of temperatures, and the precise reaction temperature is not critical to the invention. In general, we find it convenient to carry out the reaction at a temperature from 0° C. to 50° C.

In this process, where the substrate, the compound of formula (XII), contains one or more sulfur atoms, a preferred reagent is a combination of aluminum chloride and sodium iodide.

Where the hydroxy-protecting group is an aliphatic acyl group, an aromatic acyl group or an alkoxycarbonyl group, it can be removed by treating the protected compound with a base in the presence of a solvent. There is no particular limitation upon the nature of the base used, provided that other parts of the compound are not affected when the protecting group is removed. Examples of preferred bases include: metal alcoholates, such as sodium methoxide; aqueous ammonia; alkali metal carbonates, such as sodium carbonate or potassium carbonate; alkali metal hydroxides, such as sodium hydroxide or potassium hydroxide; or a mixture of concentrated aqueous ammonia and methanol. There is no particular limitation upon the nature of the solvent used, and any solvent conventionally used for normal hydrolysis reactions may equally be used here. Examples of preferred solvents include: water; organic solvents, such as alcohols (e.g. methanol, ethanol or propanol) and ethers (e.g. tetrahydrofuran or dioxane); or a mixture of any two or more of these solvents, especially a mixture of water and one or more organic solvents.

The reaction can take place over a wide range of temperatures, and the precise reaction temperature is not critical to the invention. In general, in order to control side reactions, we find it convenient to carry out the reaction at a temperature from 0° C. to 150° C. The time required for the reaction may also vary widely, depending on many factors, notably the reaction temperature and the nature of the reagents, solvent and base used. However, provided that the reaction is effected under the preferred conditions outlined above, a period of from 1 to 10 hours will usually suffice.

Where the hydroxy-protecting group is an alkoxymethyl group or a substituted ethyl group, it may usually be removed by treating the protected compound with an acid, preferably in the presence of a solvent. Suitable acids used are preferably hydrochloric acid, a mixture of acetic acid and sulfuric acid, p-toluenesulfonic acid or acetic acid; alternatively, a strongly acidic cation exchange resin such as Dowex (trade mark) 50 may also be used. There is no particular limitation upon the nature of the solvent used, provided that it has no adverse effect upon the reaction and that it can dissolve the starting material at least to some extent. Preferred solvents are: alcohols, such as methanol or ethanol; ethers, such as tetrahydrofuran or dioxane; mixtures of any two or more thereof; and mixtures of any one or more thereof with water.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and acid employed. However, provided that the reaction is effected under the preferred conditions outlined above, a period of from 10 minutes to 18 hours will usually suffice.

Where the hydroxy-protecting group is an alkenyloxycarbonyl group, it may usually be removed by treating the protected compound with a base under similar reaction conditions to those employed when the hydroxy-protecting group is an aliphatic acyl group, an aromatic acyl group or an alkoxycarbonyl group.

Further, where the hydroxy-protecting group is an allyloxycarbonyl group, the deprotection reaction may simply be carried out using a combination of palladium and triphenylphosphine or nickel tetracarbonyl, which has the advantage that it minimizes side reactions.

After completion of each the reactions described above, the desired compounds may be recovered from the reaction mixture according to conventional means. One example of such a technique comprises: adding a water-immiscible organic solvent to the reaction mixture; washing the organic phase with water; drying the washed organic phase; and finally distilling off the organic solvent to give the desired product. If necessary, the resulting compounds can be further purified by well known techniques, for example, by recrystallization, reprecipitation, or the various chromatography techniques, notably preparative thin layer chromatography or column chromatography.

An alternative method of preparing a compound of formula (IIa) is illustrated by the following Reaction Scheme B:

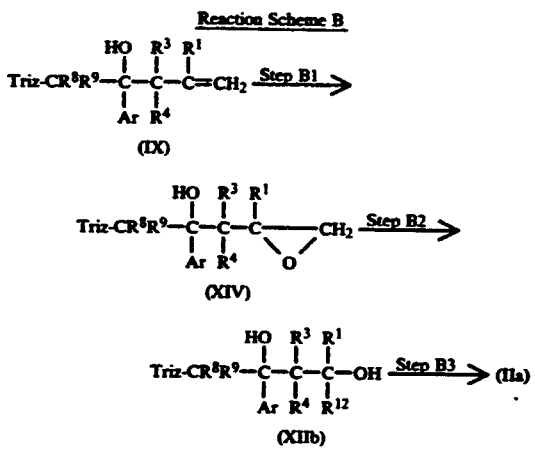

In the above formulae, $R^1R^3$, $R^4$, $R^8$, $R^9$, $R^{12}$ and Ar are as defined above, and "Triz" stands for the 1H-1,2,4,-triazol-1-yl group, which has the formula:

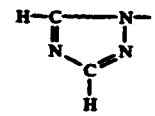

In Step B1 of this Reaction Scheme, the compound of formula (IX), which may have been prepared as described in Step A1 of Reaction Scheme A, is epoxidized to give the compound of formula (XIV).

This reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include halogenated hydrocarbons, especially halogenated aliphatic hydrocarbons, such as methylene chloride or chloroform.

There is likewise no particular restriction upon the nature of the epoxidizing agent used in this reaction and any such agent known for use in reactions of this type, i.e. the oxidation of a double bond to an epoxy group, may equally be used here. Preferred reagents are organic peroxides, especially organic peracids, such as peracetic acid or 3-chloroperbenzoic acid, or salts thereof, such as magnesium perphthalate. The amount of epoxidizing agent used is also not critical, although, for the maximum possible reaction, an equimolar or greater amount of epoxidizing agent is preferably used in relation to the amount of the compound of formula (IX). More preferably from 1 to 2 equivalents of epoxidizing agent is used per mole of the starting material of formula (IX).

The reaction can take place over a wide range of temperatures, and the precise reaction temperature is not critical to the invention. In general, we find it convenient to carry out the reaction at a temperature of from 0° C. to 50° C., more preferably at about room temperature. The time required for the reaction may also vary widely, depending on many factors, notably the reaction temperature and the nature of the starting material, epoxidizing agent and solvent used. However, provided that the reaction is effected under the preferred conditions outlined above, a period of from 30 minutes to 3 days will usually suffice.

In Step B2, an alcohol compound of formula (XIIb) is prepared by the ring-opening reaction of the epoxy compound of formula (XIV) by reduction or by using a Grignard reagent.

This reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include ethers such as diethyl ether, tetrahydrofuran, dioxane or dimethoxyethane.

Reduction may be carried out according to conventional means, but preferably using a reducing agent such as a metal hydride, especially an alkali metal hydride, e.g. lithium aluminum hydride.

The reaction can take place over a wide range of temperatures, and the precise reaction temperature is not critical to the invention. In general, we find it convenient to carry out the reaction at a temperature of from −30° C. to 50° C. The time required for the reaction may also vary widely, depending on many factors, notably the reaction temperature and the nature of the reagents and solvents used. However, provided that the reaction is effected under the preferred conditions outlined above, a period of from 30 minutes to 3 hours will usually suffice.

The ring-opening reaction using a Grignard reagent may be conducted as described in relation to the Grignard reaction which may be used in Step A4, employing the same reagents and reaction conditions.

The resulting compound of formula (XIIb) is the compound of formula (XII), prepared as described in Reaction Scheme A, but in which the group represented by $R^{10'}$ is replaced by a hydrogen atom. In Step B3, this is converted to the compound of formula (IIa). The reaction involved is exactly the same as that in Step A5 (Reaction Scheme A) and may be carried out using the same reagents and reaction conditions.

Alternatively, a compound of formula (XIIb) in which $R^{12}$ represents a hydrogen atom, that is to say a compound of formula (XIIc), may be prepared from the compound of formula (XV), see Reaction Scheme A, as shown in the following Reaction Scheme C:

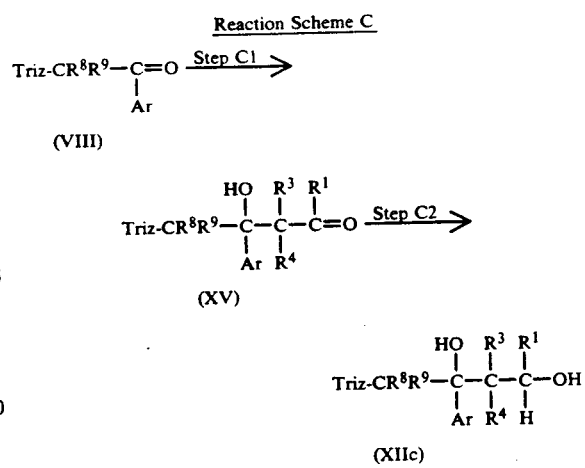

In the above Reaction Scheme, $R^1$, $R^3$, $R^4$, $R^8$, $R^9$, Ar and "Triz" are as defined above.

In Step C1 of this Reaction Scheme, a compound of formula (VIII), see Reaction Scheme A, is subjected to an aldol condensation to give the compound of formula (XV), which is then, in Step C2, subjected to reduction, to give the compound of formula (XIIc).

The aldol condensation used in Step C1 is fully described in ACS Symposium Series, No. 355 (1987), Chapter 27, page 316, the disclosure of which is incorporated herein by reference.

Step C2 involves the preparation of an alcohol compound of formula (XIIc) by subjecting a carbonyl compound of formula (XV) to reduction. This reaction is normally and preferably effected in a solvent. The reaction is essentially the same as the reduction reaction described in relation to Step A4, and may be carried out employing the same reagents and reaction conditions as described there.

A compound of formula (XIIc) in which $R^1$ represents a hydrogen atom, i.e. a compound of formula (XIId), may also be prepared as shown in the following Reaction Scheme D:

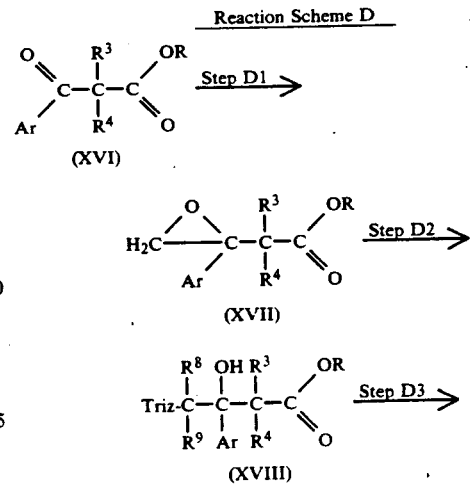

-continued
Reaction Scheme D

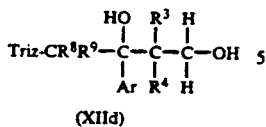

(XIId)

In the above Reaction Scheme, $R^1$, $R^3$, $R^4$, $R^8$, $R^9$, Ar and "Triz" are as defined above; and R represents an alkyl group having from 1 to 4 carbon atoms.

This series of reactions is known and is described, for example, in Japanese Patent Publication Kokai (i.e. as laid open to public inspection) No. 9864/90, the disclosure of which is incorporated herein by reference.

The compound of formula (VIII), which is the starting material in Reaction Scheme A, and thus in the other Reaction Schemes above, may be prepared as shown in Reaction Scheme E:

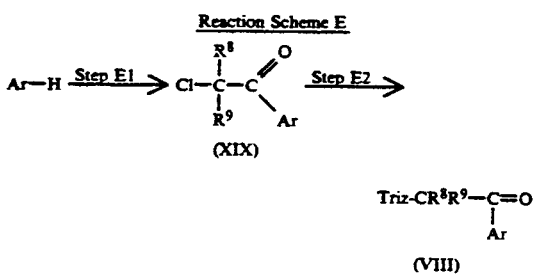

In the above Reaction Scheme, $R^8$, $R^9$ and Ar are as defined above.

Step E1 of this reaction may be effected by conventional means, as described in "Friedel Crafts and Related Reactions", Vol. 3, John Wiley (1964), the disclosure of which is incorporated herein by reference. Step E2 of this reaction may likewise be effected by conventional means, as described in Japanese Patent Application Kokai No. 82376/1984, the disclosure of which is incorporated herein by reference.

The compound of formula (III) in which $R^8$ and $R^9$ both represent hydrogen atoms, that is a compound of formula (IIIa), used as the starting material in Method B, can be prepared as shown in the following Reaction Scheme F:

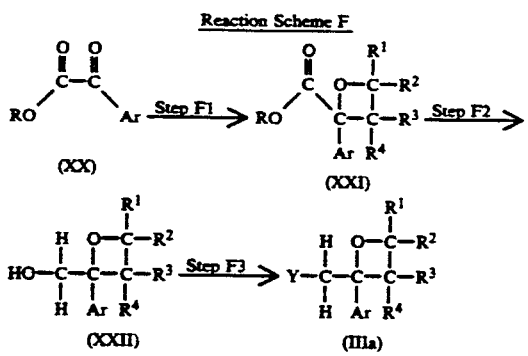

In the above Reaction Scheme, $R^1$, $R^2$, $R^3$, $R^4$, R and Ar are as defined above.

In Step F1 of the above Reaction Scheme, the gloxylic acid derivative of formula (XX) is subjected to a photochemical reaction with a compound of formula (VI):

in which $R^1$, $R^2$, $R^3$ and $R^4$ are as defined above.

This reaction may be carried out using the techniques and reaction conditions described in Helv. Chim. Acta., 72, 1792, (1989), the disclosure of which is incorporated herein by reference, or as disclosed above in relation to Method C.

In Step F2 of this Reaction Scheme, the ester of formula (XXI) produced in the first step is reduced to give the compound of formula (XXII). Any conventional method of reducing an ester to give a hydroxymethyl group may be employed. For example, one suitable method comprises reacting the compound of formula (XXI) in a suitable solvent with a reducing agent. There is no particular restriction on the nature of the solvent to be employed, provided that it has no adverse effect on the reaction or on the reagents involved and that it can dissolve the reagents, at least to some extent. Examples of suitable solvents include ethers, such as tetrahydrofuran or diethylene glycol dimethyl ether. The reaction can take place over a wide range of temperatures, and the precise reaction temperature is not critical to the invention. In general, we find it convenient to carry out the reaction at a temperature of from 0° C. to 100° C., more preferably from 10° C. to 60° C. The time required for the reaction may also vary widely, depending on many factors, notably the reaction temperature and the nature of the reagents. However, provided that the reaction is effected under the preferred conditions outlined above, a period of from 10 minutes to 5 hours will usually suffice.

There is no particular restriction on the nature of the reducing agent employed in this reaction, and any reducing agent commonly used for the reduction of esters to hydroxymethyl groups may equally be used here. Examples of suitable reducing agents include: metal hydrides, preferably alkali metal borohydrides (e.g. sodium borohydride); or lithium aluminum hydride.

Especially when the reaction is effected using a borohydride as the reducing agent, it is preferred to carry out the reaction in the presence of an alkali metal salt, for example lithium bromide.

In Step F3 of this Reaction Scheme, the hydroxymethyl compound of formula (XXII) produced in the second step is reacted with an agent to convert the hydroxy group to a nucleophilic leaving group, Y. The reaction employed will, therefore, depend on the nature of the group Y to be introduced.

For example, when the group Y is an alkanesulfonyl or aranesulfonyl group or a halogen atom, it may be carried out by any conventional sulfonylation or halogenation reaction, preferably in the presence of a base and of an inert solvent.

There is no particular restriction on the nature of the solvent to be employed, provided that it has no adverse effect on the reaction or on the reagents involved. Examples of suitable solvents include: hydrocarbons, especially aromatic hydrocarbons, such as benzene or toluene; ethers, such as tetrahydrofuran and dioxane; ketones, such as acetone and methyl ethyl ketone; alcohols, such as methanol, ethanol and t-butanol; amides, such as N,N-dimethylformamide, N,N-dimethylacetamide and N-methyl-2-pyrrolidone; and sulfoxides, such as dimethyl sulfoxide. Of these, we prefer the ketones and the amides.

There is likewise no particular restriction on the nature of the base to be employed, and any base commonly used in reactions of this type may equally be employed here, provided that it has no adverse effect on any other part of the molecule. Examples of such bases include: alkali metal hydrides, such as lithium hydride and sodium hydride; alkali metal alkoxides, such as sodium methoxide, sodium ethoxide and potassium t-butoxide; alkali metal carbonates, such as sodium carbonate and potassium carbonate; and alkali metal bicarbonates, such as sodium bicarbonate and potassium bicarbonate. Of these, we prefer the alkali metal hydrides and the alkali metal carbonates.

The reaction can take place over a wide range of temperatures, and the precise reaction temperature is not critical to the invention. In general, we find it convenient to carry out the reaction at a temperature from 0° to 120° C. (more preferably from 20° to 80° C.). The time required for the reaction may also vary widely, depending on many factors, notably the reaction temperature and the nature of the reagents. However, provided that the reaction is effected under the preferred conditions outlined above, a period of from 1 to 24 hours will usually suffice.

A compound of formula (III) in which $R^8$ and $R^9$ may represent either hydrogen atoms or carbon atoms having from 1 to 4 carbon atoms and Y represents a chlorine atom, that is to say a compound of formula (IIIb), may be prepared as shown in Reaction Scheme G:

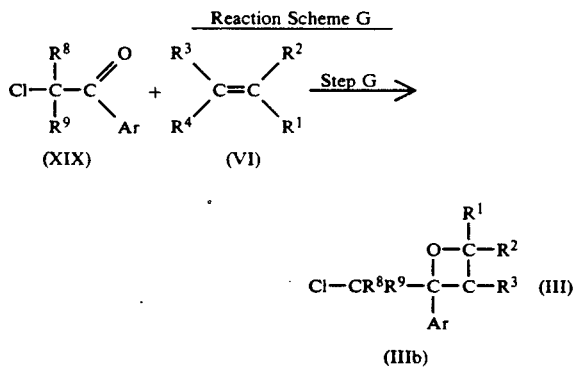

This reaction may be effected by conventional means, for example as disclosed by T. Sato & K. Tamura in Tetrahedron Letters, Vol. 25, pages 1821-1824 (1984). The compound of formula (XIX), which is the starting material, may be prepared as shown in Step E1 of Reaction Scheme E.

A compound of formula (XII) (see Reaction Scheme A), in which $R^{10'}$ represents a hydrogen atom and $R^2$ represents a methyl group, that is to say a compound of formula (XIIe), may also be prepared as shown below in Reaction Scheme H.

Reaction Scheme H

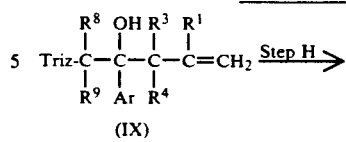

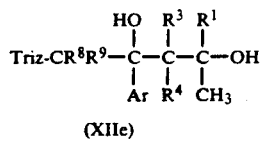

In the above formulae, $R^1$, $R^3$, $R^4$, $R^8$, $R^9$, Ar and "Triz" are as defined above.

In this Reaction Scheme, a compound of formula (IX) (see Reaction Scheme A) is subjected to hydroboration to afford the compound of formula (XIIe). The reaction is normally and preferably effected in the presence of a solvent.

There is no particular restriction on the nature of the solvent to be employed, provided that it has no adverse effect on the reaction or on the reagents involved and that it can dissolve the reagents, at least to some extent. Examples of suitable solvents include ethers, such as diethyl ether, tetrahydrofuran, dioxane or dimethoxyethane.

The hydroboration reaction comprises reacting the ethylenically unsaturated compound of formula (IX) with a borane reagent such as diborane ($B_2H_6$), boranedimethyl sulfide complex [$BH_3 \cdot S(CH_3)_2$] or 9-borabicyclo[3.3.1]nonane (9-BBN), and then treating the product with hydrogen peroxide in an alkaline medium, after which the boron is eliminated oxidatively.

The reaction can take place over a wide range of temperatures, and the precise reaction temperature is not critical to the invention. In general, we find it convenient to carry out the reaction at a temperature of from $-20°$ C. to 80° C., more preferably from room temperature to 50° C. The time required for the reaction may also vary widely, depending on many factors, notably the reaction temperature and the nature of the reagents. However, provided that the reaction is effected under the preferred conditions outlined above, a period of from 15 minutes to 5 hours will usually suffice.

The starting material of Method C is the same as the compound of formula (VIII), prepared as described in Reaction Scheme E.

The starting material used in Method D, the compound of formula (VII) is known per se, e.g. from Japanese Patent Application Kokai No. 176 266/1984, the disclosure of which is incorporated herein by reference.

After completion of each of the reactions described above, the desired compounds may be recovered from the reaction mixture by conventional means. An example of such a technique comprises: adding a water-immiscible organic solvent to the reaction mixture; washing the organic phase with water; drying the washed organic phase; and finally distilling off the organic solvent to give the desired product. If necessary, the resulting compounds can be further purified, by conventional purification techniques, for example by recrystallization, reprecipitation or the various chromatography techniques, notably column chromatography or preparative thin layer chromatography.

The compounds of the present invention have a variety of valuable biological activities, as shown by the following Experiments, which make them useful as both agricultural and pharmaceutical anti-fungal agents.

EXPERIMENT 1

Curative activity against rice blast

Rice seedlings (variety "Sachikaze") at the 4-5 leaf stage were inoculated with the fungus *Pyricularia oryzae* by spraying them with a spore suspension of the fungus and maintaining the seedlings in a moist chamber (relative humidity: 100%) at 20°-22° C. After 24 hours, the rice seedlings were sprayed with an aqueous suspension of the test compound at a concentration of 10 ppm in an amount of 30 ml per 3 pots. The rice seedlings were then kept in the moist chamber for a further 6 days. As a control, some plants were exposed to the fungus, but were not treated with any anti-fungal agent.

The activity index was determined on the basis of the number of lesions formed on the upper two leaves of each plant. The results are shown in Table 4. In this and subsequent Tables, the compounds of the present invention are identified by the number of one of the following Examples in which their preparation is described.

TABLE 4

| Example No. | Index | Salt | Isomer |
|---|---|---|---|
| 1 | 4 | | |
| 1 | 5 | Oxalate | |
| 2 | 4 | | |
| 6 | 5 | | |
| 9 | 3 | | |
| 10 | 3 | Nitrate | Isomer B |
| 16 | 5 | Nitrate | Isomer B |
| 18 | 5 | | |
| 19 | 3 | | |
| 20 | 3 | | |
| 24 | 3 | | |
| 25 | 4 | | |
| 33 | 4 | | |
| 39 | 3 | | |
| 48 | 4 | | |
| 49 | 5 | | |
| 72 | 3 | | |
| 73 + 74* | 4 | | |

*A 1:1 by weight mixture of the products of Examples 73 and 74.

The activity index was assigned on the basis of the degree of disease, which was determined by examination with the naked eye and is given by the following codes (the same applies to subsequent Experiments):

| 5: | no disease |
| 4: | disease rate was 10% or less of that of the untreated plant |
| 3: | disease rate was 10%-30% of that of the untreated plant |
| 2: | disease rate was 30%-50% of that of the untreated plant |
| 1: | disease rate was 50%-70% of that of the untreated plant |
| 0: | disease rate was 70% or more of the untreated plant and almost the same as that of the untreated plant |

EXPERIMENT 2

Preventive activity against sheath blight of rice plants

Rice seedlings (variety Nihonbare) at the 4-5 leaf stage were sprayed with an aqueous suspension of the test compound at a concentration of 100 ppm (30 ml/3 pots. The seedlings were then kept for 24 hours at room temperature, after which they were inoculated with *Rhizoctonia solani* by placing 4-5 oat grains on which the fungus had previously been cultured around the base of each seedling. The seedlings were then kept in a moist chamber (relative humidity: 100%) for 5 days at 25°-27° C. The activity index was given on the basis of the height of the lesions formed on the rice seedlings. The results are shown in Table 5.

TABLE 5

| Example No. | Index | Salt | Isomer |
|---|---|---|---|
| 1 | 5 | | |
| 1 | 3 | Oxalate | |
| 1 | 5 | Nitrate | |
| 2 | 5 | | |
| 5 | 5 | | |
| 9 | 3 | | |
| 15 | 4 | | |
| 16 | 4 | Nitrate | Isomer A |
| 16 | 5 | Nitrate | Isomer B |
| 20 | 5 | | |
| 24 | 3 | | |
| 28 | 5 | | |
| 33 | 5 | | |
| 34 | 5 | | |
| 39 | 5 | | |
| 42 | 5 | | |
| 43 | 5 | | |
| 44 | 5 | | |
| 48 | 3 | | |
| 49 | 5 | | |
| 63 | 3 | | |
| 64 | 5 | | |
| 65 | 5 | | |
| 70 | 5 | | |

EXPERIMENT 3

Curative activity against sheath blight of rice plants

Rice seedlings (variety Nohonbare) at the 4-5 leaf stage were inoculated with *Rhizoctonia solani* by placing 4-5 oat grains on which the fungus had previously been cultured around the base of each rice seedling and keeping them in a moist chamber (relative humidity: 100%) at 25°-27° C. After 24 hours, the rice seedlings were sprayed with an aqueous suspension of the test compound at a concentration of 10 ppm (30 ml/3 pots) and continued to be kept in the moist chamber for a further 5 days. The activity index was given on the basis of the height of the lesions formed on the rice seedlings. The results are shown in Table 6.

TABLE 6

| Example No. | Index | Salt | Isomer |
|---|---|---|---|
| 1 | 5 | | |
| 1 | 5 | Oxalate | |
| 1 | 5 | Nitrate | |
| 2 | 5 | | |
| 3 | 4 | | |
| 4 | 5 | | |
| 5 | 5 | | |
| 6 | 5 | | |
| 8 | 5 | | |
| 9 | 5 | | |
| 10 | 5 | | |
| 11 | 5 | | |
| 13 | 5 | | |
| 14 | 4 | | |
| 15 | 4 | | |
| 16 | 5 | Nitrate | Isomer B |
| 18 | 5 | | |
| 19 | 4 | | |
| 20 | 5 | | |
| 21 | 5 | | |
| 24 | 5 | | |

TABLE 6-continued

| Example No. | Index | Salt | Isomer |
|---|---|---|---|
| 25 | 5 | | |
| 33 | 4 | | |
| 34 | 5 | | |
| 35 | 5 | | |
| 37 | 4 | | |
| 38 | 4 | | Isomer A |
| 38 | 5 | | Isomer B |
| 39 | 5 | | |
| 40 | 4 | | |
| 41 | 4 | | |
| 42 | 5 | | |
| 43 | 5 | | |
| 44 | 5 | | |
| 46 | 5 | | |
| 47 | 4 | | |
| 48 | 5 | | |
| 49 | 5 | | |
| 61 | 5 | | |
| 62 | 5 | | |
| 63 | 5 | | |
| 64 | 4 | | |
| 65 | 5 | | |
| 68 | 5 | | |
| 69 | 5 | | |
| 72 | 5 | | |

EXPERIMENT 4

Preventive activity against sheath blight of rice plants by submerged application Rice seedlings (variety Nihonbare) at the 3–4 leaf stage grown in pots were flooded to a depth of 1 cm with water. The test compound was then applied to the water in the pots in an amount corresponding to 100 g per 10 acres. After the seedling had been kept in a green-house for 7 days, they were inoculated with *Rhizoctonia solani* by placing 4–5 oat grains on which the fungus had previously been cultured around the base of each seedling. The seedlings were then kept in a moist chamber (relative humidity:100%) for 5 days at 25°–27° C. The activity index was given on the basis of the height of the lesions formed on the rice seedlings.

The results are shown in Table 7.

TABLE 7

| Example No. | Index | Salt | Isomer |
|---|---|---|---|
| 1 | 5 | | |
| 1 | 5 | Oxalate | |
| 1 | 5 | Nitrate | |
| 2 | 5 | | |
| 3 | 4 | | |
| 4 | 4 | | |
| 5 | 4 | | |
| 6 | 4 | | |
| 8 | 4 | | |
| 9 | 5 | | |
| 10 | 5 | | |
| 12 | 5 | | |
| 13 | 3 | | |
| 14 | 3 | | |
| 16 | 3 | Nitrate | Isomer B |
| 17 | 4 | | |
| 18 | 5 | | |
| 19 | 5 | | |
| 20 | 4 | | |
| 21 | 3 | | |
| 24 | 4 | | |
| 25 | 4 | | |
| 31 | 4 | | |
| 34 | 5 | | |
| 35 | 4 | | |
| 39 | 4 | | |
| 42 | 5 | | |
| 43 | 5 | | |

TABLE 7-continued

| Example No. | Index | Salt | Isomer |
|---|---|---|---|
| 44 | 4 | | |
| 46 | 3 | | |
| 48 | 4 | | |
| 49 | 4 | | |
| 61 | 5 | | |
| 62 | 3 | | |
| 63 | 3 | | |
| 65 | 3 | | |
| 66 | 3 | | |
| 68 | 3 | | |
| 69 | 4 | | |
| 70 | 4 | | |
| 72 | 3 | | |
| 73 + 74 | 3 | | |

EXPERIMENT 5

Activity against bakanae disease of rice plants by seed soaking

Ten grams of rice seeds (variety Tanginbozu), which had been infected with the fungus *Gibberella fujikuroi* by spraying them with a spore suspension of the fungus, were immersed in 20 ml of an aqueous suspension of the test compound at a concentration of 100 ppm for 3 day. At the end of this time, the treated seeds were densely sown in soil in pots, and the pots were places in a greenhouse at 20°–30° C. for 3 weeks. The activity index was given on the basis of the number of diseased seedlings.

The results are shown in Table 8.

TABLE 8

| Example No. | Index | Salt | Isomer |
|---|---|---|---|
| 1 | 4 | | |
| 1 | 4 | Oxalate | |
| 1 | 4 | Nitrate | |
| 2 | 4 | | |
| 3 | 3 | | |
| 4 | 4 | | |
| 6 | 4 | | |
| 9 | 4 | | |
| 10 | 4 | | |
| 13 | 3 | | |
| 14 | 3 | | |
| 15 | 4 | | |
| 16 | 5 | Nitrate | Isomer A |
| 16 | 4 | Nitrate | Isomer B |
| 18 | 4 | | |
| 19 | 4 | | |
| 28 | 5 | | |

EXPERIMENT 6

Curative activity against leaf rust of wheat

Wheat seedlings (variety Norin No. 61) at the 1.5 leaf stage were inoculated with the fungus *Puccinia recondita* by sprinkling the spores of the fungus onto the seedlings. They were then kept in a moist chamber (relative humidity: 100%) for 24 hours at 20°–22° C., after which they were moved to a green-house at 15°–20° C. After 2 days, the seedlings were sprayed with an aqueous suspension of the test compound at a concentration of 3 ppm (30 ml/3 pots). The seedlings were then continuously kept in the green-house for 10 days. The activity index was given on the basis of diseased area on the first leaf at the end of this time.

The results are shown in Table 9.

TABLE 9

| Example No. | Index | Isomer |
|---|---|---|
| 3 | 5 | |
| 6 | 4 | |
| 9 | 4 | |
| 15 | 4 | |
| 16 | 4 | Isomer A |
| 16 | 4 | Isomer B |
| 28 | 4 | |
| 32 | 3 | |
| 42 | 3 | |
| 47 | 3 | |
| 64 | 3 | |
| 70 | 4 | |

EXPERIMENT 7

Curative activity against powdery mildew of barley

Barley seedlings (variety Sekishinriki) at the first leaf stage were inoculated with conidia of *Erysiphe graminis* f. sp. hordei by sprinkling spores of the fungus on the seedlings, which were then kept in a green-house at 15°–20° C. After one day, the seedlings were sprayed with an aqueous suspension of the test compound at a concentration 3 ppm (30 ml/3 pots), and they continued to be kept in the green-house at that temperature for a further 10 days. The activity index was given on the basis of the diseased area on the first leaf at the end of that time.

The results are shown in Table 10.

TABLE 10

| Example No. | Index | Salt | Isomer |
|---|---|---|---|
| 1 | 5 | | |
| 1 | 5 | Oxalate | |
| 1 | 5 | Nitrate | |
| 2 | 5 | | |
| 3 | 5 | | |
| 5 | 5 | | |
| 6 | 5 | | |
| 9 | 5 | | |
| 10 | 5 | | |
| 11 | 4 | | |
| 13 | 4 | | |
| 14 | 3 | | |
| 16 | 5 | Nitrate | Isomer A |
| 16 | 5 | Nitrate | Isomer B |
| 17 | 5 | | |
| 18 | 5 | | |
| 19 | 5 | | |
| 20 | 5 | | |
| 21 | 4 | | |
| 28 | 4 | | |
| 29 | 3 | | |
| 30 | 3 | | |
| 31 | 3 | | |
| 32 | 5 | | |
| 36 | 3 | | |
| 37 | 3 | | |
| 39 | 3 | | |
| 40 | 3 | | |
| 41 | 3 | | |
| 42 | 5 | | |
| 47 | 4 | | |
| 49 | 4 | | |
| 57 | 3 | | |
| 61 | 5 | | |
| 62 | 5 | | |
| 63 | 5 | | |
| 64 | 5 | | |
| 65 | 4 | | |
| 66 | 4 | | |
| 68 | 5 | | |
| 69 | 5 | | |
| 70 | 5 | | |
| 72 | 3 | | |

TABLE 10-continued

| Example No. | Index | Salt | Isomer |
|---|---|---|---|
| 73 + 74 | 5 | | |

Experiment 8

Preventive activity against powdery mildew of cucumber

Cucumber seedlings (variety Sagamihanpaku) at the 3–4 leaf stage were sprayed with an aqueous suspension of the test compound at a concentration of 300 ppm (30 ml/3 pots). The seedlings were then kept for 24 hours at room temperature, after which they were inoculated with conidia of *Sphaerotheca fuliginea* by sprinkling the seedlings with spores of the fungus. After the seedlings had been kept in a green-house at 20°–30° C. for 7 days, the activity index was evaluated on the basis of the diseased area on the third and fourth leaves.

The results are shown in Table 11.

TABLE 11

| Example No. | Index | Salt | Isomer |
|---|---|---|---|
| 1 | 5 | Oxalate | |
| 1 | 5 | Nitrate | |
| 2 | 5 | | |
| 3 | 5 | | |
| 6 | 5 | | |
| 8 | 5 | | |
| 9 | 5 | | |
| 10 | 5 | | |
| 15 | 5 | | |
| 16 | 4 | Nitrate | Isomer A |
| 16 | 5 | Nitrate | Isomer B |
| 21 | 5 | | |
| 22 | 5 | | |
| 24 | 5 | | |
| 25 | 5 | | |
| 28 | 5 | | |
| 29 | 5 | | |
| 34 | 5 | | |
| 39 | 5 | | |
| 41 | 5 | | |
| 42 | 5 | | |
| 43 | 5 | | |
| 44 | 5 | | |
| 46 | 5 | | |
| 47 | 5 | | |
| 49 | 5 | | |
| 51 | 5 | | |
| 55 | 5 | | |
| 57 | 5 | | |
| 59 | 5 | | |
| 63 | 5 | | |
| 64 | 5 | | |
| 65 | 5 | | |
| 66 | 5 | | |
| 70 | 5 | | |

EXPERIMENT 9

Preventive activity against apple scab

Apple seedlings at the 3–4 leaf stage were sprayed with an aqueous suspension of the test compound at a concentration of 300 ppm (30 ml/3 pots). The seedlings were then kept for 24 hours at room temperature, after which they were inoculated with the fungus *Venturia inaequalis* by spraying a spore suspension of the fungus over the seedlings. After inoculation, the seedlings were kept in a moist chamber (relative humidity: 100%) for 3 days at 20°–22° C. and then moved to a green-house at 20°–22° C. for 10 days. The activity index was given on the basis of the diseased area on the third and fourth leaves at this time.

The results are shown in Table 12.

TABLE 12

| Example No. | Index | Salt | Isomer |
|---|---|---|---|
| 1 | 5 | Oxalate | |
| 1 | 5 | Nitrate | |
| 8 | 5 | | |
| 9 | 5 | | |
| 10 | 5 | | |
| 15 | 5 | | |
| 16 | 5 | Nitrate | Isomer A |
| 16 | 5 | Nitrate | Isomer B |
| 21 | 5 | | |
| 24 | 5 | | |
| 25 | 5 | | |
| 28 | 5 | | |
| 34 | 5 | | |
| 42 | 5 | | |
| 43 | 5 | | |
| 44 | 5 | | |
| 47 | 3 | | |
| 51 | 5 | | |
| 57 | 5 | | |
| 63 | 5 | | |
| 64 | 5 | | |
| 65 | 5 | | |
| 70 | 5 | | |

EXPERIMENT 10

Antifungal Activity

A fungal disc of about 4 mm diameter was inoculated on an agar medium (2% by weight malt extract, 1% glucose, 0.3% peptone and 2%agar) in a petri dish of diameter 9 cm, by placing the disc on the center of the medium. Paper disc specimens were prepared by impregnating 30 μl of an acetone solution containing 300 ppm of the test compound into the disc (diameter 8 mm, thickness 0.7 mm) and then subjecting it to dry sterilization. The disc specimens were placed in a circle at about 1 cm distance from the fringe of the grown fungus, three days after the innoculation. The specimens were then maintained at 25° C. for 5 days, after which the antifungal activity was determined by visual observation of infection of the specimens by the fungus. The fungi tested were:

*Aspergillus niger,*
*Gliocladium virens,* and
*Fusarium moliniforme.*

The antifungal activity is indicated by the following ratings:

+: no growth of fungus on the specimens observed
−: growth of fungus on the specimens observed.

The results are shown in the following Table 13.

TABLE 13

| Compound of Example | A. niger | G. virens | F. moniliforme |
|---|---|---|---|
| 5 | − | + | + |
| 9 | − | + | + |
| 10 | − | + | + |
| 16 | − | + | + |
| 21 | + | + | + |
| 24 | + | + | + |
| 25 | + | + | + |
| 28 | − | + | + |
| 29 | + | − | + |
| 32 | − | + | + |
| 43 | + | − | − |
| 46 | + | + | + |
| 47 | + | + | + |
| 48 | − | + | + |

TABLE 13-continued

| Compound of Example | A. niger | G. virens | F. moniliforme |
|---|---|---|---|
| 49 | + | − | + |
| Control (None) | − | − | − |

EXPERIMENT 11

Wood-preservative Activity

The procedure described in Experiment 10 was repeated, except that the fungi tested were *Coriolus versicolor* and *Tyromyces palustris,* which are prescribed in JIS A-9302. The results are shown in the following Table 14.

TABLE 14

| Compound of Example | C. versicolor | T. palustris |
|---|---|---|
| 1 | + | + |
| 1 (nitrate) | + | + |
| 2 | + | + |
| 9 | + | + |
| 10 | + | + |
| 14 | + | + |
| 16 (nitrate, isomer B) | + | + |
| 32 | + | + |
| 42 | + | + |
| 43 | + | + |
| 48 | + | + |
| Control (None) | − | − |

The compounds of formula (I) and salts thereof are useful as fungicides and fungistatic agents for agricultural, horticultural and similar uses. For such uses, they may be formulated in conventional preparations for such use and may be applied to plants, parts of plants, reproductive matter from plants, or to the locus or environment containing such plants, parts of plants or reproductive matter from plants as is well known for conventional fungicides and other agrochemicals.

In particular, they have been found to be highly efficacious anti-fungal agents without damaging the plants to which they are applied.

Thus, for example, sheath blight, an important disease affecting rice crops, can be prevented by using the compound in the form of a spray or by submerged application. When the compounds are used for treating soil or seeds, they exhibit particular efficacy in preventing damping-off of crops such as beet, cotton or cucumber arising from infection by Rhizoctonia and soil infectious diseases, such as southern blight of eggplants or cucumbers etc., or black scurf of potatoes.

In the amounts used in practice, crops such as rice, tomatoes, potatoes, cotton, eggplants, cucumbers or kidney beans are not damaged by the compounds of the present invention.

Furthermore, the compounds can also be applied to orchards, non-farm areas, forests and the like.

Reflecting the activity of the compounds of the present invention, the invention further provides compositions which contain one or more of the compounds of the invention, together with a carrier and optionally other auxiliary agents, if necessary. These compositions may be formulated as preparations of the type commonly employed for agricultural or horticultural use, for instance as dusts, coarse dusts, microgranules, fine microgranules, wettable powders, emulsifiable concentrates, aqueous or oily suspensions, and aerosols. It is, of course, not necessary to use a completely pure form of the compound of the invention in the composition and, of course, purification can be suspended at any stage and the resulting crude substance may be used as the active ingredient of the composition.

The carrier employed in such compositions may be natural or synthetic and organic or inorganic; it is generally employed to assist the active ingredient to reach the substrate to be treated, and to make it easier to store, transport or handle the active compound. It may be solid, liquid or gaseous.

Suitable solid carriers include:

inorganic substances, such as clays (examples of which are bentonite, kaolinite, montmorillonite and attapulgite), talc, mica, agalmatolite, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as nut shells (e.g. of walnuts or other nuts), soybean meal, tobacco powder, walnut powder, wheat flour, wood meal, starch and crystalline cellulose; synthetic or natural high molecular weight polymers, especially resins, such as cumarone resins, petroleum resins, alkyd resins, polyvinyl chloride, polyalkylene glycols, ketone resins, ester gums, xanthan gum, copal gum and dammar gum; waxes such as carnauba wax and beeswax; or urea.

Examples of suitable liquid carriers include:

paraffinic or naphthenic hydrocarbons, such as kerosene, mineral oil, spindle oil and white oil; aromatic hydrocarbons, such as benzene, toluene, xylene, solvent naphtha, ethylbenzene, cumene and methylnaphthalene; halogenated hydrocarbons, especially chlorinated hydrocarbons, such as carbon tetrachloride, chloroform, trichloroethylene, monochlorobenzene and o-chlorotoluene; ethers such as dioxane and tetrahydrofuran; ketones, such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, ethanol, isopropanol, hexanol, ethylene glycol, diethylene glycol, cyclohexanol, and benzyl alcohol; ether alcohols, such as ethylene glycol monoethyl ether, ethylene glycol monophenyl ether, diethylene glycol monoethyl ether and diethylene glycol monobutyl ether; other polar solvents, such as dimethylformamide and dimethyl sulfoxide; and water.

Suitable gaseous carriers include:

air, nitrogen, carbon dioxide and fluorocarbon propellants such as those sold under the Trade Mark "Freon"; they may be mixed in a known manner to give a propellant.

The compositions of the invention may contain one or more surface active agents and/or polymers to improve the properties of the compositions and help them to disperse, emulsify, spread, penetrate and bind or to control disintegration, improve fluidity or impart corrosion resistance to the composition, or to stabilize the active compound. Any of the conventional classes of surface active agent (non-ionic, anionic, cationic or amphoteric) may be employed, but it is preferred to employ non-ionic and/or anionic surface active agents whereby wetting, adhesion and absorption and desired effects may be improved.

Examples of suitable non-ionic surface active agents include:

the polymerization adducts of ethylene oxide with higher alcohols, such as lauryl alcohol, stearyl alcohol and oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di- alkylphosphoric acids, such as stearylphosphoric acid or dilaurylphosphoric acid; the polymerization adducts of ethylene oxide with amines, such as dodecylamine; amides or ethoxylated amides of higher fatty acids, such as stearamide; higher fatty acid esters of polyhydric alcohols, such as sorbitan, and the polymerization adducts of ethylene oxide therewith; higher fatty acid esters of glycerol borates or of ethoxylated glycerol borates; glycerides and sucrose esters of fatty acids; and the polymerization adducts of ethylene oxide with propylene oxide.

Examples of suitable anionic surface active agents include:

salts of higher fatty acids, i.e. soaps, e.g. sodium oleate; salts, e.g. sodium and calcium salts, of sulfonic acids and the acids themselves, e.g. ligninsulfonic acid, and aryl sulfonate salts, such as sodium isopropylnaphthalenesulfonate, sodium methylenebisnaphthalenesulfonate, sodium ligninsulfonate or sodium dodecylbenzenesulfonate, or alkyl sulfonate salts, especially sodium dialkyl sulfosuccinates, such as sodium dioctyl sulfosuccinate or sodium 2-ethylhexenesulfonate; salts, e.g. sodium, ammonium and amine salts, of polyoxyethylene alkyl aryl ether sulfates or of polyoxyethylene alkyl ether sulfates or the free acids; or salts of polyoxyethylene alkyl aryl ether phosphates or of polyoxyethylene alkyl phosphates; alkyl sulfate salts, such as sodium lauryl sulfate or oleyl sulfate amine salt;

Examples of suitable cationic surfactants include: the higher aliphatic amines and ethylene oxide condensates with such amines; quaternary ammonium salts, e.g. chlorides; N-alkylamine acetates; and N-alkylamine oxides;

Examples of amphoteric surfactants include betaines and amino acid-type surfactants.

Moreover, the compositions of the present invention may be used in combination with high molecular weight compounds or other formulation agents, for example: protective colloids, such as casein, gelatin, gum arabic, albumin, glue, sodium alginate, carboxymethylcellulose, methylcellulose, hydroxyethylcellulose or polyvinyl alcohol; dispersing agents, such as sodium polyphosphate; inorganic dispersing agents, such as bentonite or veegum; stabilizers; binding agents; and anti-freezing agents. For wider applicability and labor saving, the composition of the invention can, if desired, be combined with one or more other agrochemicals, e.g. fungicides, insecticides, herbicides, plant growth regulators and fertilizers.

The above-mentioned carriers and various auxiliary agents may be used alone or in any desired combination, depending upon the type of preparation, the application and other factors. Similar factors will also be of importance in determining the concentration of the active compound in the formulation.

For example, dusts may conveniently contain from 0.1 to 25% by weight of the active compound, the remainder being a solid carrier.

Wettable powders may conveniently contain, for example, from 1 to 90%, preferably from 25 to 80%, by weight of the compound, the remainder being a solid carrier and a dispersing and wetting agent, if required, together with a protective colloidal agent, a thixotropic agent and an anti-foaming agent.

Granules may conveniently contain from 1 to 35% by weight of the active compound, a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the active compound and from 5 to 20% by weight of an emulsifying agent, the remainder being a liquid carrier, together with, if required, a corrosion inhibitor.

Oil preparations may conveniently contain from 0.5 to 5% by weight of the active compound, the remainder being a liquid carrier such as kerosene.

Aerosols may conveniently contain from 0.1 to 5% by weight of the active compound and optionally a perfume, the remainder being an oily and/or aqueous carrier, and a propellant such as liquified petroleum gas, a fluorocarbon or carbon dioxide.

The compositions of the invention may be applied, for example, to paddy or other fields before or after emergence of disease in plants or to plants already infected with harmful fungi; a concentration of from 10 to 500 ppm for the active ingredient is usually suitable, especially for application to leaves and stems of plants and to soil, whereby effective control may be attained.

The composition of the invention may conveniently be blended with other fungicide for a broader fungicidal spectrum and, in some case, a synergistic effect may be expected. Suitable other fungicides include:

carbamate-type fungicides;
such as 3,3,'-ethylenebis(tetrahydro-4,6-dimethyl-2H-1,3,5-thiadiazine-2-thione, zinc or manganese ethylenebisdithiocarbamate, bis(dimethyldithiocarbamoyl)disulfide, zinc propylenebisdithiocarbamate, methyl 1-(butyloarbamoyl)-2-benzimidazoloarbamate, 1,2-bis(3-methoxycarbonyl-2-thioureido)benzene and bisdimethyldithiocarbamoyl zinc ethylenebisdithioearbamate;

dicarboximide-type fungicides;
such as N-trichloromethylthio-4-cyclohexene-1,2-dicarboximide and N-tetrachloroethylthio-4-cyclohexene-1,2-dicarboximide;

oxazine-type fungicides;
such as 5,6-dihydro-2-methyl-1,4-oxazine-3-carboxanilide-4,4-dioxide;

naphthoquinone-type fungioides;
such as 2,3-dichloro-1,4-naphthoquinone;

and other fungicides;
such as 3-hydroxy-5-methylisoxazole, 5-ethoxy-3-trichloromethyl-1,2,4-thiadiazole, 2,4-dichloro-6-(o-chloroanilino)-1,3,5-triazine, 2,3-dicyano-1,4-dithioanthraquinone, copper 8-quinolate, polyoxin, validamycin, tetrachloroisophthalonitrile, 2-(1-methylpropyl)-4,6-dinitrophenol β,β-dimethylacrylate, triphenyltin hydroxide, phytomycin, dinitromethylheptylphenyl crotonate, 5-butyl-2-dimethylamino-6-methylpyrimidin-4-ol, 6-(3,5-dichloro-4-methylphenyl)-3-(2H)pyridazinone, 6-(3-bromophenyl)-3-(2H)-pyridazinone, N-(2,6-dimethylphenyl)-N-methoxyacetylalanine methyl ester and bis(8-guanidinooctyl)amine acetate.

The composition of the invention may be blended with insecticides. Suitable insecticides include:

phosphorus-containing insecticides;
such as O,O-diethyl 0-(2-isopropyl-4-methyl-6-pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)-phosphorodithioate, O,O-dimethyl S-[2-(ethylthio)ethyl]phosphorodithioate, O,O-dimethyl-1-hydroxy-2,2,2-trichloroethylphosphonate, O,O-diethyl-O-(5-phenyl-3-isoxazolyl)phosphorothioate, O,O-dimethyl-O-(3-methyl-4-methylmercaptophenyl)thio-phosphate, O-ethyl-O-p-cyanophenyl phenylphosphonothioate, O,O-dimethyl S-(1,2-dicarboethoxyethyl)-phosphorodithioate, 2-chloro-1-(2,4,5-trichlorophenyl)-vinyldimethyl phosphate, 2-chloro-1-(2,4-dichlorophenyl)vinyldimethyl phosphate, O,O-dimethyl O-p-cyanophenyl phosphorothioate, 2,2-dichlorovinyldimethylphosphate, ethyl mercaptophenylaoetate O,O-dimethyl phosphorodithioate, S-[(6-chloro-2-oxo-3-benzooxazolinyl)methyl]-O,O-diethylphosphorodithioate, 4-methylthiophenyl dipropylphosphate, 2-chloro-1-(2,4-dichlorophenyl)vinyldiethylphosphate, O,O-diethyl O-(3-oxo-2-phenyl-2H-pyridazin-6-yl)phosphorothioate, O,O-dimethyl S-(1-methyl-2-ethylsulfinyl)ethyl phosphorothioate, O,O-dimethyl S-phthalimidomethyl phosphorodithioate, dimethylmethylcarbamoylethylthioethyl thiophosphorothioate, O,O-diethyl S-(N-ethoxycarbonyl-N-methylcarbamoylmethyl)phosphorodithioate, O,O-dimethyl-S-[2-methoxy-1,3,4-thiadiazol-5(4H)-onyl-(4)-methyl]dithiophosphate, 2-methoxy-4H-1,3,2-benzodioxaphosphorin 2-sulfide, O,O-diethyl-O-(3,5,6-trichloro-2-pyridyl)phosphorothioate, O,S-dimethyl-N-acetyl phosphoroamidothioate, O-2,4-dichlorophenyl O-ethyl S-propylphosphorodithioate, O,O-diethyl S-(2-chloro-1-phthalimidoethyl)phosphorodithioate and O-6-ethoxy-2-ethylpyrimidin-4-yl O,O-dimethylphosphorothioate;

carbamate-type insecticides;
such as 1-naphthyl N-methylcarbamate, S-methyl-N-[methylcarbamoyloxy]thioacetoimidate, 2-sec-butylphenyl-N-methylcarbamate, 2-isopropoxyphenyl-N-methylcarbamate, 1,3-bis(carbamoylthio)-2-(N,N-dimethylamino)-propane hydrochloride and 2-dimethylamino-5,6-dimethylpyrimidin-4-yl dimethylcarbamate;

and other insecticides;
such as nicotine sulfate, milbemycin D, 6-methyl-2,3-quinoxalinedithiocyclic S,S-dithiocarbonate, 2,4-dinitro-6-sec-butylphenyldimethylacrylate, 1,1-bis-(p-chlorophenyl)-2,2,2-trichloroethanol, azoxybenzene, di(p-chlorophenyl)cyclopropyl, carbinol, isopropyl 4,4'-dichlorobenzilate, ethyl 4,4'-dichlorobenzilate, ethyl O-benzoyl-3-chloro-2,6-dimethoxybenzohydroxymate, isopropyl 4,4,'-dibromobenzilate, tricyclohexyltin hydroxide, hexakis(β,β-dimethylphenethyl)-distanoxane, 2-(4-t-butylphenoxy)cyclohexylpropinyl-sulfide, 3-methyl-1,5-bis(2,4-xylyl)-1,3,5-triazapenta-1,4-diene, 2,4,5,4,-tetrachlorodiphenyl sulfone, hexachlorohexahydromethanobenzodioxathiepine oxide, 5-dimethylamino-1,2,3-trithiane hydrogen oxalate and machine oil.

However, the nature of any such additional insecticide is not critical.

Additionally, if desired, the compounds of the present invention may be blended with other conventional agricultural or horticultural materials, such as acaricides, nematocides, herbicides, plant growth regulators, manure or soil conditioners, to provide compositions having a wider range of applications and/or to reduce labor costs.

The amount of the compound of the present invention used varies depending upon the weather conditions, the type of preparation, the time of application, the method of application, the nature of the environment, the nature of the disease, the nature of the plant and various other known factors, but the compound may preferably be applied in an amount of from 0.1 to 100 g of the effective ingredient per are, perferably from 5 to 40 g. Emulsifiable concentrates, wettable powders, suspension concentrates and the like are preferably applied by diluting a prescribed amount with, for example, from 1 to 10 liters of water per are and granules are generally applied without dilution. If desired, other additives, such as spreaders, e.g. surface active agents, polyoxyethylene resin acid, ligninsulfonates, salts of abietic acid, dinaphthylmethanedisulfonate, paraffin, may be added to the water used for the dilution.

The compounds of the present invention can also be used as pharmaceuticals for the treatment of fungal infections, whether of the skin, in which case they are normally administered topically, or internal infections, in which case they may be administered orally or parenterally. They are thought to be of especial value in the treatment of acute myoosis, such as candidiasis.

Where the compound of the present invention is employed for pharmaceutical use, it may be administered in the form of any conventional pharmaceutical formulation, the nature of which will, as is well known, depend on the route of administration and the nature of the condition to be treated. Thus, the compounds of the invention may be formulated in conventional dosage forms, normally in admixture with a pharmaceutical carrier or diluent. For oral administration, the compounds can be formulated, for example, as tablets, capsules, granules, powders or syrups. For parenteral administration, they may be formulated as injections in a suitable liquid or as suppositories. For topical administration, they may be formulated as ointments, creams, powders, liquids or aerosols. These pharmaceutical preparations can be produced by conventional means using adjuvants generally known in this field, such as excipients, diluents, dispersants, binders, disintegrators, lubricants, stabilizers, corrigents and the like.

The dosage and frequency of administration may vary depending upon the symptoms, age and body weight of the patient, as well as upon the route of administration, but, in general, the compounds of the invention may be administered orally in a daily dose of from 50 to 2,000 mg for an adult, preferably a dosage of from 100 to 600 mg, which may be administered either as single dose or as divided doses.

The preparation of the compounds of the present invention is illustrated by the following Examples, whilst the preparation of certain starting materials used in these Examples is illustrated by the subsequent Preparations. The use of the compounds to prepare pharmaceutical compositions is then illustrated by the Formulations, and their biological activity is shown by the Experiments which follow. In the Formulations, all parts and percentages are by weight, and mesh sizes use the Tyler standard mesh.

EXAMPLE 1

(2R*,3S*,4R*)-2-(2,4-Difluorophenyl)-3,4-dimethyl-2-[(1H-1,2,4-triazol-1-yl)methyl]oxetane and its oxalate and nitrate 309 mg of an aqueous solution of sodium methyl mercaptan having a concentration of about 15% were added to a solution of 389 mg of (2R*,3S*,4S*)-2-(2,4-difluorophenyl)-4-(methanesulfonyloxy)-3-methyl-1-(1H-1,2,4-triazol-1-yl)-2-pentanol [prepared as described in Preparation 2(c), derived from the 4,5-epoxy compound having the lower polarity of the stereoisomers prepared as described in Preparation 2(a) and being one of the isomers at the oxetane $C_4$ position] dissolved in 10 ml of methanol. The mixture was stirred overnight at room temperature and then poured into ice-water, after which it was extracted with ethyl acetate. The extract was washed with a saturated aqueous solution of sodium chloride and dried over anhydrous sodium sulfate, after which the solvent was removed by distillation under reduced pressure. The resulting oily residue (256 mg) was subjected to column chromatography through silica gel, using a 1:1 by volume mixture of hexane and ethyl acetate as the eluent, to afford 143 mg of the title compound as an oil.

Mass Spectrum (m/z): 279 (M+), 246, 231, 224, 213, 197, 182, 167, 149, 141, 127, 113, 101, 83.

Nuclear Magnetic Resonance Spectrum (CDCl$_3$), δ ppm: 0.83 (3H, doublet of doublets, J=7.2 Hz); 1.18 (3H, doublet, J=7 Hz); 3.18 (1H, quintet, J=7 Hz); 4.50 (1H, doublet, J=14.5 Hz); 4.58 (1H, quintet, J=7 Hz); 4.94 (1H, doublet, J=14.5 Hz); 6.8–6.9 (2H, multiplet); 7.4–7.5 (1H, multiplet); 7.87 (1H, singlet); 8.24 (1H, singlet).

Infrared Absorption Spectrum (liquid film), $v_{max}$ cm$^{-1}$: 3100, 1610, 1600.

33 mg of oxalic acid were added to a solution of 100 mg of the oxetane synthesized as described above dissolved in ethyl acetate, after which hexane was added to precipitate crystals. These crystals, melting at 145°–150° C., were collected by filtration, to give 92 mg of the oxalate of the title compound.

Nuclear Magnetic Resonance Spectrum (hexadeuterated dimethyl sulfoxide), δ ppm: 0.74 (3H, doublet of doublets, J=7 & 2 Hz); 1.10 (3H, doublet, J=7 Hz); 2.7–4.5 (2H, broad singlet); 3.18 (1H, quintet, J=7 Hz); 4.57 (1H, quintet, J=7 Hz); 4.66 (1H, quintet, J=7 Hz); 4.93 (1H, doublet, J=14.5 Hz); 7.05 (1H, doublet of triplets, J=8.5 & 2.5 Hz); 7.2–7.4 (2H, multiplet); 7.80 (1H, singlet); 8.40 (1H, singlet).

Infrared Absorption Spectrum (Nujol - trade mark), $v_{max}$ cm$^-$: 3500, 3130, 2800–2300, 1740, 1610, 1600.

1 ml of each of nitric acid (d=1.38) and diethyl ether were added to a solution of 100 mg of the oxetane synthesized as described above in methylene chloride. The crystals which were then deposited were collected by filtration, to give 115 mg of the nitrate of the title compound, melting at 160°–177° C.

Nuclear Magnetic Resonance Spectrum (hexadeuterated dimethyl sulfoxide), δ ppm: 0.75 (3H, doublet of doublets, J=7 & 2 Hz); 1.1 (3H, doublet, J=7 Hz); 3.19 (1H, quintet, J=7 Hz); 4.59 (1H, doublet, J TM 14.5 Hz); 4.70 (1H, quintet, J=7 Hz); 4.93 (1H, doublet, J=14.5 Hz); 7.05 (1H, doublet of triplets, J=8.5 & 3 Hz); 7.2–7.3 (1H, multiplet); 7.89 (1H, singlet); 8.53 (1H, singlet).

EXAMPLE 2

4S*)-2-(2,4-Difluorophenyl)-3,4-dimethyl-2-[(1H-b 1,2,4-triazol-1-yl)methyl]oxetane This is a stereoisomer of the compound of Example 1 at the C4 position.

Following a procedure similar to that described in Example 1, but using 221 mg of (2R*,3S*,4R*)-2-(2,4-difluorophenyl)-4-(methanesulfonyloxy)-3-methyl-1-(1H-1,2,4-triazol-1-yl)-2-pentanol [a stereoisomer of the starting material in Example 1 at the C4 position obtained by treating stereoisomer B of Preparation 2(a) as described in Preparations 2(b) and 2(c)], there were obtained 43 mg of the title compound as an oil.

Mass Spectrum (m/z): 280 (M+ +1), 279, 270, 256, 234, 224, 197, 179, 165, 151, 142, 127, 113, 101, 82.

Nuclear Magnetic Resonance Spectrum (CDCl3), δ ppm: 0.86 (3H, doublet of doublets, J=7 & 2.5 Hz); 1.11 (3H, doublet, J=7 Hz); 2.73 (1H, quintet, J=7 Hz);
4.23 (1H, quintet, J=7 Hz);
4.42 (1H, doublet, J=14.5 Hz);
4.81 (1H, doublet, J=14.5 Hz);
6.8–7.0 (2H, multiplet);
7.5–7.7 (1H, multiplet);
7.93 (1H, singlet);
8.28 (1H, singlet).

Infrared Absorption Spectrum (liquid film), $v_{max}$ cm$^{-1}$: 1610, 1600.

Recrystallization of this oil from ethyl acetate gave a pure specimen, melting at 105°–107° C.

EXAMPLE 3

(2R*,3R*,4R*)-2-(2,4-Difluorophenyl)-3,4-dimethyl-2-[(1H-1,2,4-triazol-1-yl)methyl]oxetane This is a stereoisomer of the compound of Example 1 at the C3-position.

Following a procedure similar to that described in Example 1, but using 255 mg of (2R*,3R*,4S*)-2-(2,4-difluorophenyl)-4-(methanesulfonyloxy)-3-methyl-1-(1H-1,2,4-triazol-1-yl)-2-pentanol [which was obtained by mesylation, as described in Preparation 2(c), of the major stereoisomeric component of the product prepared as described in Preparation 4 and being one of the isomers at the C4 position], there were obtained 135 mg of the title compound, melting at 100°–110° C.

Mass Spectrum (m/z): 279 (M+), 235, 224, 215, 197, 182, 166, 153, 141, 133, 127, 113, 101, 83.

Nuclear Magnetic Resonance Spectrum (CDCl3), δ ppm: 1.37 (3H, doublet, J=6 Hz); 1.39 (3H, doublet, J=7 Hz); 2.80 (1H, quintet, J=7 Hz); 4.63 (1H, quintet, J=7 Hz); 4.67 (1H, doublet, J=14 Hz); 4.94 (1H, doublet, J=14 Hz); 6.6–6.8 (2H, multiplet); 7.0–7.2 (1H, multiplet); 7.77 (1H, singlet); 8.02 (1H, singlet).

Infrared Absorption Spectrum (Nujol), $v_{max}$ cm$^{-1}$: 1610, 1600, 1490.

EXAMPLE 4

(2R*,3S*,4R*)-2-(2-Chlorophenyl)-3,4-dimethyl-2-[(1H-1,2,4-triazol-1-yl)methyl]oxetane 11 mg of a 60% by weight dispersion of sodium hydride in mineral oil were added to a solution of 51 mg of (2R*,3S*,4S*)-2-(2-chlorophenyl)-4-(methanesulfonyloxy)-3-methyl-1-(1H-1,2,4-triazol-1-yl)-2-pentanol [which was synthesized by a similar procedure to that described in Preparation 2(b) and 2(c) and derived from the 4,5-epoxy compound having the lower polarity of the stereoisomers at the C4 position prepared by a similar procedure to that described in Preparation 2(a)] in 2 ml of dimethylformamide; the mixture was then stirred at 60° C. for 2 hours. At the end of this time, the mixture was poured into ice-water and extracted with ethyl acetate. The extract was washed with water and dried over anhydrous sodium sulfate, and the solvent was removed by distillation under reduced pressure. The resulting oily residue was purified by preparative thin layer chromatography on silica gel, using a 1:2 by volume mixture of hexane and ethyl acetate as the developing solvent, to afford 10 mg of the title compound as an oil.

Mass Spectrum (m/z): 280 (M+ +2), 278 (M+), 259, 242, 222, 197, 195, 141, 139, 129, 111, 101, 89, 75.

Nuclear Magnetic Resonance Spectrum (CDCl3), δ ppm: 0.95 (3H, doublet, J=7 Hz); 1.18 (3H, doublet, J=7 Hz); 3.20 (1H, quintet, J=7 Hz); 4.60 (1H, quintet, J=7 Hz); 4.80 (1H, doublet, J=14.5 Hz); 5.19 (1H, doublet, J=14.5 Hz); 7.2–7.6 (4H, multiplet); 7.84 (1H, singlet); 8.12 (1H, singlet).

EXAMPLE 5

(2R*,3S*,4S*)-2-(2-Chlorophenyl)-3,4-dimethyl-1-[(1H-1,2,4-triazol-1-yl)methyl]oxetane This is a stereoisomer of the compound of Example 4 at the C4 position.

Following a procedure similar to that described in Example 4, but using 50.7 mg of (2R*,3S*,4R*)-2-(2-chlorophenyl)-4-(methanesulfonyloxy)-3-methyl-1-(1H-1,2,4-triazol-1-yl)-2-pentanol [which was synthesized in a similar manner to the procedure described in Preparation 2(b) and 2(c) and derived from the 4,5-epoxy compound having the higher polarity of the stereoisomers at the C4 position prepared by a similar procedure to that described in Preparation 2(a)], there were obtained 10 mg of the title compound as an oil.

Mass Spectrum (m/z): 280 (M+ +2), 278 (M+), 266, 253, 242, 222, 295, 141, 139, 129, 125, 111, 101, 89.

Nuclear Magnetic Resonance Spectrum (CDCl3), δ ppm: 0.99 (3H, doublet, J=7 Hz); 1.12 (3H, doublet, J=7 Hz); 2.80 (1H, quintet, J=7 Hz); 4.19 (1H, quintet, J=7 Hz); 4.66 (1H, doublet, J=14.5 Hz); 5.17 (1H, doublet, J=14.5 Hz); 7.2–7.7 (4H, multiplet); 7.90 (1H, singlet); 8.20 (1H, singlet).

EXAMPLE 6

(2R*,3S*,4R*)-2-(2-Chloro-4-fluorophenyl)-3,4-dimethyl-2-[(1H-1,2,4-triazol-1-yl)methyl]oxetane Following a procedure similar to that described in Example 4, but using 133 mg of (2R*,3S*,4S*)-2-(2-chloro-4-fluorophenyl)-4-(methanesulfonyloxy)-3-methyl-(1H-1,2,4-triazol-1-yl)-2-pentanol [which was synthesized in a similar manner to the procedure described in Preparation 2 and derived from the 4,5-epoxy compound having the lower polarity of the stereoisomers at the C4 position prepared by a similar procedure to that described in Preparation 2(a)], there were obtained 86 mg of the title compound as an oil.

Mass Spectrum (m/z): 297 (M+ +2), 295 (M+), 280, 278, 260, 251, 240, 216, 215, 214, 213, 182, 160, 159, 158, 157, 147, 129, 123, 107, 94, 82.

Nuclear Magnetic Resonance Spectrum (CDCl3), δ ppm: 0.94 (3H, doublet, J=7 Hz); 1.18 (3H, doublet, J=7 Hz); 3.18 (1H, quintet, J=7 Hz); 4.62 (1H, quintet, J=7 Hz); 4.80 (1H, doublet, J=14.5 Hz); 5.14 (1H, doublet, J=14.5 Hz); 6.9-7.0 (1H, multiplet); 7.12 (1H, doublet of doublets, J=8.5 & 2.5 Hz); 7.50 (1H, doublet of doublets, J=8.5 & 6.0 Hz); 7.83 (1H, singlet); 8.17 (1H, singlet).

EXAMPLE 7

(2R*,3S*,4S*)-2-(2-Chloro-4-fluorophenyl)-3,4-dimethyl-2-[(1H-1,2,4-triazol-1-yl)methyl]oxetane This is a stereoisomer of the compound of Example 6 at the $C_4$ position.

Following a procedure similar to that described in Example 4, but using 32 mg of (2R*,3S*,4R*)-2-(2-chloro-4-fluorophenyl)-4-(methanesulfonyloxy)-3-methyl-1-(1H-1,2,4-triazol-1-yl)-2-pentanol [which was synthesized in a similar manner to the procedure described in preparation 2(b) and 2(c) and derived from the 4,5-epoxy compound having the higher polarity of the stereoisomers at the $C_4$ position prepared by a similar procedure to that described in Preparation 2(a)], there were obtained mg of the title compound as an oil.

Mass Spectrum (m/z): 296 (M+), 279, 260, 240, 213, 211, 204, 182, 171, 159, 157, 143, 129, 123, 107, 94, 82.

Nuclear Magnetic Resonance Spectrum (CDCl$_3$), δ ppm: 0.98 (3H, doublet, J=7 Hz); 1.15 (3H, doublet, J=7 Hz); 2.79 (1H, quintet, J=7 Hz); 4.18 (1H, quintet, J=7 Hz); 4.67 (1H, doublet, J=14.5 Hz); 5.10 (1H, doublet, J=14.5 Hz); 6.9-7.1 (1H, multiplet); 7.17 (1H, doublet of doublets, J=8.5 & 2.5 Hz); 7.68 (1H, doublet of doublets, J=8.5 & 6.5Hz); 7.90 (1H, singlet); 8.22 (1H, singlet).

EXAMPLE 8

(2R*,3R*)-2-(2-Chloro-4-fluorophenyl)-3,4-dimethyl-2-[(1H-1,2,4-triazol-1-yl)methyl]oxetane This is a stereoisomer of the compound of Example 6 at the C$_3$-position.

Following a procedure similar to that described in Example 4, but using 139 mg of (2R*,3R*)-2-(2-chloro-4-fluorophenyl)-4-(methanesulfonyloxy)-3-methyl-1-(1H-1,2,4-triazol-1-yl)-2-pentanol (which was obtained by mesylation of the major stereoisomeric component, isomeric at the C$_4$ position, of a diol compound synthesized in a similar manner to the procedure described in Preparation 4), there were obtained 91 mg of the title compound as crystals, melting at 145°-147° C.

Mass Spectrum (m/z): 97 (M++2), 295, 260, 240, 213, 211, 198, 179, 159, 158, 149, 129, 123, 109, 98, 83.

Nuclear Magnetic Resonance Spectrum (CDCl$_3$), δ ppm: 1.32 (3H, doublet, J=7 Hz); 1.5 (3H, doublet, J=7 Hz); 2.81 (1H, quintet, J=7 Hz); 4.59 (1H, quintet, J=7 Hz); 4.91 (2H, singlet); 6.7-6.8 (1H, multiplet); 7.09 (1H, doublet of doublets, J=8.5 & 2.5 Hz); 7.20 (1H, doublet of doublets, J=8.5 & 6.0 Hz); 7.69 (1H, singlet); 7.94 (1H, singlet).

EXAMPLE 9

(2R*,3S*,4S*)-2-(4-Chloro-2-fluorophenyl)-3,4-dimethyl-2-[(1H-1,2,4-triazol-1-yl)methyl]oxetane Following a procedure similar to that described in Example 4, but using 260 mg of (2R*,3S*,4R*)-2-(2-fluoro-4-chlorophenyl)-4-(methanesulfonyloxy)-3-methyl-1-(1H-1,2,4-triazol-1-yl)-2-pentanol [which was synthesized by a similar procedure to that described in Preparation 2(b) and 2(c) and derived from the 4,5-epoxy compound having the higher polarity of the stereoisomers at the C$_4$ position prepared by a similar procedure to that described in Preparation 2(a)], there were obtained. 150 mg of the title compound as an oil.

Mass Spectrum (m/z): 297 (M++2), 295 (M+), 280, 250, 240, 215, 214, 206, 179, 159, 158, 143, 129, 123, 109, 99, 94, 82.

Nuclear Magnetic Resonance Spectrum.(CDCl$_3$), δ ppm: 0.84 (3H, doublet of doublets, J=7 & 2.5 Hz); 1.10 (3H, doublet, J=7 Hz); 2.74 (1H, quintet, J=7 Hz); 4.21 (1H, quintet, J=7 Hz); 4.40 (1H, doublet, J=14.5 Hz); 4.80 (1H, doublet, J=14.5 Hz); 7.14 (1H, doublet of doublets, J=10.5 & 2.0 Hz); 7.20 (1H, doublet of doublets, J=8 & 2.0 Hz); 7.56 (1H, triplet, J=8 Hz); 7.91 (1H, singlet); 8.22 (1H, singlet).

Infrared Absorption Spectrum (liquid film), ν$_{max}$ cm$^{-1}$: 3120, 1610, 1570.

EXAMPLE 10

(2R*,3S*,4R*)-2-(2-Fluoro-4-chlorophenyl)-3,4-dimethyl-2-[(1H-1,2,4-triazol-1-yl)methyl]oxetane This is a stereoisomer of the compound of Example 9 at the C$_4$ position.

Following a procedure similar to that described in Example 4, but using 390 mg of (2R*,3S*,4S*)-2-(2-fluoro-4-chlorophenyl)-4-(methanesulfonyloxy)-3-methyl-1-(1H-1,2,4-triazol-1-yl)-2-pentanol [which was synthesized in a similar manner to the procedure described in Preparation 2(b) and 2(c) and derived from the 4,5-epoxy compound having the lower polarity of the stereoisomers at the C$_4$ position prepared by a similar procedure to that described in Preparation 2(a)], there were obtained 220 mg of the title compound as an oil.

Mass Spectrum (m/z): 297 (M++2), 295 (M+), 247, 240, 215, 214, 182, 159, 158, 157, 147, 129, 122, 107, 94, 82.

Nuclear Magnetic Resonance Spectrum (CDCl$_3$), δ ppm: 0.83 (3H, doublet of doublets, J=7 & 2.0 Hz); 1.17 (3H, doublet, J=7 Hz); 3.19 (1H, quintet, J=7 Hz); 4.49 (1H, doublet, J=14.5 Hz); 4.57 (1H, quintet, J=7 Hz); 4.90 (1H, doublet, J=14.5 Hz); 7.0-7.1 (1H, multiplet); 7.15 (1H, doublet of doublets, J=8.5 & 2.0 Hz); 7.46 (1H, triplet, J=8.5 Hz); 7.86 (1H, singlet); 8.21 (1H, singlet).

Infrared Absorption Spectrum (liquid film), ν$_{max}$ cm$^{-1}$: 3110, 1610, 1570.

EXAMPLE 11

(2R*,3S*,4R*)-2-(2,6-Difluorophenyl)-3,4-dimethyl-2-[(1H-1,2,4-triazol-1-yl)methyl]oxetane Following a procedure similar to that described in Example 4, but using 120 mg of (2R*,3S*,4S*)-2-(2,6-difluorophenyl)-4-(methanesulfonyloxy)-3-methyl-1-(1H-1,2,4-triazol-1-yl)-2-pentanol [which was synthesized by a similar procedure to that described in Preparation 2(b) and 2(c) and derived from the 4,5-epoxy compound having the lower polarity of the stereoisomers at the C$_4$ position prepared by a similar procedure to that described in Preparation 2(a)], there were obtained 63 mg of the title compound as an oil.

Mass Spectrum (m/z): 297 (M+), 224, 197, 179, 166, 151, 141, 127, 113, 101, 82.

Nuclear Magnetic Resonance Spectrum (CDCl$_3$), δ ppm: 1.00 (3H, doublet of triplets, J=7 & 1 Hz); 1.24 (3H, doublet, J=7 Hz); 3.20 (1H, quintet, J=7 Hz); 4.57 (1H, quintet, J=7 Hz); 4.60 (1H, doublet, J=14.5 Hz); 4.92 (1H, doublet, J=14.5 Hz); 6.86 (2H, triplet, J=9

Hz); 7.2–7.3 (1H, multiplet); 7.87 (1H, singlet); 8.31 (1H, singlet).

EXAMPLE 12

(2R*,3S*,4S*)-2-(2,6-difluorophenyl)-3,4-dimethyl-2-[(1H-1,2,4-triazol-1-yl)methyl]oxetane This is a stereoisomer of the compound of Example 11 at the C$_4$ position.

Following a procedure similar to that described in Example 4, but using 121 mg of (2R*,3S*,4R*)-2-(2,6-difluorophenyl)-4-(methanesulfonyloxy)-3-methyl-1-(1H-1,2,4-triazol-1-yl)-2-pentanol [which was synthesized in a similar manner to the procedure described in Preparation 2(b) and 2(c) and derived from the 4,5-epoxy compound having the higher polarity of the stereoisomers at the C$_4$ position prepared by a similar procedure to that described in Preparation 2(a)], there were obtained 44 mg of the title compound as an oil.

Mass Spectrum (m/z): 279 (M+), 261, 235, 224, 206, 197, 179, 166, 153, 141, 133, 123, 113, 95, 82.

Nuclear Magnetic Resonance Spectrum (CDCl$_3$), δ ppm: 0.99 (3H, doublet of triplets, J=7 & 2 Hz); 1.10 (3H, doublet, J=7 Hz); 2.82 (1H, quintet, J=7 Hz); 4.38 (1H, quintet, J=7 Hz); 4.55 (1H, doublet, J=14.5 Hz); 4.83 (1H, doublet, J=14.5 Hz); 6.8–7.0 (2H, multiplet); 7.2–7.4 (1H, multiplet); 7.92 (1H, singlet); 8.33 (1H, singlet).

EXAMPLE 13

(2R*,3S*)-2-(2,4-Difluorophenyl)-3-methyl-2-[(1H-1,2,4-triazol-1-yl)methyl]oxetane Following a procedure similar to that described in Example 1, but using 100 mg of (2R*,3S*)-2-(2,4-difluorophenyl)-4-(methanesulfonyloxy)-3-methyl-1-(1H-1,2,4-triazol-1-yl)-2-butanol (which was synthesized in a similar manner to the procedure described in Preparation 7), there were obtained 54 mg of the title compound as an oil.

Mass Spectrum (m/z): 265 (M+), 247, 232, 224, 184, 183, 165, 153, 141, 133, 127, 113, 101, 94, 82.

Nuclear Magnetic Resonance Spectrum (CDCl$_3$), δ ppm: 0.93 (3H, doublet of doublets, J=7 & 2 Hz); 3.15 (1H, sextet, J=7 Hz); 3.99 (1H, triplet, J=7 Hz); 4.37 (1H, doublet of doublets, J=7 & 6 Hz); 4.48 (1H, doublet, J=14.5 Hz); 4.90 (1H, doublet, J=14.5 Hz); 6.8–7.0 (2H, multiplet); 7.2–7.4 (1H, multiplet); 7.90 (1H, singlet); 8.30 (1H, singlet).

EXAMPLE 14

2-(2,4-Difluorophenyl)-4-methyl-2-[(1H-1,2,4-triazol-1-yl)methyl]oxetane

Following a procedure similar to that described in Example 4, but using 590 mg of 2-(2,4-difluorophenyl)-4-(methanesulfonyloxy)-4-methyl-(1H-1,2,4-triazol-1-yl)-2-butanol (which was synthesized from allylmagnesium chloride in a similar manner to the procedure described in Japanese Patent Provisional Publication No. Sho 59-517 and Preparations 2, 3 and 4), one of the stereoisomers at the C$_4$ position was obtained as the major product in the form of an oil.

Mass Spectrum (m/z): 65 (M+), 250, 224, 202, 184, 183, 142, 141 133, 127, 119, 113, 99, 83.

Nuclear Magnetic Resonance Spectrum (CDCl$_3$), δ ppm: 1.28 (3H, doublet, J=6 Hz); 2.35 (1H, doublet of quartets, J=8 & 6 Hz); 3.10 (1H, doublet of doublets, J=8 & 7 Hz); 4.34 (1H, doublet, J=14.5 Hz); 4.3–4.5 (1H, multiplet); 4.72 (1H, doublet, J=14.5 Hz); 6.8–6.9 (2H, multiplet); 7.4–7.5 (1H, multiplet); 7.90 (1H, singlet); 8.20 (1H, singlet).

Infrared Absorption Spectrum (liquid film), ν$_{max}$ cm$^{-1}$: 1610, 1600, 1500.

EXAMPLE 15

(2R*,3S*)-2-(2,4-Dichlorophenyl)-3-methyl-2-[(1H-1,2,4-triazol-1-yl)methyl]oxetane and its nitrate Following a procedure similar to that described in Example 1, but using 72 mg of (2R*,3S*)-2-(2,4-dichlorophenyl)-4-(methanesulfonyloxy)-3-methyl-1-(1H-1,2,4-triazol-1-yl)-2-butanol (which was synthesized in a similar manner to the procedure described in Preparation 7), there were obtained 25 mg of the title compound as an oil.

Nuclear Magnetic Resonance Spectrum (CDCl$_3$), δ ppm: 1.05 (3H, doublet, J=7 Hz); 3.15 (1H, multiplet); 3.90 (1H, doublet of doublets, J=6 & 5.5 Hz); 4.38 (1H, doublet of doublets, J=7 & 6 Hz); 4.67 (1H, doublet, J=14.5 Hz); 5.16 (1H, doublet, J=14.5 Hz); 7.1–7.6 (3H, multiplet); 7.88 (1H, singlet); 8.20 (1H, singlet).

Infrared Absorption Spectrum (CHCl$_3$), ν$_{max}$ cm$^{-1}$: 1590, 1275, 1137, 975.

About 0.1 ml of an ethereal solution containing 5% acid was added to a solution of 17 mg of the title oxetane compound in 0.4 ml of diethyl ether, whilst ice-cooling. The mixture was then treated by conventional means, to afford 17 mg of the nitrate of the title compound as crystals, melting at 162°–165° C.

EXAMPLE 16

(2R*,3S*)-2-(2,4-Dichlorophenyl)-3,4-dimethyl-2-[1H-1,2,4-triazol-1-yl)methyl]oxetane and its nitrate 0.5 ml of an aqueous solution containing 15% w/v of sodium methyl mercaptan was added to a solution of 54 mg of a 1:1 mixture of the C$_4$ stereoisomers of a mesylate compound [which was derived from a 1:1 mixture of the C$_4$ stereoisomers of (2R*,3S*)-2-(2,4-dichlorophenyl)-3-methyl-1-(1H-1,2,4-triazol-1-yl)-2,4-pentanediol (which was synthesized in a similar manner to the procedure described in Preparation 4)] in 1 ml of dimethylformamide. The mixture was then stirred at 50°–60° C. for 2 hours, after which it was treated following a procedure similar to that described in Example 1. The resulting crude product was purified by preparative thin layer chromatography through silica gel, using a 3:1 by volume mixture of ethyl acetate and hexane as the developing solvent, to afford 8 mg of a stereoisomer A (of lower polarity) and 10 mg of a stereoisomer B (of higher polarity), both as oils.

Stereoisomer A (2R*,3S*,4S*):

Nuclear Magnetic Resonance Spectrum (CDCl$_3$), δ ppm: 0.98 (3H, doublet, J=7 Hz); 1.03 (3H, doublet, J=7 Hz); 2.80 (1H, quintet, J=7 Hz); 4.19 (1H, quintet, J=7 Hz); 4.62 (1H, doublet, J=15 Hz); 5.12 (1H, doublet, J=15 Hz); 7.31 (1H, doublet of doublets, J=9 & 2 Hz); 7.46 (1H, doublet, J=2 Hz); 7.71 (1H, doublet, J=9 Hz); 7.90 (1H, singlet); 8.20 (1H, singlet).

Stereoisomer B (2R*,3S*,4R*):

Nuclear Magnetic Resonance Spectrum (CDCl$_3$), δ ppm: 0.92 (3H, doublet, J=7 Hz); 1.17 (3H, doublet, J=7 Hz); 3.17 (1H, quintet, J=7 Hz); 4.59 (1H, quintet, J=7 Hz); 4.72 (1H, doublet, J=15 Hz); 5.15 (1H, doublet, J=15 Hz); 7.20 (1H, doublet of doublets, J=9 & 1.5 Hz); 7.38 (1H, doublet, J=1.5 Hz); 7.50 (1H, doublet, J=9 Hz); 7.81 (1H, singlet); 8.13 (1H, singlet).

Each of these isomers was converted to its nitrate conventional means, by adding an ethereal solution containing 5% nitric acid to a solution of the respective oxetane compound, whilst ice-cooling, to give the desired nitrates as crystals.

The nitrate of stereoisomer A melted at 150°–165° C.
The nitrate of stereoisomer B melted at 160°–164° C.

EXAMPLE 17

2-(2,4-Difluorophenyl)-2-[(1H-1,2,4-triazol-1-yl)methyl]-3,3,4-trimethyloxetane

Following a procedure similar to that described in Preparation 2(a), two stereoisomers of a 4,5-epoxy compound were synthesised from 2-(2,4-difluorophenyl)-3,3-dimethyl-1-(1H-1,2,4-triazol-1-yl)-4-penten-2-ol. The stereoisomer having the lower polarity was then converted to 2-(2,4-difluorophenyl)-3,3-dimethyl-1-(1H-1,2,4-triazol-1-yl)-2,4-pentanediol, according to the procedure described in Preparation 4. This was then mesylated by the procedure described in Preparation 2(c), to give 2-(2,4-difluorophenyl)-3,3-dimethyl-4-(methanesulfonyloxy)-1-(1H-1,2,4-triazol-1-yl)-2-pentanol.

10 mg of sodium hydride were added to a solution of 77 mg of this 2-(2,4-difluorophenyl)-3,3-dimethyl-4-(methanesulfonyloxy)-1-(1H-1,2,4-triazol-1-yl)-2-pentanol in 1.5 ml of tetrahydrofuran, whilst ice-cooling and stirring, after which 0.1 ml of methanol was added. After 10 minutes, the reaction mixture was diluted with water and extracted with ethyl acetate. The resulting crude product was purified by column chromatography through silica gel, using a 3:2 by volume mixture of ethyl acetate and hexane as the eluent. The resulting compound was recrystallized from cyclohexane to afford 39 mg of a pure specimen of the title compound, melting at 112°–113° C.

Nuclear Magnetic Resonance Spectrum (CDCl$_3$), δ ppm: 0.86 (3H, singlet); 1.24 (3H, doublet, J=6 Hz); 1.36 (3H, singlet); 4.72 (1H, doublet, J=15 Hz); 4.82 (1H, quartet, J=6 Hz); 5.02 (1H, doublet, J=15 Hz); 6.5–7.4 (3H, multiplet); 7.61 (1H, singlet); 7.94 (1H, singlet).

EXAMPLE 18

2-(2,4-Difluorophenyl)-2-[(1H-1,2,4-triazol-1-yl)methyl]-3,3,4-trimethyloxetane

This is a stereoisomer of the compound of Example 17 at the C$_4$ position.

Following a procedure similar to that described in Preparation 2(a), two stereoisomers of a 4,5-epoxy compound were synthesised from 2-(2,4-difluorophenyl)-3,3-dimethyl-1-(1H-1,2,4-triazol-1-yl)-4-penten-2-ol. The stereoisomer having the higher polarity was then converted to 2-(2,4-difluorophenyl)-3,3-dimethyl-1-(1H-1,2,4-triazol-1-yl)-2,4-pentanediol, according to the procedure described in Preparation 4. This was then mesylated by the procedure described in Preparation 2(c), to give 2-(2,4-difluorophenyl)-3,3-dimethyl-4-(methanesulfonyloxy)-1-(1H-1,2,4-triazol-1-yl)-2-pentanol.

Following a procedure similar to that described in Example 17, but using the 4-mesylate compound prepared as described above, the title compound was prepared and was recrystallized from a mixture of benzene and hexane to give a pure specimen, melting at 93°–94° C.

Nuclear Magnetic Resonance Spectrum (CDCl$_3$), δ ppm: 0.93 (3H, doublet, J=2 Hz); 1.34 (3H, singlet); 1.44 (3H, doublet, J=6.5 Hz); 4.50 (1H, quartet, J=6.5 Hz); 4.81 (2H, singlet); 6.6–7.1 (2H, multiplet); 7.23 (1H, triplet of doublets, J=9 & 6 Hz); 7.60 (1H, singlet); 7.96 (1H, singlet).

EXAMPLE 19

(2R*,3S*,4R*)-2-(4-Trifluoromethoxyphenyl)-3,4-dimethyl-2-[(1H-1,2,4-triazol-1-yl)methyl]oxetane Following a procedure similar to that described in Example 4, but using 250 mg of (2R*,3S*,4S*)-2-(4-trifluoromethoxyphenyl)-4-(methanesulfonyloxy)-3-methyl-1-(1H-1,2,4-triazol-1-yl)-2-pentanol [which was synthesized by a similar procedure to that described in Preparation 2(b) and 2(c) and derived from the 4,5-epoxy compound having the lower polarity of the stereoisomers at the C$_4$ position prepared by a similar procedure to that described in Preparation 2(a)], there were obtained 82 mg of the title compound as an oil.

Mass Spectrum (m/z): 328 (M$^+$ +1), 308, 272, 245, 214, 197, 190, 189, 175, 161, 141, 129, 115, 95, 82.

Nuclear Magnetic Resonance Spectrum (CDCl$_3$), δ ppm: 0.70 (3H, doublet, J=7.5 Hz); 1.16 (3H, doublet, J=6.5 Hz); 3.18 (1H, quintet, J=7.5 Hz); 4.35 (1H, doublet, J=14.5 Hz); 4.39 (1H, doublet of quartets, J=7.5 & 6.5 Hz); 4.70 (1H, doublet, J=14.5 Hz); 7.2–7.4 (4H, multiplet); 7.93 (1H, singlet); 8.23 (1H, singlet).

Infrared Absorption Spectrum (liquid film), ν$_{max}$ cm$^{-1}$: 1610, 1590, 1500, 1260, 1160, 1020.

EXAMPLE 20

(2R*,3S*,4R*)-2-(4-Chlorophenyl)-3,4-dimethyl-2-(1H-1,2,4-triazol-1-yl)methyl]oxetane Following a procedure similar to that described in Example 4, but using 230 mg of (2R*,3S*,4S*)-2-(4-chlorophenyl)-4-(methanesulfonyloxy)-3-methyl-1-(1H-1,2,4-triazol-1-yl)-2-pentanol [which was synthesized by a similar procedure to that described in Preparation 2(b) and 2(c) and derived from the 4,5-epoxy compound having the lower polarity of the stereoisomers at the C$_4$ position prepared by a similar procedure to that described in Preparation 2(a)], there were obtained 112 mg of the title compound, melting at 111°–118° C.

Mass Spectrum (m/z): 278 (M$^+$ +1), 256, 222, 197, 164, 149, 141, 139, 129, 111, 104.

Nuclear Magnetic Resonance Spectrum (CDCl$_3$), δ ppm: 0.70 (3H, doublet, J=7.25 Hz); 1.17 (3H, doublet, J=6.45 Hz); 3.16 (1H, quintet, J=7.25 Hz); 4.41 (1H, doublet, J=14.5 Hz); 4.4–4.53 (1H, multiplet); 4.76 (1H, doublet, J=14.5 Hz); 7.25 (2H, doublet, J=8.46 Hz); 7.36 (2H, doublet, J=8.46 Hz); 7.98 (1H, singlet); 8.42 (1H, singlet).

EXAMPLE 21

2-(4-Chlorophenyl)-3,3-dimethyl-2-[(1H-1,2,4-triazol-1-yl)methyl]oxetane 160 mg of sodium hydride (as a 60% w/w dispersion in mineral oil) were added to a solution of 750 mg of 2-(4-chlorophenyl)-3,3-dimethyl-4-methanesulfonyloxy-1-(1H-1,2,4-triazol-1-yl)-2-butanol in 12 ml of dimethylformamide, and the resulting mixture was stirred at room temperature for 3 hours. At the end of this time, the reaction mixture was poured into ice-water and extracted with ethyl acetate. The extract was washed with an aqueous solution of ammonium chloride, dried over anhydrous magnesium sulfate and concentrated by evaporation under reduced pressure. The resulting residue was purified by preparative thin layer chromatography, using a 1:4 by volume mixture of ethyl acetate and hexane as the developing solvent, to afford 170 mg (yield 31%) of the title compound, melting at 90°-102° C.

Nuclear Magnetic Resonance Spectrum (CDCl$_3$, 60 MHz), δ ppm: 0.90 (3H, singlet); 1.38 (3H, singlet); 4.11 (1H, doublet, J=6 Hz); 4.50 (1H, doublet, J=6 Hz); 4.60 (1H, doublet, J=14 Hz); 5.00 (1H, doublet, J=14 Hz); 6.85-7.30 (4H, multiplet); 7.56 (1H, singlet); 7.81 (1H, singlet).

Mass Spectrum (m/z): 277 (M+), 222, 195, 137.

EXAMPLES 22 TO 32

Using a procedure similar to that described in Example 21, the following compounds were synthesized.

EXAMPLE 22

2-(2,4-Difluorophenyl)-2-[(1H-1,2,4-triazol-1-yl)methyl]-oxetane, as an oil, in a yield of 56%.

Nuclear Magnetic Resonance Spectrum (CDCl$_3$), δ ppm: 2.66-2.77 (1H, multiplet); 2.93-3.04 (1H, multiplet); 4.15-4.23 (1H, multiplet); 4.34 (1H, doublet, J=14.9 Hz); 4.43-4.52 (1H, multiplet); 4.73 (1H, doublet, J=14.9 Hz); 6.81-6.93 (2H, multiplet); 7.39-7.48 (1H, multiplet); 7.94 (1H, singlet); 8.27 (1H, singlet).

Mass Spectrum, (m/z): 251 (M+), 170, 141.

EXAMPLE 23

2-(2,4-Difluorophenyl)-3-methyl-2-[(1H-1,2,4-triazol-1-yl)methyl]oxetane, as an oil, in a yield of 73%.

Nuclear Magnetic Resonance Spectrum (CDCl$_3$), δ ppm: 0.93 (3H, doublet of doublets, J=7 & 2 Hz); 3.15 (1H, sextet, J=7 Hz); 3.99 (1H, triplet, J=7 Hz); 4.37 (1H, doublet of doublets, J=7 & 6 Hz); 4.48 (1H, doublet, J=14.5 Hz); 4.90 (1H, doublet, J=14.5 Hz); 6.8-7.0 (2H, multiplet); 7.2-7.4 (1H, multiplet); 7.90 (1H, singlet); 8.30 (1H, singlet).

Mass Spectrum (m/z): 265 (M+), 247, 232, 224, 184, 183.

EXAMPLE 24

2-(2,4-Difluorophenyl)-3-ethyl-2-[(1H-1,2,4-triazol-1-yl)methyl]oxetane, as an oil, in a yield of 39%.

Nuclear Magnetic Resonance Spectrum (CDCl$_3$), δ ppm: 0.70 (3H, triplet, J=7.5 Hz); 1.03-1.15 (1H, multiplet); 1.46-1.56 (1H, multiplet); 2.87-2.98 (1H, multiplet); 4.07 (1H, multiplet); 4.34 (1H, multiplet); 4.48 (1H, doublet, J=14.5 Hz); 4.91 (1H, doublet, J=14.5 Hz); 6.80-6.94 (2H, multiplet); 7.44-7.53 (1H, multiplet); 7.88 (1H, singlet); 8.22 (1H, singlet).

Mass Spectrum, (m/z): 279 (M+), 224, 197, 141, 127.

EXAMPLE 25

2-(2,4-Difluorophenyl)-3,3-dimethyl-2-[(1H-1,2,4-triazol-1-yl)methyl]oxetane, melting at 78° C., in a yield of 72%.

Nuclear Magnetic Resonance Spectrum (CDCl$_3$), δ ppm: 1.04 (3H, singlet); 1.43 (3H, singlet); 4.18 (1H, doublet, J=5.6 Hz); 4.62 (1H, doublet, J=5.6 Hz); 4.79 (1H, doublet of doublets, J=14.1 & 1.6 Hz); 5.01 (1H, doublet, J=14.1 Hz); 6.68-6.83 (2H, multiplet); 7.1 (1H, doubled doublet of doublets, J=6.5, 6.5 & 2.0 Hz); 7.62 (1H, singlet); 7.95 (1H, singlet).

Mass Spectrum (m/z): 279 (M+), 261, 226, 197, 179, 167, 149.

EXAMPLE 26

2-(2,4-Difluorophenyl)-3-phenyl-2-[(1H-1,2,4-triazol-1-yl)methyl]oxetane, as an oil, in a yield of 50%.

Nuclear Magnetic Resonance Spectrum (CDCl$_3$), δ ppm: 4.28 (1H, triplet, J=7.5 Hz); 4.53-4.62 (2H, multiplet); 5.00 (2H, doublet, J=14.9 Hz); 6.37-6.45 (1H, multiplet); 6.83-6.90 (1H, multiplet); 7.00-7.15 (5H, multiplet); 7.47-7.56 (1H, multiplet); 7.98 (1H, singlet); 8.36 (1H, singlet).

EXAMPLE 27

2-(4-Chlorophenyl)-3-ethyl-2-[(1H-1,2,4-triazol-1-yl)methyl]oxetane, as an oil, in a yield of 40%.

Nuclear Magnetic Resonance Spectrum (CDCl$_3$), δ ppm: 0.63 (3H, triplet, J=7.3 Hz); 0.91-1.01 (1H, multiplet); 1.16-1.32 (1H, multiplet); 2.84-2.93 (1H, multiplet); 4.05-4.09 (1H, multiplet); 4.22-4.27 (1H, multiplet); 4.38 (1H, doublet, J=14.7 Hz); 4.74 (1H, doublet, J=14.7 Hz); 7.25-7.39 (4H, multiplet); 7.97 (1H, singlet); 8.32 (1H, singlet).

EXAMPLE 28

3,3-Dimethyl-2-(4-methylphenyl)-2-[(1H-1,2,4-triazol-1-yl)methyl]oxetane, melting at 76°-77° C., in a yield of 83%.

Nuclear Magnetic Resonance Spectrum (CDCl$_3$), δ ppm: 0.93 (3H, singlet); 1.41 (3H, singlet); 2.29 (3H, singlet); 4.19 (1H, doublet, J=5.6 Hz); 4.56 (1H, doublet, J=5.6 Hz); 4.63 (1H, doublet, J=14.1 Hz); 5.07 (1H, doublet, J=14.1 Hz); 6.99-7.02 (2H, multiplet); 7.07-7.10 (2H, multiplet); 7.69 (1H, singlet); 7.80 (1H, singlet).

Mass Spectrum, (m/z): 257 (M+), 202, 175.

EXAMPLE 29

2-(4-Isopropylphenyl)-3,3-dimethyl-2-[(1H-1,2,4-triazol-1-yl)methyl]oxetane, as an oil, in a yield of 67%.

Nuclear Magnetic Resonance Spectrum (CDCl$_3$), δ ppm: 0.92 (3H, singlet); 1.21 (6H, doublet, J=7.3 Hz); 1.41 (3H, singlet); 2.80-2.90 (1H, multiplet); 4.19 (1H, doublet, J=5.6 Hz); 4.55 (1H, doublet, J=5.6 Hz); 4.62 (1H, doublet, J=14.3 Hz); 6.97-7.15 (4H, multiplet); 7.69 (1H, singlet); 7.77 (1H, singlet).

Mass Spectrum, (m/z): 285 (M+), 230, 203.

EXAMPLE 30

2-(4-Methoxyphenyl)-3,3-dimethyl-2-[(1H-1,2,4-triazol-1-yl)methyl]oxetane, as an oil, in a yield of 29%.

Nuclear Magnetic Resonance Spectrum (CDCl$_3$), δ ppm: 0.92 (3H, singlet); 1.41 (3H, singlet); 3.77 (3H, singlet); 4.56 (1H, doublet, J=5.8 Hz); 4.59 (1H, doublet, J=5.8 Hz); 4.62 (1H, doublet, J=14.3 Hz); 5.06 (1H, doublet, J=14.3 Hz); 6.80-6.88 (2H, multiplet); 6.96-7.24 (2H, multiplet); 7.69 (1H, singlet); 7.81 (1H, singlet).

Mass Spectrum, (m/z): 273 (M+), 218, 191.

EXAMPLE 31

3-Ethyl-2-(4-fluorophenyl)-2-[(1H-1,2,4-triazol-1-yl)methyl]oxetane, melting at 43°-47° C., in a yield of 33%.

Nuclear Magnetic Resonance Spectrum (CDCl$_3$), δ ppm: 0.66 (3H, triplet, J=7.25 Hz); 0.87-1.01 (1H, multiplet); 1.20-1.32 (1H, multiplet); 2.81-2.92 (1H, multiplet); 4.08 (1H, triplet, J=6.2 Hz); 4.27 (1H, triplet, J=6.2 Hz); 4.39 (1H, doublet, J=14.9 Hz); 4.76 (1H, doublet, J=14.9 Hz); 7.09 (2H, triplet, J=8.9 Hz); 7.30-7.34 (2H, doublet of doublets, J=8.9 & 2 Hz); 7.98 (1H, singlet); 8.37 (1H, singlet).

Mass Spectrum (m/z): 262, (M+), 246, 206, 179.

EXAMPLE 32

2-(2,4-Dichlorophenyl)-3,3-dimethyl-2-[(1H-1,2,4-triazol-1-yl)methyl]oxetane, melting at 90°-100° C., in a yield of 60%.

Nuclear Magnetic Resonance Spectrum (CDCl3), δ ppm: 1.12 (3H, singlet); 1.50 (3H, singlet); 4.13 (1H, doublet, J=5.8 Hz); 4.62 (1H, doublet, J=5.8 Hz); 5.02 (1H, doublet, J=14.3 Hz); 5.27 (1H, doublet, J=14.3 Hz); 7.08 (1H, doublet of doublets, J=1.95 & 8.45 Hz); 7.17 (1H, doublet, J=8.45 Hz); 7.35 (1H, doublet, J=1.95 Hz); 7.66 (1H, singlet); 8.05 (1H, singlet).

Mass Spectrum, (m/z): 315 [(M+4)+], 313 [(M+2)+], 311 (M+), 276, 256, 231, 229, 199, 173.

EXAMPLE 33

(2R*,3S*,4S*)-2-(2,4-Difluorophenyl)-4-ethyl-3-methyl-2-[(1H-1,2,4-triazol-1-yl)methyl]oxetane 960 mg (0.24 mmole) of sodium hydride (as a 60% w/w dispersion in mineral oil) were added, whilst ice-cooling, to a solution of 77.9 mg (0.2 mmole) of 2-(2,4-difluorophenyl)-4-methanesulfonyloxy-3-methyl-1-(1H-1,2,4-triazol-1-yl)-2-hexanol in 4.9 ml of dimethylformamide. The resulting mixture was then stirred at room temperature for 3 hours. At the end of this time, the reaction mixture was poured into 20 ml of ice-water and extracted with 40 ml of ethyl acetate. The extract was washed with a saturated aqueous solution of sodium chloride, dried over anhydrous sodium sulfate and concentrated by evaporation under reduced pressure. The residue was purified by preparative thin layer chromatography, using a 2:1 by volume mixture of hexane and ethyl acetate as the developing solvent, to afford 13.0 mg (yield 22.2%) of the title compound as an oil.

Nuclear Magnetic Resonance Spectrum (CDCl3), δ ppm: 0.82 (3H, triplet, J=7.5 Hz); 0.87 (3H, doublet of doublets, J=2.42 & 6.9 Hz); 1.18-1.34 (1H, multiplet); 1.36-1.50 (1H, multiplet); 2.76 (1H, quintet, J=6.9 Hz); 3.98 (1H, quartet, J=6.91 Hz); 4.39 (1H, doublet, J=14.5 Hz); 4.79 (1H, doublet, J=14.5 Hz); 6.82-6.97 (2H, multiplet); 7.56-7.65 (1H, multiplet); 7.88 (1H, singlet); 8.18 (1H, singlet).

Mass Spectrum (m/z): 294 [(M+1)+], 224, 211.

EXAMPLES 34 & 35

Using a procedure similar to that described in Example 33, the following compounds were synthesized.

EXAMPLE 34

(2R*,3S*,4S*)-4-ethyl-2-(4-fluorophenyl)-3-methyl-2-[(1H-1,2,4-triazol-1-yl)methyl]oxetane, as an oil, in a yield of 7.5%.

Nuclear Magnetic Resonance Spectrum (CDCl3), δ ppm: 0.73 (3H, doublet, J=7.1 Hz); 0.82 (3H, triplet, J=7.5 Hz); 1.11-1.44 (2H, multiplet); 2.68 (1H, quintet, J=7.1 Hz); 4.01 (1H, quartet, J=7.1 Hz); 4.29 (1H, doublet, J=14.9 Hz); 4.59 (1H, doublet, J=14.9 Hz); 7.08-7.15 (2H, multiplet); 7.31-7.38 (2H, multiplet); 7.97 (1H, singlet); 8.26 (1H, singlet).

Mass Spectrum (m/z): 276 [(M+1)+], 193.

EXAMPLE 35

(2R*,3S*,4S*)-2-(4-chlorophenyl)-4-ethyl-3-methyl-2-[(1H-1,2,4-triazol-1-yl)methyl]oxetane, as an oil, in a yield of 8.0%.

Nuclear Magnetic Resonance Spectrum (CDCl3), δ ppm: 0.69 (3H, doublet, J=7.0 Hz); 0.79 (3H, triplet, J=7.5 Hz); 1.11-29 (1H, multiplet); 1.31-1.44 (1H, multiplet); 2.69 (1H, quintet, J=7.0 Hz); 4.29 (1H, doublet, J=14.9 Hz); 4.59 (1H, doublet, J=14.9 Hz); 7.31 (2H, doublet, J=8.7 Hz); 7.40 (2H, doublet, J=8.7 Hz); 7.97 (1H, singlet); 8.26 (1H, singlet).

Mass Spectrum (m/z): 292 [(M+1)+], 209.

EXAMPLE 36

3-t-Butyl-2-(4-fluorophenyl)-2-[(1,2,4-triazol-1-yl)methyl]oxetane 2.02 g (20 mmole) of triethylamine and 2.29 g (20 mmole) of methanesulfonyl chloride were added, whilst ice-cooling, to a solution of 1.54 g (5 mmole) of 2-(4-fluorophenyl)-5,5-dimethyl-1-(1H-1,2,4-triazol-1-yl)-2,4-hexanediol in 75 ml of methylene chloride, and the resulting mixture was stirred at the same temperature for 3 hours and then at room temperature for 1 hour. At the end of this time, the reaction mixture was poured into 80 ml of ice-water and extracted with 150 ml of methylene chloride. The extract was washed with water, dried over anhydrous sodium sulfate and concentrated by evaporation under reduced pressure. The residue was purified by column chromatography through silica gel, using a 6:5 by volume mixture of hexane and ethyl acetate as the eluent, to afford 113 mg (yield 7.8%) of the title compound, melting at 128° C.

Nuclear Magnetic Resonance Spectrum (CDCl3), δ ppm: 1.06 (9H, singlet); 2.28 (1H, doublet of doublets, J=12.1 & 4.30 Hz); 2.64 (1H, doublet of doublets, J=1.21 & 14.30 Hz); 4.92 (1H, doublet, J=14.5 Hz); 5.21 (1H, doublet, J=14.5 Hz); 4.97 (1H, doublet of doublets, J=1.21 & 12.1 Hz); 7.01-7.11 (4H, multiplet); 7.77 (1H, singlet); 7.80 (1H, singlet).

Mass Spectrum (m/z): 289 (M+), 207

EXAMPLE 37

3-t-Butyl-2-(4-chlorophenyl)-2-[(1H-1,2,4-triazol-1-yl)methyl]oxetane

Following a procedure similar to that described in Example 36, the title compound was obtained as an oil. The yield was 3.4%.

Nuclear Magnetic Resonance Spectrum (CDCl3), δ ppm: 1.10 (9H, singlet); 2.27 (1H, doublet of doublets, J=11.7 & 13.9 Hz); 2.62 (1H, broad doublet, J=13.9 Hz); 4.96 (1H, doublet, J=12.5 Hz); 5.19 (1H, doublet, J=12.5 Hz); 7.16 (2H, doublet, J=8.3 Hz); 7.30 (2H, doublet, J=8.3 Hz); 7.81 (1H, broad singlet); 7.86 (1H, broad singlet).

Mass Spectrum (m/z): 305 (M+), 223.

EXAMPLE 38

2-(4-Chlorophenyl)-4-isopropyl-2-[(1H-1,2,4-triazol-1-yl)methyl]oxetane

Following a procedure similar to that described in Example 36, but using 700 mg (2.26 mmole) of 2-(4-chlorophenyl)-5-methyl-1-(1H-1,2,4-triazol-1-yl)-2,4-hexanediol, there were obtained two stereoisomers at the 4-position of the title compound.

Yield of compound (A), having the lesser polarity, was 53.5 mg (8.1%) and that of a compound (B), having the greater polarity, was 28.9 mg (4.4%).

Compound (A): an oily substance

Nuclear Magnetic Resonance Spectrum (CDCl$_3$), δ ppm: 1.06 (3H, doublet, J=6.8 Hz); 1.07 (3H, doublet, J=6.8 Hz); 1.96 (1H, septet, J=6.8 Hz); 2.27 (1H, doublet of doublets, J=1 2.1 & 14.1 Hz); 2.65 (1H, doublet of doublets, J=1.8 & 14.1 Hz); 4.99 (1H, doublet, J=14.5 Hz); 5.16 (1H, doublet, J=14.5 Hz); 4.99–5.06 (1H, multiplet); 7.04 (2H, doublet, J=8.7 Hz); 7.29 (2H, doublet, J=8.7 Hz); 7.81 (1H, singlet); 7.88 (1H, singlet).

Mass Spectrum (m/z): 291 (M+), 209.

Compound (B):

Nuclear Magnetic Resonance Spectrum (CDCl$_3$), δ ppm: 1.00 (3H, doublet, J=7.3 Hz); 1.02 (3H, doublet, J=7.3 Hz); 1.88–2.00 (1H, multiplet); 2.77 (1H, doublet of doublets, J=3.2 & 14.5 Hz); 2.94 (1H, doublet of doublets, J=12.1 & 14.5 Hz); 3.94 (1H, doubled doublet of doublets, J=3.2, 6.4 & 12.1 Hz); 4.45 (1H, doublet, J=14.3 Hz); 4.70 (1H, doublet, J=14.3 Hz); 7.14 (2H, doublet, J=8.7 Hz); 7.32 (2H, doublet, J=8.7 Hz); 7.69 (1H, singlet); 7.92 (1H, singlet).

Mass Spectrum (m/z): 291 (M+), 209.

EXAMPLE 39

3,3,4-Trimethyl-2-phenyl-2-(1H-1,2,4-triazol-1-yl)methyloxetane 4.0 ml (37.64 mmole) of 2-methyl-2-butene were added to a solution of 1.1 g (5.88 mmole) of 2-(1H-1,2,4-triazol-1-yl)acetophenone in 15 ml of a 2:1 by volume mixture of acetonitrile and benzene. The mixture was then irradiated with a 450 watt medium pressure mercury-arc lamp (Hannovea Co., Inc.) for 15 hours. At the end of this time, the reaction mixture was concentrated by evaporation under reduced pressure, and the residue was subjected to column chromatography through silica gel, using a 1:1 by volume mixture of hexane and ethyl acetate as the eluent, to afford 409.7 mg (yield 27%) of the title compound, melting at 102° C.

Nuclear Magnetic Resonance Spectrum (CDCl$_3$), δ ppm: 0.76 (3H, singlet); 1.26 (3H, doublet, J=6.4 Hz); 1.36 (3H, singlet); 4.64 (1H, doublet, J=14.1 Hz); 4.82 (1H, quartet, J=6.4 Hz); 5.10 (1H, doublet, J=14.1 Hz); 7.1–7.3 (5H, broad multiplet); 7.65 (1H, singlet); 7.76 (1H, singlet).

Mass Spectrum (m/z): 258 [(M+1)+], 188, 175, 152, 144, 129.

EXAMPLES 40 to 44

Using a procedure similar to that described in Example 39, the following compounds were synthesized.

EXAMPLE 40

2-(4-Isopropylphenyl)-2-(1H-1,2,4-triazol-1-yl)methyl-3,3,4-trimethyloxetane, melting at 53°-60° C., in a yield of 4.4%.

Nuclear Magnetic Resonance Spectrum (CDCl$_3$), δ ppm: 0.76 (3H, singlet); 1.20 (6H, doublet, J=6.85 Hz); 1.26 (3H, doublet, J=6.45 Hz); 1.35 (3H, singlet); 2.84 (1H, septet, J=6.85 Hz); 4.62 (1H, doublet, J=14.1 Hz); 4.81 (1H, quartet, J=6.45 Hz); 5.10 (1H, doublet, J=14.1 Hz); 6.96–7.12 (4H, broad multiplet); 7.69 (1H, singlet); 7.74 (1H, singlet).

Mass Spectrum (m/z): 299 (M+), 230, 217.

EXAMPLE 41

2-(4-Methoxyphenyl)-2-(1H-1,2,4-triazol-1-yl)methyl-3,3,4-trimethyloxetane, as an oil, in a yield of 2.5%.

Nuclear Magnetic Resonance Spectrum (CDCl$_3$), δ ppm: 0.75 (3H, singlet); 1.26 (3H, doublet, J=6.44 Hz); 1.34 (3H, singlet); 3.76 (3H, singlet); 4.63 (1H, J=14.1 Hz); 4.81 (1H, quartet, J=6.44 Hz); 5.09 (1H, doublet, J=14.1 Hz); 6.80 (2H, doublet, J=8.87 Hz); 6.94–7.03 (2H, broad); 7.69 (1H, singlet); 7.83 (1H, singlet).

Mass Spectrum (m/z): 287 (M+), 218, 205, 135.

EXAMPLE 42

2-(2,4-Dichlorophenyl)-2-(1H-1,2,4-triazol-1-yl)methyl-3,3,4-trimethyloxetane, melting at 85°-104° C., in a yield of 3.2%.

Nuclear Magnetic Resonance Spectrum (CDCl$_3$), δ ppm: 0.92 (3H, singlet); 1.24 (3H, doublet, J=6.45 Hz); 1.44 (3H, singlet); 4.81 (1H, quartet, J=6.45 Hz); 5.00 (1H, doublet, J=14.3 Hz); 5.26 (1H, doublet, J=14.3 Hz); 7.06 (1H, doublet of doublets, J=2 02 & 8.86 Hz); 7.16 (1H, doublet, J=8.86 Hz); 7.32 (1H, doublet, J=2.02 Hz); 7.63 (1H, singlet); 7.94 (1H, singlet).

Mass Spectrum (m/z): 325 (M+), 312, 243, 175.

EXAMPLE 43

2-(4-Fluorophenyl)-2-(1H-1,2,4-triazol-1-yl)methyl-3,3,4-trimethyloxetane, melting at 108° C., in a yield of 15%.

Nuclear Magnetic Resonance Spectrum (CDCl$_3$), δ ppm: 0.74 (3H, singlet); 1.26 (3H, doublet, J=6.45 Hz); 1.36 (3H, singlet); 4.65 (1H, doublet, J=14.1 Hz); 4.83 (1H, quartet, J=6.45 Hz); 5.08 (1H, doublet, J=14.1 Hz); 6.92–7.07 (4H, broad multiplet); 7.67 (1H, singlet); 7.90 (1H, singlet).

Mass Spectrum (m/z): 276 (M+), 206, 147.

EXAMPLE 44

2-(4-Chlorophenyl)-2-(1H-1,2,4-triazol-1-yl)methyl-3,3,4-trimethyloxetane, melting at 111°-114° C., in a yield of 2%.

Nuclear Magnetic Resonance Spectrum (CDCl$_3$), δ ppm: 0.72 (3H, singlet); 1.24 (3H, doublet, J=6.35 Hz); 1.33 (3H, singlet); 4.62 (1H, doublet, J=14.2 Hz); 4.80 (1H, quartet, J=6.35 Hz); 5.06 (1H, doublet, J=14.2 Hz); 6.8–7.24 (4H, broad multiplet); 7.65 (1H, singlet); 7.91 (1H, singlet).

Mass Spectrum (m/z): 292 (M+), 279, 222, 209.

EXAMPLE 45

2-(2,4-Difluorophenyl)-3,3-dimethyl-2-[(1H-1,2,4-triazol-1-yl)methyl]oxetane

2-Methylpropene was bubbled into 6 ml of benzene at 0° C. until there was about a 25% increase in its volume. 6 ml of acetonitrile and 695.2 mg (3.115 mmole) of 2',4'-difluoro-2-(1H-1,2,4-triazol-1-yl)acetophenone were then added to the solution and the resulting mixture was irradiated with a 450 watt medium pressure mercury-arc lamp (Hannovea Co., Inc.) at 15° C. for 15 hours. At the end of this time, the reaction mixture was concentrated by evaporation under reduced pressure, and then the residue was subjected to column chromatography through silica gel to afford 450 mg of a mixture of the title compound with unreacted starting material. This mixture was dissolved in 5 ml of methanol, and 200 mg (5.27 mmole) of sodium borohydride was added at 0° C.

to the resulting solution, after which the mixture was stirred at the same temperature for 3 hours. At the end of this time, the reaction mixture was diluted with water and extracted with ethyl acetate. The organic layer was then dried over anhydrous magnesium sulfate and concentrated by evaporation under reduced pressure, to give a pale yellow residue. This residue was subjected to column chromatography through silica gel, using a 1:1 by volume mixture of hexane and ethyl acetate as the eluent, to afford 197.1 mg (0.706 mmole, yield 23%) of the title compound, melting at 76°–78° C.

The product was identical to the compound obtained as described in Example 25 in all respects.

EXAMPLE 46

2-(4-Fluorophenyl)-3,3-dimethyl-2-[(1H-1,2,4-triazol-1-yl)methyl]oxetane

This illustrates the synthesis of the title compound by photoreaction.

Following a procedure similar to that described in Example 39, but using 2-methylpropene and 4'-fluoro-2-(1H-1,2,4-triazol-1-yl)acetophenone, the title compound, melting at 110° C., was obtained in a 2% yield.

Nuclear Magnetic Resonance Spectrum (CDCl$_3$), δ ppm: 0.92 (3H, singlet); 1.43 (3H, singlet); 4.20 (1H, doublet, J=5.6 Hz); 4.58 (1H, doublet, J=5.6 Hz); 4.64 (1H, doublet, J=14.1 Hz); 5.06 (1H, doublet, J=14.1 Hz); 6.97 (2H, triplet, J=8.86 Hz); 7.00–7.09 (2H, broad multiplet); 7.68 (1H, singlet); 7.99 (1H, singlet).

Mass Spectrum (m/z): 261 (M+), 179, 123.

EXAMPLE 47

8-(2,4-Difluorophenyl)-7-oxa-8-(1H-1,2,4-triazol-1-yl)methyl-bicyclo[4.2.0]octane Following a procedure similar to that described in Example 39, but using cyclohexene and 2',4'-difluoro-2-(1H-1,2,4-triazol-1-yl)acetophenone, 1:1 mixture of stereoisomers at the 8-position of the title compound was obtained as a gum in a 31% yield.

Nuclear Magnetic Resonance Spectrum (CDCl$_3$), δ ppm: 1.0–2.2 (broad multiplet); 2.64 (broad doublet of triplets, J=4.1 Hz); 3.03 (quartet, J=7.15 Hz); 4.52 (doublet, J=14.5 Hz); 4.60 (multiplet); 4.70 (doublet, J=14.5 Hz); 4.89 (doublet, J=14.5 Hz); 5.11 (doublet, J=14.5 Hz); 6.65–6.96 (multiplet); 7.31 (doubled doublet of doublets, J=1.61, 8.05 & 8.05 Hz); 8.17 (singlet); 7.95 (singlet); 7.81 (singlet); 7.81 (singlet).

EXAMPLE 48

2-(2,4'-Difluorophenyl)-3,3,4,4-tetramethyl-2-[(1H-1,2,4-triazol-1-yl)methyl]oxetane Following a procedure similar to that described in Example 39, but using 2,3-dimethyl-2-butene and 2',4'-difluoro-2-(1H-1,2,4-triazol-1-yl)acetophenone, 85 mg (yield 15%) of the title compound, melting at 100°–101° C., were obtained.

Nuclear Magnetic Resonance Spectrum (CDCl$_3$), δ ppm: 0.93 (3H, doublet, J=1.61 Hz); 1.27 (3H, singlet); 1.42 (3H, singlet); 1.58 (3H, singlet); 4.84 (1H, doublet of doublets, J=1.61, 14.10 Hz); 4.90 (1H, doublet, J=14.10 Hz); 6.65–6.82 (2H, multiplet); 7.20 (1H, doubled doublet of doublets, J=2.01, 9.01 & 9.01 Hz); 7.60 (1H, singlet); 7.91 (1H, singlet).

Mass Spectrum (m/z): 307 (M+), 294, 279, 224, 205, 167, 149, 141.

EXAMPLE 49

(2R*,4R*)-2-(4-Fluorophenyl)-3,4-dimethyl-2-[(1H-1,2,4-triazol-1-yl)methyl]oxetane Following a procedure similar to that described in Example 39, but using cis-2-butene and 950 mg (5.68 mmole) of 4'-fluoro-2-(1H-1,2,4-triazol-1-yl)-acetophenone, 80 mg (yield 5.3%) of a 1:1 mixture of stereoisomers at the 3-position of the title compound were obtained, in the form of oil.

Nuclear Magnetic Resonance Spectrum (CDCl$_3$), δ ppm: 0.69 (doublet, J=7.25 Hz); 1.16 (doublet, J=6.45 Hz); 1.37 (doublet, J=6.45 Hz); 2.79 (quintet, J=7.25 Hz); 3.15 (quintet, J=7.25 Hz); 4.39 (doublet, 14.50 Hz); 4.50 (multiplet); 4.60 (multiplet); 4.59 (doublet, J=14.1 Hz); 4.73 (doublet, J=14.50 Hz); 4.92 (doublet J=14.1 Hz); 6.91–7.15 (multiplet); 7.21–7.32 (multiplet); 7.76 (singlet); 7.94 (singlet); 7.98 (singlet); 8.27 (singlet).

Mass Spectrum (m/z): 261 (M+), 206, 179, 148, 133, 123.

EXAMPLE 50

2-(4-Methylphenyl)-2-(1H-1,2,4-triazol-1-yl)methyl]oxetane 0.98 g (25.5 mmole) of sodium hydride (as a 60% w/w dispersion in mineral oil) was added to 20 ml of dimethyl sulfoxide, and the resulting mixture was stirred at 80° C. for 1hour. At the end of this time, 5.62 g (25.5 mmole) of trimethylsulfoxonium iodide were added, whilst ice-cooling, after which the mixture was allowed to heat up to room temperature. It was then stirred for 30 minutes, and a solution of 2.2 g (11.6 mmole) of 4'-methyl-2-(1H-1,2,4-triazol-1-yl)-acetophenone in 5 ml of dimethyl sulfoxide was added; the mixture was then stirred at 50° C. for 6 hours. After the reaction mixture had been cooled, it was poured into 20 ml of ice-water and extracted with 200 ml of ethyl acetate. The extract was then washed twice, each time with 100 ml of a saturated aqueous solution of sodium chloride, after which it was dried over anhydrous sodium sulfate and concentrated by evaporation under reduced pressure, to afford 2.7 g of an oily substance. This oil was subjected to column chromatography through silica gel, using a 1:1 by volume mixture of hexane and ethyl acetate as the eluent, to afford 2.3 g (yield 86.3%) of the title compound as an oil.

Nuclear Magnetic Resonance Spectrum (CDCl$_3$), δ ppm: 2.37 (3H, singlet); 2.6–2.7 (1H, multiplet); 2.91–2.98 (1H, multiplet); 4.02–4.10 (1H, multiplet); 4.29 (1H, doublet, J=14.7 Hz); 4.52 (1H, doublet, J=14.7 Hz); 4.38–4.46 (1H, multiplet); 7.22 (4H, singlet); 7.98 (1H, singlet); 8.22 (1H, singlet).

Mass Spectrum (m/z): 229 (M+), 214, 198, 184, 172, 159, 148, 119.

Infrared Absorption Spectrum (liquid film), λ$_{max}$ cm$^{-1}$: 3140, 2980, 2950, 1505, 1271.

EXAMPLES 51 TO 57

Using a procedure similar to that described in Example 50, the following compounds were synthesized.

EXAMPLE 51

2-(4-Chlorophenyl)-2-[(1H-1,2,4-triazol-1-yl)methyl]-oxetane, melting at 74°–75° C., in a yield of 61%.

Nuclear Magnetic Resonance Spectrum (CDCl$_3$), δ ppm: 2.62–2.75 (1H, multiplet); 2.95–3.05 (1H, multiplet); 4.06–4 14 (1H, multiplet); 4.30 (1H, doublet, J=14.5 Hz); 4.39–4.49 (1H, multiplet); 4.53 (1H, doublet, J=14.5 Hz); 7.27 (2H, doublet, J=8.46 Hz); 7.38 (2H, doublet, J=8.46 Hz); 7.98 (1H, singlet); 8.24 (1H, singlet).

Mass Spectrum (m/z): 249 (M+), 169, 139.

EXAMPLE 52

2-(2,4-Difluorophenyl)-2-[(1H-1,2,4-triazol-1-yl)methyl]-oxetane, as an oil, in a yield of 45%

Nuclear Magnetic Resonance Spectrum (CDCl$_3$), δ ppm: 2.66–2.77 (1H, multiplet); 2.93–3.04 (1H, multiplet); 4.15–4.23 (1H, multiplet); 4.34 (1H, doublet, J=14.9 Hz); 4.43–4.52 (1H, multiplet); 4.73 (1H, doublet, J=14.9 Hz); 6.81–6.93 (2H, multiplet); 7.39–7.48 (1H, multiplet); 7.94 (1H, singlet); 8.27 (1H, singlet).

Mass Spectrum (m/z): 251 (M+), 170, 141.

EXAMPLE 53

2-(4-Isopropylphenyl)-2-[(1H-1,2,4-triazol-1-yl)methyl]-oxetane, as an oil, in a yield of 87%.

Nuclear Magnetic Resonance Spectrum (CDCl$_3$), δ ppm: 1.27 (6H, doublet, J=7.3 Hz); 2.17–2.72 (1H, multiplet); 2.90–3.01 (2H, multiplet); 4.02–4.07 (1H, multiplet); 4.29 (1H, doublet, J=14.7 Hz); 4.38–4.47 (1H, multiplet); 4.52 (1H, doublet, J=14.7 Hz); 7.27 (4H, singlet); 7.99 (1H, singlet); 8.25 (1H, singlet).

Mass Spectrum (m/z): 257 (M+), 175, 147.

EXAMPLE 54

2-(4-Trifluoromethylphenyl)-2-[(1H-1,2,4-triazol-1-yl)-methyl]oxetane, as an oil, in a yield of 42%.

Nuclear Magnetic Resonance Spectrum (CDCl$_3$), δ ppm: 2.66–2.72 (1H, multiplet); 3.00–3.11 (1H, multiplet); 4.07–4.15 (1H, multiplet); 4.32 (1H, doublet, J=14.9 Hz); 4.40–4.48 (1H, multiplet); 4.57 (1H, doublet, J=14.9 Hz); 7.47 (2H, doublet, J=8.1 Hz); 7.68 (2H, doublet, J=8.1 Hz); 7.99 (1H, singlet); 8.27 (1H, singlet).

Mass Spectrum (m/z): 283 (M+), 201, 173.

EXAMPLE 55

2-(4-Fluorophenyl)-2-[(1H-1,2,4-triazol-1-yl)methyl]-oxetane, melting at 65°–66° C., in a yield of 55%.

Nuclear Magnetic Resonance Spectrum (CDCl$_3$), δ ppm: 2.61–2.81 (1H, multiplet); 2.94–3.04 (1H, multiplet); 4.06–4.16 (1H, multiplet); 4.30 (1H, doublet, J=14.7 Hz); 4.40–4.48 (1H, multiplet); 4.53 (1H, doublet, J=14.7 Hz); 7.06–7.12 (2H, multiplet); 7.27–7.33 (2H, multiplet); 7.99 (1H, singlet); 8.25 (1H, singlet).

Mass Spectrum (m/z): 233 (M+), 151, 123.

EXAMPLE 56

2-(4-Methoxyphenyl)-2-(1H-1,2,4-triazol-1-yl)methyl]-oxetane, melting at 66°–67° C., in a yield of 46%.

Nuclear Magnetic Resonance Spectrum (CDCl$_3$), δ ppm: 2.61–2.71 (1H, multiplet); 2.90–3.02 (1H, multiplet); 3.82 (3H, singlet); 4.04–4.14 (1H, multiplet); 4.30 (1H, doublet, J=14.7 Hz); 4.44–4.47 (1H, multiplet); 4.51 (1H, doublet, J=14.7 Hz); 6.93 (2H, doublet, J=8.86 Hz); 7.25 (2H, doublet, J=8.86 Hz); 7.98 (1H, singlet); 8.21 (1H, singlet).

Mass Spectrum (m/z): 245 (M+), 163, 135.

EXAMPLE 57

2-(4-Chloro-2-fluoromethylphenyl)-2-[(1H-1,2,4-triazol-1-yl)methyl]oxetane, as an oil, in a yield of 59%.

Nuclear Magnetic Resonance Spectrum (CDCl$_3$), δ ppm: 2.66–2 77 (1H, multiplet); 2.94–3.04 (1H, multiplet); 4.08–4.23 (1H, multiplet); 4.34 (1H, doublet, J=14.7 Hz); 4.39–4.51 (1H, multiplet); 4.73 (1H, doublet, J=14.7 Hz); 7.08–7.18 (2H, multiplet); 7.37–7.43 (1H, multiplet); 7.94 (1H. singlet); 8.27 (1H, singlet).

Mass Spectrum (m/z): 245 (M+), 163, 135.

EXAMPLE 58

2-(4-Methylphenyl)-2-[1-(1,2,4-triazol-1-yl)-ethyl]oxetane

Following a procedure similar to that described in Example 50, but using 4'-methyl-2-(1H-1,2,4-triazol-1-yl)propiophenone, an approximately 2:1 mixture of stereoisomers (having different configurations of the triazole group) of the title compound was obtained as an oil, in a yield of 49.3%.

Nuclear Magnetic Resonance Spectrum (CDCl$_3$), δ ppm: 1.33 (doublet, J=7.25 Hz); 2.37 (singlet); 2.44–2.53 (multiplet); 2.70–2.80 (multiplet); 3.98–4.06 (multiplet); 4.37–4.47 (multiplet); 4.74 (quartet, J=7.25 Hz); 7.20 (singlet); 7.99 (singlet); 8.34 (singlet).

Mass Spectrum (m/z): 243 (M+), 228, 213, 147, 119.

EXAMPLE 59

2-(2,4-Difluorophenyl)-2-[(1H-1,2,4-triazol-1-yl)methyl]oxetane 101 mg (4.2 mmole) of sodium hydride (as a 60% w/w dispersion in mineral oil) were added to 10 ml of dimethyl sulfoxide, and the resulting mixture was stirred at 80° C. for 30 minutes. At the end of this time, the mixture was cooled, 928 mg (4.2 mmole) of trimethylsulfoxonium iodide were added thereto and the reaction temperature was allowed to rise to room temperature. The mixture was then stirred for 30 minutes, after which 501 mg (2.11 mmole) of 2-(2,4-difluorophenyl)-2-[(1H-1,2,4-triazol-1-yl)methyl]-oxirane was added, and the mixture was stirred at 50° C. for a further 16 hours. At the end of this time, the reaction mixture was cooled, poured into 50 ml of ice-water and extracted with 100 ml of ethyl acetate. The extract was washed with a saturated aqueous solution of sodium chloride, dried over anhydrous sodium sulfate and concentrated by evaporation under reduced pressure. The residue was subjected to column chromatography through silica gel, eluted with a 2:3 by volume mixture of hexane and ethyl acetate, to afford 238 mg (yield 45%.) of the title compound as an oil.

The product was identical with the compound obtained as described in Example 52 in all respects.

EXAMPLE 60

5-Oxa-4-phenyl-4-[(1,2,4-triazol-1-yl)-methyl]spiro[2.3-]hexane 33.2 mg (0,496 mmole) of sodium hydride (as a 60% w/w dispersion in mineral oil) was added, whilst ice-cooling, to a solution of 69.8 mg (0.207 mmole) of 1-[1-methanesulfonyloxymethyl)cyclopropan-1-yl]-1-phenyl-2-(1H-1,2,4-triazol-1-yl)ethanol in dimethylformamide, and the resulting mixture was stirred at room temperature for 2 hours. At the end of this time, the reaction mixture was poured into ice-water and extracted with ethyl acetate. The extract was washed with a saturated aqueous solution of sodium chloride, dried over anhydrous magnesium sulfate and concentrated by evaporation under reduced pressure. The resulting residue was subjected to column chromatography through silica gel, eluted with a 1:1 by volume mixture of hexane and ethyl acetate, to afford 5 mg (yield 9.9%) of the title compound as an oil.

Nuclear Magnetic Resonance Spectrum (CDCl$_3$), δ ppm: 0.3–0.9 (4H, multiplet); 4.37 (1H, doublet, J=5.46 Hz); 4.44 (1H, doublet, J=14.80 Hz); 4.54 (1H, doublet, J=5.46 Hz); 4.85 (1H, doublet, J=14.80 Hz); 7.19–7.41 (5H, multiplet); 7.88 (1H, singlet); 8.32 (1H, singlet).

Mass Spectrum (m/z): 242 (M+), 188, 172, 159.

EXAMPLE 61

(2R*,3S*,4S*)-2-(4-Chlorophenyl)-3,4-dimethyl-2-[(1H-1,2,4-triazol-1-yl)methyl]oxetane 28 mg (1.003 mmole) of sodium hydride (as a 60% w/w dispersion in mineral oil) was added, whilst ice-cooling, to a solution of 200 mg (0.59 mmole) of (2R*,3S*,4S*)-2-(4-chlorophenyl)-3-methyl-4-methanesulfonyloxy-1-(1H-1,2,4-triazol-1-yl)pentanol in 5 ml of dimethylformamide, and the resulting mixture was stirred for 1.5 hours. At the end of this time, the reaction mixture was treated in a similar manner to that described in Example 60, to afford 32.3 mg (yield 19.7%) of the title compound as an oil.

Nuclear Magnetic Resonance Spectrum (CDCl$_3$), δ ppm: 0.73 (3H, doublet, J=7.25 Hz); 1.06 (3H, doublet, J=6.04 Hz); 2.66 (1H, quintet, J=7.25 Hz); 4.26 (1H, multiplet); 4.31 (1H, doublet, J=14.9 Hz); 7.30 (2H, doublet, J=8.66 Hz); 7.40 (2H, doublet, J=8.66 Hz); 8.01 (1H, singlet); 8.38 (1H, singlet).

Mass Spectrum (m/z): 278 [(M+1)+], 222, 195, 139.

EXAMPLES 62 TO 66

Using a procedure similar to that described in Example 61, the following compounds were synthesized.

EXAMPLE 62

(2R*,3R*,4S*)-2-(4-Chlorophenyl)-3,4-dimethyl-2-[(1H-1,2,4-triazol-1-yl)methyl]oxetane, melting at 75°–118° C., in a yield of 8.0%.

Nuclear Magnetic Resonance Spectrum (CDCl$_3$), δ ppm: 1.39 (3H, doublet, J=6.04 Hz); 1.42 (3H, doublet, J=4.88 Hz); 3.14 (1H, quintet, J=7.66 Hz); 4.60 (1H, doublet, J=14.5 Hz); 4.74 (1H, doublet, J=14.5 Hz); 4.92 (1H, quintet, J=6.54 Hz); 7.10 (2H, doublet, J=8.46 Hz); 7.26 (2H, doublet, J=8.46 Hz); 7.83 (1H, singlet); 8.13 (1H, singlet).

Mass Spectrum (m/z): 277 (M ), 222, 195, 139.

EXAMPLE 63

(2R*,3R*,4R*)-2-(4-Chlorophenyl)-3,4-dimethyl-2-[(1H-1,2,4-triazol-1-yl)methyl]oxetane, melting at 113°–121° C., in a yield of 70%.

Nuclear Magnetic Resonance Spectrum (CDCl$_3$), δ ppm: 1.37 (3H, doublet, J=5.64 Hz); 1.38 (3H, doublet, J™7.65 Hz); 2.77 (1H, quintet, J=7.25 Hz); 4.51–4.64 (1H, multiplet); 4.59 (1H, doublet, J™14.3 Hz); 4.93 (1H, doublet, J=14.3 Hz); 7.08 (2H, doublet, J=8.46 Hz); 7.25 (2H, doublet, J=8.46 Hz); 7.78 (1H, singlet); 8.05 (1H, singlet).

Mass Spectrum (m/z): 278 [(M+1)], 222, 195, 139.

EXAMPLE 64

(2R*,3S*,4R*)-2-(4-Bromophenyl)-3,4-dimethyl-2-[(1H-1,2,4-triazol-1-yl)methyl]oxetane, as an oil, in a yield of 62.3%.

Nuclear Magnetic Resonance Spectrum (CDCl$_3$), δ ppm: 0.70 (3H, doublet, J=7.66 Hz); 1.16 (3H, doublet, J=6.45 Hz); 3.16 (1H, quintet, J=7.66 Hz); 4.38 (1H, doublet, J=14.5 Hz); 4.40–4.54 (1H, multiplet); 4.72 (1H, doublet, J=14.5 Hz); 7.19 (2H, doublet, J=8.66 Hz); 7.52 (2H, doublet, J=8.66 Hz); 7.95 (1H, singlet); 8.30 (1H, singlet).

Mass Spectrum (m/z): 322 [(M+1)+], 303, 266, 241, 185.

EXAMPLE 65

(2R*,3S*,4R*)-2-(4-Trifluoromethylphenyl)-3,4-dimethyl-2-[(1H-1,2,4-triazol-1-yl)methyl]oxetane, as an oil, in a yield of 46%.

Nuclear Magnetic Resonance Spectrum (CDCl$_3$), δ ppm: 0.71 (3H, doublet, J=7.7 Hz); 1.17 (3H, doublet, J=6.4 Hz); 3.23 (1H, quintet, J=7.7 Hz); 4.40 (1H, doublet, J=14.5 Hz); 4.43–4.48 (1H, multiplet); 4.75 (1H, doublet, J=14.5 Hz); 7.44 (2H, doublet, J=8.1 Hz); 7.65 (2H, doublet, J=8.1 Hz); 7.95 (1H, singlet); 8.30 (1H, singlet).

Mass Spectrum (m/z): 312 [(M+1)+], 229, 173.

EXAMPLE 66

(2R*,3R*)-2-(4-Chloro-2-fluoromethylphenyl)-3,4-dimethyl-2-[(1H-1,2,4-triazol-1-yl)methyl]oxetane, melting at 115°–116° C., in a yield of 93%.

Nuclear Magnetic Resonance Spectrum (CDCl$_3$), δ ppm: 1.30–1.41 (6H, multiplet); 2.72–2.84 (1H, multiplet); 4.54–4.8 (1H, multiplet); 4.65 (1H, doublet, J=13.31 Hz); 4.95 (1H, doublet, J=13.31 Hz); 6.98–7 38 (3H, multiplet); 7.72 (1H, singlet); 8.07 (1H, singlet).

Mass Spectrum (m/z): 296 [(M+1)+], 256, 240, 215, 159.

EXAMPLE 67

(2R*,3S*,4R*)-2-(4-Chlorophenyl)-3,4-dimethyl-2-[(1H-1,2,4-triazol-1-yl)methyl]oxetane 38 mg (0.950 mmole) of sodium hydride (as a 60% w/w dispersion in mineral oil) were added at 0° C. to a suspension of 107 mg (0.351 mmole) of 2-(4-chlorophenyl)-3,4-dimethyl-2-methanesulfonyloxymethyloxetane, 51.5 mg (0.746 mmole) of 1H-1,2,4-triazole and 45.6 mg (0.304 mmole) of sodium iodide in 10 ml of dimethylimidazolidinone, and the mixture was stirred at room temperature for 30 minutes and then at 90° C. for a further 12 hours. At the end of this time, an aqueous solution of sodium thiosulfate was added to the resulting mixture, which was then extracted with a 1:1 by volume mixture of ethyl acetate and hexane. The extract was washed with water, dried over anhydrous magnesium sulfate and concentrated by evaporation under reduced pressure. The resulting residue was subjected to column chromatography through silica gel, eluted with a 1:1 by volume mixture of hexane and ethyl acetate, to afford 76.3 mg (yield 78%) of the title compound.

The compound thus obtained was identical with the compound prepared as described in Example 20 in all respects.

EXAMPLE 68

(2R*,3S*,4R*)-2-(4-Chlorophenyl)-3,4-dimethyl-2-[(1H-1,2,4-triazol-1-yl)methyl]oxetane nitrate 0.19 ml of concentrated aqueous nitric acid (about 61%) was added to a solution of 300 mg (1.08 mmole) of (2R*,3S*,4R*)-2-(4-chlorophenyl)-3,4-dimethyl-2-[(1H-1,2,4-triazol-1-yl)methyl]oxetane (prepared as described in Example 20) in a mixture of 5 ml of diethyl ether and 1 ml of methanol. The resulting mixture was freed from the solvent by distillation under reduced pressure, and the resulting residue was mixed with a mixture of diethyl ether and hexane. The crystals which precipitated were collected by filtration, to give 351 mg (yield 95.4%) of the title compound, melting at 129°-142° C.

Elemental analysis:

Calculated for $C_{14}H_{17}ClN_4O_4$: C, 49.35%; H, 5.03%; Cl, 10.40%; N, 16.44%. Found: C, 49.28%; H, 5.15%; C:, 10.32%; N, 16.64%.

EXAMPLE 69

(2R*,3S*,4R*)-2-(4-Chlorophenyl)-3,4-dimethyl-2-[(1H-1,2,4-triazol-1-yl)methyl]oxetane oxalate A solution of 97.2 ml of oxalic acid in ethyl acetate was added dropwise to a solution of 300 mg (1.08 mmole) of 2R*, 3S*, 4R*)-2-(4-chlorophenyl)-3,4-dimethyl-2-[(1H-1,2,4-triazol-1-yl)methyl]oxetane (prepared as described in Example 20) in 5 ml of ethyl acetate, and the crystals which precipitated were collected by filtration. After drying, there were obtained 229 mg (yield 57.7%) of the title compound, melting at 135°-144° C.

Infrared Absorption Spectrum (KBr), $\lambda_{max}$ cm$^{-1}$: 3424, 3119, 2908, 2516, 1967, 1731, 1610.

Nuclear Magnetic Resonance Spectrum (hexadeuterated dimethyl sulfoxide), δ ppm: 0.61 (3H, doublet, J=7.25 Hz); 1.09 (3H, doublet, J=6.45 Hz); 3.18 (1H, quintet, J=7.65 Hz); 3.37 (broad singlet); 4.51 (1H, triplet, J=7.25 Hz); 4.60 (1H, doublet, J=14.5 Hz); 4.89 (1H, doublet, J=14.5 Hz); 7.34 (2H, doublet, J=8.86 Hz); 7.41 (1H, doublet, J=8.86 Hz); 7.88 (1H, singlet); 8.34 (1H, singlet).

EXAMPLE 70

2-(2,4-Dichlorophenyl)-3,3,4-trimethyl-2-(1H-1,2,4-triazol-1-yl)methyloxetane 84 mg (2.1 mmole) of sodium hydride (as a 60% w/w suspension in mineral oil) were added to a solution of 400 mg (0.95 mmole) of 2-(2,4-dichlorophenyl)-3,3-dimethyl-4-mesyloxy-1-(1H-1,2,4-triazol-1-yl)-2-pentanol in 5 ml of N,N-dimethylformamide, and then the mixture was stirred at 90° C. for 2 hours. At the end of this time, the reaction mixture was allowed to cool, after which it was poured into ice-water and extracted with ethyl acetate. The extract was washed with water and dried over anhydrous sodium sulfate, after which the solvent was removed by distillation under reduced pressure. The residue was washed with hexane to give 262.4 mg of a crude product, which was then purified by column chromatography through silica gel, eluted with a 1:1 by volume mixture of hexane and ethyl acetate, to afford 220.7 mg (yield 71.4%) of the title compound, melting at 118°-125° C. This compound is a steroisomer, isomeric at the C4 position, of the compound obtained in Example 42.

Mass Spectrum (m/z): 328, 326, 290, 256, 243, 173.

Nuclear Magnetic Resonance Spectrum (CDCl$_3$), δ ppm: 1.06 (3H, singlet); 1.42 (3H, singlet); 1.49 (3H, doublet, J=6.3 Hz); 4.36 (1H, quartet, J=6.3 Hz); 4.83 (1H, doublet, J=14.2 Hz); 5.36 (1H, doublet, J=14.2 Hz); 7.10 (1H, doublet of doublets, J=2.2 & 8.4 Hz); 7.28 (1H, doublet, J=8.4 Hz); 7.35 (1H, doublet, J=2.2 Hz); 7.63 (1H, singlet); 7.99 (1H, singlet).

EXAMPLE 71

(2R*,3S*,4R*)-2-(4-Chlorophenyl) 3,4-dimethyl-2-[(1H)-1,2,4-triazol-1-yl)methyl]oxetane 26 mg (0.38 mmole) of 1H-1,2,4-triazole and 26 mg (0.19 mmole) of potassium carbonate were added to a solution of 245 mg (1mmole) of 2-chloromethyl-2-(4-chlorophenyl)-3,4-dimethyloxetane (a 3:1 mixture of the 4S* and 4R* isomers), and then the mixture was stirred at 130° C. for 5 hours. At the end of this time, the reaction mixture was allowed to cool, after which it was poured into ice-water and extracted with ethyl acetate. The extract was washed with a saturated aqueous solution of ammonium chloride and dried over anhydrous sodium sulfate, after which the solvent was removed by distillation under reduced pressure to leave 260 mg of a residue. This residue was then purified by column chromatography through silica gel to afford 56.2 mg (yield 81%) of the title compound, melting at 111-118° C.

Mass Spectrum (m/z): 278 [(M+1)+], 222, 195, 141.

EXAMPLES 72 TO 75

Following a procedure similar to that described in Example 4, the following compounds were prepared.

EXAMPLE 72

(2R*,3S*,4S*)-2-(2,4-Difluorophenyl)-4-isopropyl-3-methyl-2-[(1H-1,2,4-triazol-1-yl)methyl]oxetane hydrogen oxalate, melting at 140°-145° C., in a yield of 5%.

Nuclear Magnetic Resonance Spectrum (CDCl$_3$) δ ppm: 0.69 (3H, doublet, J=7 Hz); 0.88 (3H, doublet of doublets, J=2.5 & 7 Hz); 0.90 (3H, doublet, J=7 Hz); 1.25 (1H, multiplet); 2.79 (1H, multiplet); 3.61 (1H, doublet of doublets, J=7.5 & 9.5 Hz); 4.40 (1H, doublet, J=14.5 Hz); 4.78 (1H, doublet, J=14.5 Hz); 6.8-7.0 (2H, multiplet); 7.60 (1H, triplet of doublets, J=7 & 9 Hz); 7.87 (1H, singlet); 8.19 (1H, singlet).

EXAMPLE 73

(2R*,3R*,4S*)-2-(2,4-Difluorophenyl)-4-iscpropyl-3-methyl-2-[(1H-1,2,4-triazol-1-yl)methyl]oxetane hydrogen oxalate, melting at 151°-154° C., in a yield of 5%.

Nuclear Magnetic Resonance Spectrum (CDCl$_3$) δ ppm: 0.81 (3H, doublet, J=6.5 Hz); 1.02 (3H, doublet, J=6.5 Hz); 1.47 (3H, doublet, J=6.5 Hz); 2.29 (1H, multiplet); 3.19 (1H, multiplet); 4.17 (1H, doublet of doublets, J=8.5 & 10.5 Hz); 4.65 (1H, doublet, J=13 Hz); 4.92 (1H, doublet, J=13 Hz); 6.7-7.2 (3H, multiplet); 7.52 (1H, singlet); 8.13 (1H, singlet).

EXAMPLE 74

(2R*,3R*,4R*)-2-(2,4-Difluorophenyl)-4-isopropyl-3-methyl-2-[(1H-1,2,4-triazol-1-yl)methyl]oxetane, as an oil, in a yield of 35%.

Nuclear Magnetic Resonance Spectrum (CDCl$_3$) δ ppm: 0.77 (3H, doublet, J=7 Hz); 0.93 (3H, doublet, J=7 Hz); 1.40 (3H, doublet of doublets, J=1 & 7.5 Hz);

1.76 (1H, multiplet); 2.84 (1H, multiplet); 4.09 (1H, doublet of doublets, J=7 & 8 Hz); 4.67 (1H, doublet of doublets, J=1.5 & 14 Hz); 4.90 (1H, doublet, J=14 Hz); 6.6–6.8 (2H, multiplet); 7.07 (1H, triplet of doublets, J=6.5 & 8.5 Hz); 7.66 (1H, singlet); 8.03 (1H, singlet).

EXAMPLE 75

(2R*,3S*,4R*)-3,4-Dimethyl-2-phenyl-2-[(1H-1,2,4-triazol-1-yl)methyl]oxetane, as an oil, in a yield of 27%.

Nuclear Magnetic Resonance Spectrum (CDCl₃) δ ppm: 0.61 (3H, doublet, J=7.4 Hz); 1.08 (3H, doublet, J=6.5 Hz); 3.09 (1H, multiplet); 4.28 (1H, doublet, J=14.7 Hz); 4.32 (1H, multiplet); 4.67 (1H, doublet, J=14.7 Hz); 7.21–7.34 (5H, multiplet); 7.85 (1H, singlet); 8.15 (1H, singlet).

Mass Spectrum (m/z): 244 (M+1)⁺, 227, 188, 161.

EXAMPLE 76

(2R*,3S*,4R*)-2-(4-Fluorophenyl)-3,4-dimethyl-2-[(1H)-1,2,4-triazol-1-yl)methyl]oxetane Following a procedure similar to that described in Example 71, 110 mg (yield 38.3%) of the title compound were prepared as an oil.

Nuclear Magnetic Resonance Spectrum (CDCl₃), δ ppm: 0.70 (3H, doublet, J=7.65 Hz); 1.17 (3H, doublet, J=6.44 Hz); 3.15 (1H, quintet, J=7.56 Hz); 4.38 (1H, doublet, J=14.51 Hz); 4.39–4.52 (1H, multiplet); 4.73 (1H, doublet, J=14.51 Hz); 7.08 (2H, triplet, J=8.66 Hz); 7.22–7.32 (2H, multiplet); 7.95 (1H, singlet); 8.30 (1H, singlet).

Mass Spectrum (m/z):
262 (M+1)⁺, 244, 218, 206, 179.

PREPARATION 1

(3S*,4R*)-4-(2,4-Difluorophenyl)-3-methyl-5-(1H-1,2,4-triazol-1-yl)-1,4-pentanediol and
(2R*,3S*)-2-(2,4-difluorophenyl)-3-methyl-1-(1H-1,2,4-triazol-1-yl)-2,4-pentanediol 2.2 ml (4.4 mmole) of a 2M solution of a boranedimethyl sulfide complex in tetrahydrofuran were added, whilst ice-cooling and stirring, to a solution of 200 mg (0.72 mmole) of (2R*,3S*)-2-(2,4-difluorophenyl)-3-methyl-1-(1H-1,2,4-triazol-1-yl)-4-penten-2-ol (which was synthesized following the procedure described in Japanese Patent Provisional Publication No. Sho 60-36468) in 5 ml tetrahydrofuran. The mixture was allowed to warm to room temperature, after which it was stirred at that temperature for 15 minutes and then at 50° C. for 20 minutes. At the end of this time, it was again ice-cooled and 1 ml of a 15% w/v aqueous solution of sodium hydroxide and 1 ml of a 30% w/v aqueous solution of hydrogen peroxide were added thereto. The reaction mixture was then stirrred at room temperature for 30 minutes and then at 50°–60° C. for 2 hours, after which it was diluted with ethyl acetate and then washed with a saturated aqueous solution of sodium chloride. After it had been dried, the mixture was freed from the solvent by distillation under reduced pressure. The resulting oily residue was subjected to column chromatography through silica gel using mixtures of ethyl acetate and hexane ranging 5:1 to 10:1 by volume as the eluent, to afford 30 mg of the second-mentioned title compound as an oil. Nuclear Magnetic Resonance analysis showed the structure of the compound to be approximately a 1:1mixture of isomers A and B at the C₄ position.

Isomer A: (main peaks)
Nuclear Magnetic Resonance Spectrum (CDCl₃), δ ppm: 0.80 (3H, doublet of doublets, J=7 & 3.5 Hz); 1.18 (3H, doublet, J=6 Hz); 4.90 (2H, singlet); 5.97 (1H, singlet); 7.79 (1H, singlet); 8.05 (1H, singlet).

Isomer B: (main peaks)
Nuclear Magnetic Resonance Spectrum (CDCl₃), δ ppm: 0.76 (3H, doublet of doublets, J=7 & 1.5 Hz); 1.27 (3H, doublet, J=6 Hz); 5.47 (1H, singlet); 7.70 (1H, singlet); 7.93 (1H, singlet).

The column was then eluted, in turn, with ethyl acetate and with 1% by volume methanol in ethyl acetate to afford 139 mg of the first-mentioned title compound, which was recrystallized from a mixture of ethyl actate and hexane to give a pure specimen, melting at 121°–122° C.

Nuclear Magnetic Resonance Spectrum (CDCl₃), δ ppm: 0.78 (3H, doublet of doublets, J=7 & 1Hz); 1.6–2.0 (2H, multiplet); 2.4 (1H, multiplet); 3.3–4.0 (3H, multiplet); 4.62 (1H, doublet, J=14 Hz); 4.93 (1H, doublet of doublets, J=14 & 1 Hz); 5.52 (1H, broad); 6.5–7.0 (2H, multiplet); 7.43 (1H, triplet of doublets, J=9 & 7 Hz); 7.73 (1H, singlet); 7.97 (1H, singlet).

PREPARATION 2

(2R*,3S*,4S*)-2-(2,4-Difluorophenyl)-4-(methanesulfonyloxy)-3-methyl-1-(1H-1,2,4-triazol-1-yl)-2-pentanol 2(a)

(2R*,3S*,4S*)-2-(2,4-Difluorophenyl)-4,5-epoxy-3-methyl-1-(1H-1,2,4-triazol-1-yl)-2-pentanol 1.360 g (6.19 mmole) of 3-chloroperoxybenzoic acid of 80% purity) were added at 0° C. to a solution of 960 mg (3.44 mmole) of (2R*,3S*)-2-(2,4-difluorophenyl)-3-methyl-1-(1H-1,2,4-triazol-1-yl)-4-penten-2-ol (which was synthesized following the procedure disclosed in Japanese Patent Provisional Publication No. Sho 60-36468) in 30 ml of methylene chloride. Five minutes after the addition, the reaction mixture was stirred, and this stirring was continued overnight at room temperature. The reaction mixture was then diluted with ethyl acetate, after which it was washed, in turn, with an aqueous solution of sodium sulfite, with an aqueous solution of sodium hydrogencarbonate and with a saturated aqueous solution of sodium chloride. After it had been dried, the mixture was freed from the solvent by distillation under reduced pressure. The resulting residue was subjected to column chromatography through silica gel, using a 1:2 by volume mixture of ethyl actate and hexane as the eluent, to afford 320 mg of stereoisomer A of the title compound (having the lower polarity), melting at 160°–180° C. and 206 mg of the desired stereoisomer B of the title compound (having the higher polarity) as an oil.

Stereoisomer A (2R*,3S*,4S*):
Nuclear Magnetic Resonance Spectrum (CDCl₃), δ ppm: 0.82 (3H, doublet, J=7.3 Hz); 1.74 (1H, quintet, J=7.3 Hz); 2.54 (1H, doublet of doublets, J=4.0 & 2.8 Hz); 2.89 (1H, triplet, J=4.4 Hz); 3.3–3.4 (1H, multiplet); 4.90 (2H, AB-doublet, J=14.5 Hz); 5.06 (1H, broad singlet); 6.6–6.8 (2H, multiplet); 7.3–7.5 (1H, multiplet); 7.79 (1H, singlet); 7.80 (1H, singlet).

Stereoisomer B (2R*,3S*,4R*):
Nuclear Magnetic Resonance Spectrum (CDCl₃), δ ppm: 0.94 (3H, doublet, J=6.9 Hz); 1.86 (1H, quintet, J=6.9 Hz); 2.74 (1H, doublet of doublets, J=4.8 & 2.8 Hz); 2.95 (1H, triplet, J=4.8 Hz); 3.2–3.3 (1H, multiplet); 4.80 (2H, AB-doublet, J=13.7 Hz); 4.92 (1H, singlet); 7.6-7.8 (2H, multiplet); 7.3-7.5 (1H, multiplet); 7.78 (1H, singlet); 7.86 (1H, singlet).

2(b)
(2R*,3S*,4S*)-2-(2,4-Difluorophenyl)-3-methyl-1-(1H-1,2,4-triazol-1-yl)-2,4-pentanediol 84 mg (2.16 mmole) of lithium aluminum hydride were added, under an atmosphere of nitrogen, to a solution of 320 mg (1.08 mmole) of (2R*,3S*,4S*)-2-(2,4-difluoro-phenyl)-4,5-epoxy-3-methyl-1-(1H-1,2,4-triazol-1-yl)-2-pentanol (stereoisomer A) [prepared as described in step (a) above] in 20 ml of diethyl ether, whilst ice-cooling and stirring. Ten minutes later the reaction mixture was heated under reflux, and this was continued for hour. At the end of this time, the mixture was cooled, and 2 ml of water were slowly added; the mixture was then stirred for 10 minutes. The insoluble materials in the reaction mixture were removed by filtration using a Celite filter aid, and then the residue was washed with ethyl acetate. The combined filtrate and washings were dried and freed from the solvent by distillation under reduced pressure. The resulting oily residue was subjected to column chromatography through silica gel, using a 5:5:1 by volume mixture of ethyl acetate, chloroform and hexane as the eluent, to afford 240 mg of the title compound.

Nuclear Magnetic Resonance Spectrum (CDCl$_3$), δ ppm: 0.80 (3H, doublet of doublets, J=6.9 & 3.0 Hz); 2.00 (1H, quartet of doublets, J=6.9 & 1.6 Hz); 3.86 (1H, quartet of doublets, J=6.9 & 1.6 Hz); 4.62 (1H, doublet, J=14 Hz); 4.93 (2H, singlet); 6.7-6.9 (2H, multiplet); 7.50 (1H, triplet of doublets, J=8.9 & 6.5 Hz); 7.82 (1H, singlet); 8.13 (1H, singlet).

2(c)
(2R*,3S*,4S*)-2-(2,4-Difluorophenyl)-4-(methanesulfonyloxy)-3-methyl-1-(1H-1,2,4-triazol-1-yl)-2-pentanol 140 mg (1.22 mmole) of methanesulfonyl chloride were added at 0° C. to a solution of 213 mg (0.72 mmole) of (2R*,3S*,4S*)-2-(2,4-difluorophenyl)-3-methyl-1-(1H-1,2,4-triazol-1-yl)-2,4-pentanediol [prepared as described in step (b) above] in 4 ml of pyridine, and the mixture was stirred for 2.5 hours. At the end of this time, the pyridine was removed by distillation under reduced pressure. The resulting residue was mixed with a dilute aqueous solution of sodium hydrogencarbonate and extracted with ethyl acetate. The extract was dried over anhydrous sodium sulfate and freed from the solvent by evaporation under reduced pressure, to afford 270 mg of the title compound as an oil.

Nuclear Magnetic Resonance Spectrum (CDCl$_3$), δ ppm: 0.79 (3H, doublet of doublets, J=6.5 & 0.8 Hz); 1.49 (3H, doublet, J=6.5 Hz); 2.6-2.8 (1H, multiplet); 3.08 (3H, singlet); 4.85 (2H, AB-doublet, J=13.9 Hz); 5.3-5.4 (1H, multiplet); 6.6-6.8 (2H, multiplet); 7.2-7.4 (1H, multiplet); 7.76 (1H, singlet); 7.81 (1H, singlet).

PREPARATION 3
(2R*,3R*)-2-(2,4-Difluorophenyl)-4,5-epoxy-3-methyl-1-(1H-1,2,4-triazol-1-yl)-2-pentanol 635 mg (3.13 mmole) of 3-chloroperoxybenzoic acid (of 85% purity) were added to a solution of 514 mg (1.84 mmole) of (2R*,3R*)-2-(2,4-difluorophenyl)-3-methyl-1-(1H,1,2,4-triazol-1-yl)-4-penten-2-ol (which was prepared by a procedure disclosed in Japanese Patent Provisional Publication No. Sho 60-36468) in 15 ml of methylene chloride. Five minutes later the temperature of the reaction mixture was allowed to rise to room temperature, and the mixture was stirred for 2 hours. At the end of this time, the reaction mixture was diluted with ethyl acetate and washed, in turn, with an aqueous solution of sodium sulfite, with an aqueous solution of sodium hydrogencarbonate and with a saturated aqueous solution of sodium chloride, in that order. The organic layer was then dried over anhydrous sodium sulfate and the solvent was removed by distillation under reduced pressure. The resulting residue was subjected to column chromatography through silica gel, using a 2:1 by volume mixture of ethyl acetate and hexane as the eluent, to afford 472 mg of the title compound as a solid.

The product was determined to be about a 3:1 mixture of two stereoisomers with respect to the carbon atom at the C$_4$ position.

Recrystallization from a mixture of ethyl acetate and hexane gave a major isomer, melting at 106°-109° C.

Nuclear Magnetic Resonance Spectrum (CDCl$_3$), δ ppm: 1.30 (3H, doublet, J=6 Hz); 1.90 (1H, broad quintet); 2.00 (1H, doublet of doublets, J=4 & 3 Hz); 2.35 (1H, triplet, J=4 Hz); 2.85 (1H, multiplet); 4.53 (1H, doublet, J=14 Hz); 4.89 (1H, doublet of doublets, J=14 & 1.5 Hz); 4.9 (1H, broad); 6.5-7.0 (2H, multiplet); 7.3-7.7 (1H, multiplet); 7.79 (1H, singlet); 7.91 (1H, singlet).

PREPARATION 4
(2R*,3R*,4S*)-2-(2,4-Difluorophenyl)-3-methyl-1-(1H-1,2,4-triazol-1-yl)-2,4-pentanediol 53 mg (1.40 mmole) of lithium aluminum hydride were added, under an atmosphere of nitrogen, to a solution of 207 mg (0.70 mmole) of (2R*,3R*)-2-(2,4-difluorophenyl)-4,5-epoxy-3-methyl-1-(1H-1,2,4-triazol-1-yl)-2-pentanol [about a 3:1 mixture of isomers at the C$_4$ position, prepared as described in Preparation 3] in 4 ml of diethyl ether, whilst ice-cooling and stirring. Ten minutes later the reaction mixture was heated under reflux, and this was continued for 1 hour. At the end of this time, the mixture was cooled, and 1 ml of water was slowly added, after which the mixture was stirred for 10 minutes. The insoluble materials were removed by filtration using a Celite filter aid, after which the residue was washed with ethyl acetate. The combined filtrate and washings were dried over anhydrous sodium sulfate, and the solvent was removed by distillation under reduced pressure. The resulting oily residue was subjected to column chromatography through silica gel, using a 5:5:1 by volume mixture of ethyl acetate, chloroform and hexane as the eluent, to afford 160 mg of the title compound.

This product was determined to be about a 3:1 mixture of two stereoisomers with respect to the carbon atom at the C$_4$ position.

Recrystallization from a mixture of benzene and hexane gave a major isomer, melting at 145°-146° C.

Nuclear Magnetic Resonance Spectrum (CDCl$_3$), δ ppm: 1.05 (3H, doublet, J=6.5 Hz); 1.25 (3H, doublet, J=6.5 Hz); 2.20 (1H, quartet of doublets, J=6.5 & 1 Hz); 3.03 (1H, broad singlet); 3.74 (1H, broad quartet, J=6.5 Hz); 4.51 (1H, doublet, J=14 Hz); 4.77 (1H, doublet of doublets, J=14 & 1 Hz); 5.33 (1H, singlet); 6.5-7.0 (2H, multiplet); 7.1-7.6 (1H, multiplet); 7.65 (1H, singlet); 7.89 (1H, singlet).

PREPARATION 5

(2R*,3R*)-3-(2,4-Dichlorophenyl)-3-hydroxy-2-methyl-4-(1H-1,2,4-triazol-1-yl)-butanal and (2S*,3R*)-3-(2,4-dichlorophenyl)-3-hydroxy-2-methyl-4-(1H-1,2,4-triazol-1-yl)-butanal 290 mg (1.32 mmole) of sodium metaperiodate and 1 mg of osmium tetraoxide were added to a solution of 139 mg (0.45 mmole) of a 1:1 mixture of (2R*,3S*)-4-(2,4-dichlorophenyl)-3-methyl-1-(1H-1,2,4-triazol-1-yl)-4-penten-2-ol and its (2R*,3R*)-isomer (which was synthesized by the procedure disclosed in Japanese Patent Provisional Publication No. Sho 60-36468) in 2.8 ml of a 5:2 by volume mixture of tetrahydrofuran and water, and the mixture was stirred overnight at room temperature. At the end of this time, the reaction mixture was diluted with ethyl acetate and washed with a saturated aqueous solution of sodium chloride. The organic layer was dried over anhydrous sodium sulfate, and solvent was removed by distillation under reduced pressure. The resulting oily residue was subjected to column chromatography through 4 g of silica gel, using a 4:5 by volume mixture of ethyl acetate and hexane as the eluent, to afford 27 mg of the (2R*,3R*)-isomer, 25 mg of a mixture of the (2R*,3R*)-isomer and the (2S*,3R*)-isomer, and 31 mg of the (2S*,3R*)-isomer in that order.

Recrystallization of the (2R*,3R*)-isomer from benzene gave a pure specimen, melting at 150°–157° C.

Recrystallization of the (2S*,3R*)-isomer from a mixture of benzene and ethyl acetate gave a pure specimen, melting at 155°–157° C.

(2R*,3R*)-isomer

Infrared Absorption Spectrum (CHCl₃), λ$_{max}$ cm⁻¹: 3400, 1715.

Nuclear Magnetic Resonance Spectrum (CDCl₃), δ ppm: 0.96 (3H, doublet, J=7 Hz); 3.47 (1H, quartet of doublets, J=7, 3 Hz); 4.64 (1H, doublet, J=14 Hz); 5.30 (1H, broad); 5.42 (1H, doublet, J=14 Hz); 7.11 (1H, doublet of doublets, J=8, 2 Hz); 7.31 (1H, doublet, J=2 Hz); 7.52 (1H, doublet, J=8 Hz); 7.77 (1H, singlet); 7.85 (1H, singlet); 9.88 (1H, doublet, J=3Hz)

(2S*,3R*)-isomer:

Nuclear Magnetic Resonance Spectrum (CDCl₃), δ ppm: 1.40 (3H, doublet, J=7 Hz); 3.52 (1H, quartet of doublets, J=7, 1.5 Hz); 4.50 (1H, doublet, J=14 Hz); 5.42 (1H, doublet, J=14 zz); 5.5 (1H, broad): 7.11 (1H, doublet of doublets, J=8, 2 Hz); 7.35 (1H, doublet, J=2 Hz); 7.54 (1H, doublet, J=8 Hz); 7.77 (1H, singlet); 7.86 (1H, singlet); 9.39 (1H, doublet, J=1.5Hz)

PREPARATION 6

(2S*,3R*)-3-(2,4-Dichlorophenyl)-2-methyl-4-(1H-1,2,4-triazol-1-yl)-1,3-butanediol and (2R*,3R*)-3-(2,4-dichlorophenyl)-2-methyl-4-(1H-1,2,4-triazol-1-yl)-1,3-butanediol 15 mg of sodium borohydride were added, whilst ice-cooling and stirring, to a solution of 85 mg of a 1:1 mixture of (2R*,3R*)-3-(2,4-dichlorophenyl)-3-hydroxy-2-methyl-4-(1H-1,2,4-triazol-1-yl)butanal and its (2S*,3R*)-isomer (prepared as described in Preparation 5) in 1.5 ml of methanol. Ten minutes later, the reaction mixture was diluted with ethyl acetate, after which the mixture was washed with a saturated aqueous solution of sodium chloride. The organic layer was freed from the solvent by distillation under reduced pressure, to afford a crude product. This product was subjected to column chromatography through 3 g of silica gel, using ethyl acetete as the eluent, to give 31 mg of the (2R*,3R*)-isomer of the title compound.

Recrystallization of this from a mixture of benzene and hexane gave a pure specimen, melting at 120°–122° C.

The column was then eluted with ethyl acetate containing 7% by volume of methanol to give 33 mg of the (2S*,3R*)-isomer of the title compound.

Recrystallization of this from a mixture of benzene and hexane gave a pure specimen, melting at 176°–177° C.

(2R*,3R*)-isomer:

Nuclear Magnetic Resonance Spectrum (CDCl₃), δ ppm: 1.39 (3H, doublet, J=7 Hz); 2.85 (1H, multiplet); 3.40 (1H, singlet); 3.45 (1H, singlet); 4.50 (1H, doublet, J=14 Hz); 5.31 (1H, doublet, J=14 Hz); 7.05 (1H, doublet of doublets, J=8 & 2 Hz); 7.25 (1H, doublet, J=2 Hz); 7.52 (1H, doublet, J=8 Hz); 7.66 (1H, singlet); 7.91 (1H, singlet).

(2S*,3R*)-isomer:

Infrared Absorption Spectrum (Nujol), λ$_{max}$ cm⁻¹: 3400, 3140.

Nuclear Magnetic Resonance Spectrum [CDCl₃: CD₃OD (1:1 by volume)], δ ppm: 0.77 (3H, doublet, J=7 Hz); 2.9 (1H, multiplet); 3.6–4.3 (2H, multiplet); 4.74 (1H, doublet, J=14.5 Hz); 5.44 (1H, doublet, J=14.5 Hz); 7.04 (1H, doublet of doublets, J=9, 2 Hz); 7.30 (1H, doublet, J=2 Hz); 7.48 (1H, doublet, J=9 Hz); 7.67 (1H, singlet); 8.07 (1H, singlet).

PREPARATION 7

(2R*,3S*)-2-(2,4-Dichlorophenyl)-4-(methanesulfonyloxy)-3-methyl-1-(1H-1,2,4-triazol-1-yl)-2-butanol 61 mg (0.61 mmole) of triethylamine and 64 mg (0.56 mmole) of methanesulfonyl chloride were added at 0° C., whilst stirring, to a solution of 74 mg (0.231 mmole) of (2S*,3R*)-3-(2,4-dichlorophenyl)-2-methyl-4-(1H-1,2,4-triazol-1-yl)-1,3-butanediol in 2 ml of methylene chloride. Fifteen minutes later the reaction mixture was mixed with a dilute aqueous solution of sodium hydrogencarbonate and extracted with ethyl acetate. The extract was washed with a saturated aqueous solution of sodium chloride, and the solvent was removed by evaporation under reduced pressure, to give 92 mg of a crude product.

Nuclear Magnetic Resonance Spectrum (CDCl₃), δ ppm: 0.70 (3H, doublet, J=7 Hz); 3.07 (3H, singlet); 2.9–3.4 (1H, multiplet); 4.22 (1H, doublet of doublets, J=10 & 5 Hz); 4.59 (1H, doublet, J=14.5 Hz); 4.71 (1H, doublet of doublets, J=10 & 7 Hz); 5.18 (1H, broad); 5.51 (1H, doublet, J=14.5 Hz); 7.04 (1H, doublet of doublets, J=8 & 2 Hz); 7.27 (1H, doublet, J=2 Hz); 7.43 (1H, doublet, J=8 Hz); 7.73 (1H, singlet); 7.81 (1H, singlet).

PREPARATION 8

(2R*,4R*)-2-(4-Chlorophenyl)-2-ethoxycarbonyl-3,4-dimethyloxetane

2-Butene was bubbled into 200 ml of benzene at 0° C. until the benzene solution increased to about 1.25 times its original volume. 24.3 g (114.09 mmole) of ethyl 4-chlorophenylglyoxylate were then added to the mixture, and the resulting mixture was irradiated with a 450 watt medium pressure mercury-arc lamp (Hannovea Co., Inc.) at 15° C. for 3 hours. At the end of this time, the reaction mixture was concentrated by evaporation under reduced pressure, and the resulting residue was subjected to column chromatography through silica gel, eluted with a 10:1 by volume mixture of hexane and ethyl acetate, to afford 23.4 g (yield 76%) of the title compound, boiling at 141°-142° C./2.7 Torr.

Nuclear Magnetic Resonance Spectrum (CDCl$_3$), δ ppm: 0.76 (doublet, J=7.66 Hz); 1.23-1.31 (multiplet); 1.34 (doublet, J=6.04 Hz); 2.83 (quintet, J=7.25 Hz); 3.55 (quintet, J=7.25 Hz); 4.16-4.32 (multiplet); 4.56 (quintet, J=6.45 Hz); 5.06 (quintet, J=7.25 Hz); 7.26-7.45 (multiplet).

Mass Spectrum (m/z): 268 (M+), 224, 213, 195, 178, 167.

PREPARATION 9

(2R*,3S*,4R*)-2-(4-Chlorophenyl)-3,4-dimethyl-2-hydroxymethyloxetane and
(2R*,3R*,4R*)-2-(4-chlorophenyl)-3,4-dimethyl-2-hydroxymethyloxetane 3.2 ml (3.2 mmole) of a 1M solution of lithium aluminum hydride in tetrahydrofuran were added dropwise at 0° C. to a solution of 920 mg (3.42 mmole) of a 1:1 mixture of (2R*,3R*,4R*)-2-(4-chlorophenyl)-3,4-dimethyl-2-ethoxycarbonyloxetane and its (2R*,3S*,4R*) isomer (prepared as described in Preparation 8) in 7 ml of tetrahydrofuran, and the resulting mixture was stirred at the same temperature for 30 minutes. At the end of this time, a saturated aqueous solution of ammonium chloride and 1N aqueous hydrochloric acid were added, in turn, to the reaction mixture. The crude products obtained by extraction of the reaction mixture with ethyl acetate were subjected to column chromatography through silica gel, eluted with a 5:1 by volume mixture of hexane and ethyl acetate, to afford 336.4 mg of isomer A of the title compound having the (2R*,3S*,4R*) configuration and 349.5 mg of isomer B of the title compound having the (2R*,3R*,4R*) configuration.

Isomer A

Nuclear Magnetic Resonance Spectrum (CDCl$_3$), δ ppm:
0.70 (3H, doublet, J=7.66 Hz); 1.24 (3H, doublet, J=6.44 Hz); 3.33 (1H, doublet, J=7.66 Hz); 3.63 (1H, doublet, J=12.08 Hz); 3.87 (1H, doublet, J=12.08 Hz); 4.96 (1H, doublet of quartets, J=6.44 & 7.66 Hz); 7.25 (2H, doublet, J=8.46 Hz); 7.35 (2H, doublet, J=8.46 Hz).

Mass Spectrum (m/z): 223, 195, 181, 167, 153, 139.

Isomer B

Nuclear Magnetic Resonance Spectrum (CDCl$_3$), δ ppm:
1.36 (3H, doublet, J=6.04 Hz); 1.36 (3H, doublet, J=7.25 Hz); 2.18 (1H, broad doublet of doublets, J=5.53 & 7.25 Hz); 2.65 (1H, quintet, J=7.25 Hz); 3.71 (1H, doublet of doublets, J=5.53 & 12.09 Hz); 4.02 (1H, doublet of doublets, J=7.25 & 12.09 Hz); 4.56 (1H, doublet of quartets, J=6.04 & 7.25 Hz); 7.24 (2H, doublet, J=8.46 Hz); 7.33 (2H, doublet, J=8.46 Hz).

Mass Spectrum (m/z): 195, 167, 139, 129, 125, 115.

PREPARATION 10

2-(4-Chlorophenyl)-3,4-dimethyl-2-methanesulfonyloxymethyloxetane 0.13 ml (1.68 mmole) of methanesulfonyl chloride, followed by 0.24 ml (1.708 mmole) of triethylamine were added at 0° C. to a solution of 123 mg (0.543 mmole) of 2-(4-chlorophenyl)-3,4-dimethyl-2-hydroxymethyloxetane in 10 ml of methylene chloride, and the resulting mixture was stirred for 4 hours, during which time the reaction temperature was allowed to rise to room temperature. At the end of this time, a saturated aqueous solution of sodium hydrogencarbonate was added to the mixture, which was then extracted with methylene chloride. The extract was dried over anhydrous magnesium sulfate and concentrated by evaporation under reduced pressure. The resulting residue was subjected to column chromatography through silica gel, eluted with a 10:1 by volume mixture of hexane and ethyl acetate, to afford 107 mg (yield 65%) of the title compound.

Nuclear Magnetic Resonance Spectrum (CDCl$_3$), δ ppm:
0.72 (3H, doublet, J=7.25 Hz); 1.21 (3H, doublet, J=6.44 Hz); 3.02 (3H, singlet); 3.25 (1H, quintet, J=7.25 Hz); 4.33 (1H, doublet, J=11.68 Hz); 4.60 (1H, doublet, J=11.68 Hz); 5.04 (1H, doublet of quartets, J=6.44 & 7.25 Hz); 7.28 (1H, doublet, J=8.86 Hz); 7.37 (2H, doublet, J=8.86 Hz).

PREPARATION 11

(2R*,4R*)-2-Chloromethyl-2-(4-chlorophenyl)-3,4-dimethyloxetane

2-Butene was bubbled into 180 ml of benzene at 0° C. until the benzene solution increased to about 1.25 times its original volume. 15 g (79.34 mmole) of 4-chlorophenacyl chloride were then added to the solution, after which the mixture was irradiated with a 450 watt medium pressure mercury-arc lamp (Hannovea Co., Inc.) for 15 hours. At the end of this time, the reaction mixture was concentrated by evaporation under reduced pressure. It then was distilled under reduced pressure to give 15.24 mg (78.4%) of the title compound, boiling at 132-133° C./3.2 Torr. Judging from the NMR spectrum, this compound is about a 1:3 mixture of α and β isomers in respect of the C$_3$ position.

Mass Spectrum (m/z):
246 [(M+2)+], 244 (M+), 195, 191, 190, 165, 151, 141, 139.

Nuclear Magnetic Resonance Spectrum (CDCl$_3$), δ ppm:
0.72 (doublet, J=7.00 Hz); 1.24 (doublet, J=6.40 Hz); 1.33 (doublet, J=7.00 Hz); 1.34 (doublet, J=6.40 Hz); 2.74 (doublet of quartets, J=7.00 & 7.00 Hz); 3.24 (doublet of quartets, J=7.54 & 7.54 Hz); 3.82 (doublet, J=11.62 Hz); 3.90 (doublet, J=11.62 Hz); 3.91 (doublet, J=11.62 Hz); 4.00 (doublet, J=11.62 Hz); 4.55 (doublet of quartets, J=6.40 & 7.00 Hz); 5.05 (doublet of quartets, J=6.40 & 7.00 Hz); 7.23-7.40 (multiplets).

PREPARATION 12

(2R*,3R*)-2-(4-Chlorophenyl)-3-methyl-2-(trimethylsilyloxy)-1-(1H-1,2,4-triazol-1-yl)-4-pentene 2.47 ml (19.4 mmole) of trimethylsilyl chloride and 1.7 g (24.3 mmole) of imidazole were added to a solution of 900 mg (3.24 mmole) of (2R*,3R*)-3-methyl-2-(4-chlorophenyl)-(1H-1,2,4-triazol-1-yl)-2-pentanol in 20 ml of N,N-dimethylformamide, and then the mixture was stirred at 50° C. for 4 hours. At the end of this time, the reaction mixture was poured into water and extracted with ethyl acetate. The extract was washed with water and dried over anhydrous sodium sulfate, after which the solvent was removed by distillation under reduced pressure to give 1.3 g of the title compound in the form of a crude oil.

Nuclear Magnetic Resonance Spectrum (CDCl$_3$), δ ppm:

0.17 (9H, singlet); 0.88 (3H, doublet, J=6.7 Hz); 2.7–2.85 (1H, multiplet); 4.47 (1H, doublet, J=14.7 Hz); 4.82 (1H, doublet, J=14.7 Hz); 5.05–5.2 (2H, multiplet); 5.5–5.7 (1H, multiplet); 7.2–7.3 (4H, multiplet); 7.54 (1H, singlet); 7.78 (1H, singlet).

PREPARATION 13

(2R*,3R*)-2-(4-Chlorophenyl)-3-methyl-2-trimethylsilyloxy -1-(1H-1,2,4-triazol-1-yl)butanal Ozone was blown into a solution of 190 mg (0.54 mmole) of (2R*,3R*)-3-methyl-2-(4-chlorophenyl)-2-(trimethylsilyloxy) -1-(1H-1,2,4-triazol-1-yl)-4-pentene in 10 ml of methanol, whilst cooling with dry ice in acetone. The end point of the reaction was confirmed by thin-layer chromatography, after which a suitable amount of potassium iodide power was added to the reaction mixture. An aqueous solution of sodium carbonate was then added to the mixture, which was then extracted with ethyl acetate. The extract was washed, in turn, with a w/v aqueous solution of sodium thiosulfate and with water, in that order, and dried over anhydrous magnesium sulfate. The solvent was then removed by distillation under reduced pressure to give 140 mg (74%) of the title compound in the form of an oil.

Nuclear Magnetic Resonance Spectrum (CDCl$_3$), δ ppm:

0.17 (9H, singlet); 1.28 (3H, doublet, J=6.9 Hz); 3.04 (1H, quartet, J=6.9 Hz); 4.48 (1H, doublet, J=15 Hz); 4.67 (1H, doublet, J=15 Hz); 7.04 (2H, doublet, J=8.6 Hz); 7.27 (2H, doublet, J=8.6 Hz); 7.55 (1H, singlet); 7.88 (1H, singlet); 9.325 (1H, doublet, J=1.26 Hz).

PREPARATION 14

(2R*,3R*)-2-(4-Chlorophenyl)-3-methyl-2-trimethylsilyloxy -1-(1H-1,2,4-triazol-1-yl)-4-pentanol 0.45 ml (0.38 mmole) of diethylaluminum chloride (as a 0.84 molar hexane solution) was added to a solution of 111.1 mg (0.316 mmole) of (2R*,3R*)-3-methyl-2-(4-chlorophenyl) -2-(trimethylsilyloxy)-1-(1H-1,2,4-triazol-1-yl)butanal in 10 ml of tetrahydrofuran, and then the mixture was cooled to an internal temperature of −78° C. with dry ice in acetone. 1.39 ml (1.14 mmole) of methylmagnesium bromide (as a 0.82 molar diethyl ether solution) were added to the mixture, which was then stirred for 3 hours at the same temperature. At the end of this time, the reaction mixture was poured into water and extracted with ethyl acetate. The extract was washed, in turn, with water and with an aqueous solution of sodium chloride. It was then dried over anhydorus magnesium sulfate, and the solvent was removed by distillation under reduced pressure to give 85.4 mg (73%) of the title compound in the form of an oil. Judging from the NMR spectrum of the product, this compound is thought to be about a 1:5 mixture of the C$_4$ isomers.

Nuclear Magnetic Resonance Spectrum (CDCl$_3$), δ ppm:

0.087 (singlet); 0.284 (singlet); 0.77 (doublet, J=6 Hz); 0.94 (doublet, J=6.5 Hz); 1.08 (doublet, J=6 Hz); 1.28 (doublet, J=6.9 Hz); 2.0–2.1 (multiplet); 3.5–3.65 (multiplet); 4.14 (doublet, J=13.8 Hz); 4.69 (doublet, J=13.8 Hz); 7–4.85 (multiplet); 6.74 (doublet, J=8.67 Hz); 7.2–7.35 (multiplet); 7.88 (singlet).

PREPARATION 15

(2R*,3R*)-2-(4-Chlorophenyl)-3-methyl-1-(1H-1,2,4-triazol -1-yl)-2,4-pentanediol 0.35 ml (0.35 mmole) of tetrabutylammonium fluoride (as a 1 molar tetrahydrofuran solution) was added to a solution of 85.4 mg (0.233 mmole) of (2R*,3R*)-3-methyl-2-(4-chlorophenyl)-2-(trimethylsilyloxy)-1-(1H-1,2,4-triazol -1-yl)-4-pentanol (prepared as described in Preparation 7) in 2.5 ml of tetrahydrofuran, and then the mixture was stirred at room temperature for 30 minutes. At the end of this time, the reaction mixture was poured into water and extracted with ethyl acetate. The extract was washed with water and dried over anhydrous magnesium sulfate. The solvent was then removed by distillation under reduced pressure, to afford 64 mg (93%) of the title compound. Judging from the NMR spectrum, this compound is thought to be about a 5:1 mixture of the (2R*,3R*,4S*) isomer and the (2R*,3R*,4R*) isomer.

Nuclear Magnetic Resonance Spectrum (CDCl$_3$), δ ppm:

0.81 (doublet, J=7 Hz); 1.01 (doublet, J=7 Hz); 1.12 (doublet, J=7 Hz); 1.25 (doublet, J=7 Hz); 1.99 (quartet, J=7 Hz); 3.68 (quartet, J=7 Hz); 4.44 (AB-doublet, J=15 Hz); 4.75 (AB-doublet, J=15 Hz); 7.1–7.4 (multiplet); 7.68 (singlet); 7.74 (singlet); 8.00 (singlet).

PREPARATION 16

Ethyl 3-(4-chlorophenyl)-2,2-dimethyl-3-hydroxy-4-(1H-1,2,4-trizol-1-yl)butanoate 30 ml (30 mmole) of diethylaluminum chloride (as a 1.0 molar hexane solution) were added to a suspension of 2.0 g (30 mmole) of zinc and 0.14 g (1 mmole) of cuprous bromide in 30 ml of tetrahydrofuran. A solution of 1.33 g (6 mmole) of 4'-chloro-2-(1H-1,2,4-triazol-1-yl)-acetophenone and 6.7 g (30 mmole) of ethyl 2-bromoisobutyrate in 30 ml of tetrahydrofuran was then added dropwise to the mixture, after which it was stirred at room temperature for 18 hours. At the end of this time, water and 1N aqueous hydrochloric acid were added to the reaction mixture to give a precipitate, which was filtered off using a Celite filter aid and washed with ethyl acetate. The filtrate and the washings were combined and washed, in turn, with 1N aqueous hydrochloric acid, with an aqueous solution of ammonium chloride and with a saturated aqueous solution of sodium chloride. The solution was then dried and concentrated by evaporation under reduced pressure, to leave a residue, which was purified by column chromatography through silica gel, eluted with a 1:4 by volume mixture of hexane and ethyl acetate, to afford 1.89 g (93%) of the title compound in the form of an oil.

Mass Spectrum (m/z): 337 (M+), 292, 252, 222, 139.

Nuclear Magnetic Resonance Spectrum (CDCl$_3$), δ ppm:

1.21 (3H, singlet); 1.21 (3H, triplet, J=7 Hz); 1.23 (3H, singlet); 4.10 (2H, quartet, J=7 Hz); 4.63 (1H, doublet, J=14 Hz); 5.13 (1H, doublet, J=14 Hz); 5.37 (1H, broad singlet); 7.05–7.40 (4H, multiplet); 7.65 (1H, singlet); 7.92 (1H, singlet).

PREPARATIONS 17 TO 32

Following the procedure described in Preparation 16, the following compounds were obtained.

PREPARATION 17

Octyl 3-(2,4-difluorophenyl)-3-hydroxy-4-(1H-1,2,4-trizol-1-yl)butanoate, as an oil, in a yield of 42%.

Nuclear Magnetic Resonance Spectrum (CDCl$_3$), δ ppm:

0.50–1.70 (15H, multiplet); 2.65 (1H, doublet, J=15 Hz); 3.21 (1H, doublet, J=15 Hz); 3.95 (2H, triplet, J=6 Hz); 4.36 (1H, doublet, J=13 Hz); 4.68 (1H, doublet, J=13 Hz); 5.10 (1H, broad singlet); 6.55–7.00 (2H, multiplet); 7.10–7.80 (1H, multiplet); 7.81 (1H, singlet); 8.15 (1H, singlet).

Mass Spectrum (m/z): 395 (M+), 313, 201, 183.

PREPARATION 18

Octyl 3-(2,4-difluorophenyl)-3-hydroxy-2-methyl-4-(1H-1,2,4-trizol-1-yl)butanoate, as an oil, in a yield of 42%.

Nuclear Magnetic Resonance Spectrum (CDCl$_3$), δ ppm:

0.70–1.95 (15H, multiplet); 3.28 (1H, quartet, J=7 Hz); 4.15 (2H, triplet, J=6 Hz); 4.46 (1H, doublet, J=13 Hz); 4.85 (1H, doublet, J=13 Hz); 5.18 (1H, singlet); 6.50–6.95 (2H, multiplet); 7.10–7.65 (1H, multiplet); 8.18 (1H, singlet).

Mass Spectrum (m/z): 409 (M+), 327, 224, 215, 197.

PREPARATION 19

Ethyl 3-(2,4-difluorophenyl)-3-hydroxy-4-(1H-1,2,4-trizol-1-yl)butanoate, as an oil, in a yield of 62%.

Nuclear Magnetic Resonance Spectrum (CDCl$_3$): δ ppm:

1.10 (3H, triplet, J=7 Hz); 2.65 (1H, doublet, J=16 Hz); 3.20 (1H, doublet, J=16 Hz); 3.99 (2H, quartet, J=7 Hz); 4.39 (1H, doublet, J=14 Hz); 4.68 (1H, doublet, J=14 Hz); 5.25 (1H, broad singlet); 6.50–7.00 (2H, multiplet); 7.15–7.75 (1H, multiplet); 7.76 (1H, singlet); 8.12 (1H, singlet).

Mass Spectrum (m/z): 312 (M+), 229, 182, 141.

PREPARATION 20

Ethyl 3-(2,4-difluorophenyl)-3-hydroxy-2-methyl-4-(1H-1,2,4-trizol-1-yl)butanoate, as an oil, in a yield of 58%.

Nuclear Magnetic Resonance Spectrum (CDCl$_3$), δ ppm:

0.90 (3H, doublet, J=7 Hz); 1.23 (3H, triplet, J=7 Hz); 3.19 (1H, quartet, J=7 Hz); 4.13 (2H, quartet, J=7 Hz); 4.41 (1H, doublet, J=13 Hz); 4.77 (1H, doublet, J=13 Hz); 5.10 (1H, broad singlet); 6.45–7.00 (2H, multiplet); 7.20–7.65 (1H, multiplet); 7.66 (1H, singlet); 7.95 (1H, singlet).

Mass Spectrum (m/z): 325 (M+), 243, 224, 197, 182, 141.

PREPARATION 2

Ethyl 3-(2,4-difluorophenyl)-2-ethyl-3-hydroxy-4-(1H-1,2,4-trizol-1-yl)butanoate, melting at 100°–105° C., in a yield of 57%.

Nuclear Magnetic Resonance Spectrum (CDCl$_3$), δ ppm:

0.78 (3H, triplet, J=7 Hz); 1.32 (3H, triplet, J=7 Hz); 1.00–2.10 (2H, multiplet); 3.07 (1H, doublet of doublets, J=4 & 10 Hz); 4.22 (2H, quartet, J=7 Hz); 4.30 (1H, doublet, J=14 Hz); 4.84 (1H, doublet, J=14 Hz); 5.10 (1H, broad singlet); 6.47–6.92 (2H, multiplet); 7.10–7.60 (1H, multiplet); 7.61 (1H, singlet); 7.92 (1H, singlet).

Mass Spectrum (m/z): 339 (M+), 297, 257, 224, 211, 182, 141.

PREPARATION 22

Ethyl 3-(2,4-difluorophenyl)-3-hydroxy-2,2-dimethyl-4-(1H-1,2,4-trizol-1-yl)butanoate, melting at 90° C., in a yield of 70%.

Nuclear Magnetic Resonance Spectrum (CDCl$_3$), δ ppm:

1.20 (3H, doublet, J=2.0 Hz); 1.25 (3H, triplet, J=7.3 Hz); 1.30 (3H, singlet); 4.17 (2H, doublet of quartets, J=1.2 & 7.3 Hz); 4.65 (1H, doublet of doublets, J=1.8 & 14.1 Hz); 5.36 (1H, doublet of doublets, J=2.4 & 14.1 Hz); 5.42 (1H, singlet); 6.59–6.82 (2H, multiplet); 7.55–7.64 (1H, multiplet); 7.73 (1H, singlet); 8.02 (1H, doublet, J=1.6 Hz).

Mass Spectrum (m/z): 339 (M+), 294, 257, 224, 141.

PREPARATION 23

Ethyl 3-(2,4-difluorophenyl)-3-hydroxy-2-phenyl-4-(1H-1,2,4-trizol-1-yl)butanoate, as an oil, in a yield of 9%.

Nuclear Magnetic Resonance Spectrum (CDCl$_3$), δ ppm: 1.20 (3H, triplet, J=7 Hz); 4.10 (2H, quartet, J=7 Hz); 4.38 (1H, singlet); 4.78 (2H, singlet); 6.00 (1H, multiplet); 6.20–7.30 (3H, multiplet); 7.08 (5H, broad singlet); 7.70 (1H, singlet); 8.05 (1H, singlet).

Mass Spectrum (m/z): 387 (M+), 342, 305, 231, 224, 141.

PREPARATION 24

Ethyl 3-(4-chlorophenyl)-3-hydroxy-2-methyl-4-(1H-1,2,4-trizol-1-yl)butanoate, melting at 75°–90° C., in a yield of 57%.

Nuclear Magnetic Resonance Spectrum (CDCl$_3$), δ ppm:

1.03 (3H, triplet, J=7 Hz); 1.30 (3H, triplet, J=7 Hz); 2.98 (1H, quartet, J=7 Hz); 4.16 (2H, quartet, J=7 Hz); 4.35 (1H, doublet, J=13 Hz); 4.65 (1H, doublet, J=13 Hz); 5.00 (1H, broad singlet); 7.00–7.30 (4H, multiplet); 7.70 (1H, singlet); 7.81 (1H, singlet).

Mass Spectrum (m/z): 323 (M+), 276, 241, 222.

PREPARATION 25

Ethyl 3-(4-chlorophenyl)-2-ethyl-3-hydroxy-4-(1H-1,2,4-trizol-1-yl)butanoate, as an oil, in a yield of 91%.

Nuclear Magnetic Resonance Spectrum (CDCl$_3$), δ ppm:

0.82 (3H, triplet, J=7.6 Hz); 1.22–1.39 (2H, multiplet); 1.31 (3H, triplet, J=7.1 Hz); 1.63–1.77 (1H, multiplet); 4.18–4.28 (2H, multiplet); 4.39 (1H, doublet, J=14.1 Hz); 4.64 (1H, doublet, J=14.1 Hz); 7.20–7.28 (4H, multiplet); 7.75 (1H, singlet); 7.93 (1H, singlet).

Mass Spectrum (m/z): 337 (M+), 255, 222, 139.

PREPARATION 26

Ethyl 3-(4-fluorophenyl)-2-ethyl-3-hydroxy-4-(1H-1,2,4-trizol-1-yl)butanoate, as an oil, in a yield of 35%.

Nuclear Magnetic Resonance Spectrum (CDCl$_3$), δ ppm:

0.82 (3H, triplet, J=7.5 Hz); 1.32 (3H, triplet, J=7.1 Hz); 0.94–1.77 (2H, multiplet); 2.80 (1H, quartet, J=3.6 Hz); 4.16–4.33 (2H, multiplet); 4.41 (1H, doublet, J=14.1 Hz); 4.56 (1H, doublet, J=14.1 Hz); 6.89–7.02 (2H, multiplet); 7.22–7.29 (2H, multiplet); 7.77 (1H, singlet); 8.02 (1H, singlet).

Mass Spectrum (m/z): 321 (M+), 303, 276, 239.

PREPARATION 27

Ethyl 3-(4-fluorophenyl)-3-hydroxy-2,2-dimethyl-4-(1H-1,2,4-trizol-1-yl) butanoate, as an oil, in a yield of 87%.

Nuclear Magnetic Resonance Spectrum (CDCl$_3$), δ ppm:

1.20–1.28 (9H, multiplet); 4.07–4.19 (2H, multiplet); 4.71 (1H, doublet, J=14.1 Hz); 5.14 (1H, doublet, J=14.1 Hz); 6.89–7.38 (4H, multiplet); 7.75 (1H, singlet); 8.04 (1H, singlet).

Mass Spectrum (m/z): 321 (M+), 276, 239, 206.

PREPARATION 28

Ethyl 2-ethyl-3-hydroxy-3-(4-methylphenyl)-4-(1H-1,2,4-trizol-1-yl)butanoate, as an oil, in a yield of 75%.

Nuclear Magnetic Resonance Spectrum (CDCl$_3$), δ ppm:

0.81 (3H, triplet, J=7.3 Hz); 0.94–1.03 (1H, multiplet); 1.31 (3H, triplet, J=7.3 Hz); 1.23–1.41 (1H, multiplet); 1.63–1.75 (1H, multiplet); 4.19–4.27 (2H, multiplet); 4.39 (1H, doublet, J=14.1 Hz); 4.62 (1H, doublet, J=14.1 Hz); 7.05–7.63 (4H, multiplet); 7.76 (1H, singlet); 7.83 (1H, singlet).

Mass Spectrum (m/z): 317 (M+), 235, 202.

PREPARATION 29

Ethyl 3-hydroxy-2,2-dimethyl-3-(4-methylphenyl)-4-(1H-1,2,4-trizol-1-yl)butanoate, as an oil, in a yield of 82%.

Nuclear Magnetic Resonance Spectrum (CDCl$_3$), δ ppm:

1.20–1.28 (9H, multiplet); 2.27 (3H, singlet); 4.09–4.19 (2H, multiplet); 4.71 (1H, doublet, J=14.1 Hz); 5.12 (1H, doublet, J=14.1 Hz); 7.03 (2H, doublet, J=8.1 Hz); 7.76 (1H, singlet); 7.99 (1H, singlet).

Mass Spectrum (m/z): 318 (M+ +1), 272, 235, 202.

PREPARATION 30

Ethyl 3-hydroxy-3-(4-isopropylphenyl)-2,2-dimethyl-4-(1H-1,2,4-trizol-1-yl)butanoate, as an oil, in a yield of 85%.

Nuclear Magnetic Resonance Spectrum (CDCl$_3$), δ ppm:

1.17–1.23 (15H, multiplet); 2.75–2.88 (1H, multiplet); 4.05–4.16 (2H, multiplet); 4.73 (1H, doublet, J=14.5 Hz); 5.09 (1H, doublet, J=14.5 Hz); 5.18–5.24 (1H, broad singlet); 7.07–7.09 (2H, multiplet); 7.25–7.28 (2H, multiplet); 7.74 (1H, singlet); 7.96 (1H, singlet).

Mass Spectrum (m/z): 345 (M+), 263, 230.

PREPARATION 3

Ethyl 3-hydroxy-3-(4-methoxyphenyl)-2,2-dimethyl-4-(1H-1,2,4-trizol-1-yl)butanoate, as an oil, in a yield of 95%.

Nuclear Magnetic Resonance Spectrum (CDCl$_3$), δ ppm:

1.21–1.26 (9H, multiplet); 3.75 (3H, singlet); 4.07–4.21 (2H, multiplet); 4.70 (1H, doublet, J=14.5 Hz); 5.10 (1H, doublet, J=14.5 Hz); 5.08–5.13 (1H, broad singlet); 6.73–6.79 (2H, multiplet); 7.25–7.30 (2H, multiplet); 7.74 (1H, singlet); 7.97 (1H, singlet).

Mass Spectrum (m/z): 334 (M+ +1), 251, 218.

PREPARATION 32

Ethyl 2-ethyl-3-hydroxy-3-phenyl-4-(1H-1,2,4-trizol-1-yl)butanoate, melting at 72°–79° C., in a yield of 44%.

Nuclear Magnetic Resonance Spectrum (CDCl$_3$), δ ppm:

0.81 (3H, triplet, J=7.5 Hz); 1.33 (3H, triplet, J=7.1 Hz); 1.32–1.44 (1H, multiplet); 1.94–2.04 (1H, multiplet); 2.86 (1H, quartet, J=3.6 Hz); 4.18–4.32 (2H, multiplet); 4.42 (1H, doublet, J=14.1 Hz); 4.66 (1H, doublet, J=14.1 Hz); 7.16–7.33 (5H, multiplet); 7.75 (1H, singlet); 7.84 (1H, singlet).

Mass Spectrum (m/z): 303 (M+), 258, 221, 188.

PREPARATION 33

3-(4-Chlorophenyl)-2,2-dimethyl-4-(1H-1,2,4-triazol-1-yl) 1,3-butanediol 1.9 g (50.2 mmole) of sodium borohydride were added to a solution of 1.75 g (5.2 mmole) of ethyl 3-(4-chlorophenyl)-2,2-dimethyl-3-hydroxy-4-(1H-1,2,4-triazol-1-yl)butanoate in 25 ml of methanol, and then the mixture was heated under reflux for 3 hours. At the end of this time, the reaction mixture was allowed to cool, and it was then poured into ice-water and extracted with ethyl acetate. The extract was washed with an aqueous solution of ammonium chloride, dried and concentrated by evaporation under reduced pressure, to afford 1.5 g (98%) of the title compound melting at 120°–135° C.

Mass Spectrum (m/z): 295 (M+), 222, 139, 83.

Nuclear Magnetic Resonance Spectrum (CDCl$_3$), δ ppm:

0.82 (3H, singlet); 0.90 (3H, singlet); 3.23–3.30 (3H, multiplet); 4.56 (1H, doublet, J=14.7 Hz); 5.27 (1H, doublet, J=14.7 Hz); 5.59 (1H, singlet); 7.24–7.48 (4H, multiplet); 7.70 (1H, singlet); 8.25 (1H, singlet).

PREPARATIONS 34 TO 44

Following the procedure described in Preparation 33, the following compounds were obtained.

PREPARATION 34

3-(2,4-Difluorophenyl)-4-(1H-1,2,4-triazol-1-yl)-1,3-butanediol, melting at 89°–102° C., in a yield of 89%.

Nuclear Magnetic Resonance Spectrum (CDCl$_3$) δ ppm:

1.80–2.60 (2H, multiplet); 3.35–3.90 (2H, multiplet); 4.50 (4H, broad singlet); 6.50–6.95 (2H, multiplet); 7.15–7.85 (1H, multiplet); 7.65 (1H, singlet); 8.00 (1H, singlet).

Mass Spectrum (m/z): 270 (M+ +1), 253, 224, 187, 141.

PREPARATION 35

3-(2,4-Difluorophenyl)-2-methyl-4-(1H-1,2,4-triazol-1-yl)-1,3-butanediol, melting at 93°–113° C., in a yield of 89%.

Nuclear Magnetic Resonance Spectrum (CDCl$_3$) δ ppm:
0.84 (3H, doublet of doublets, J=1.2 & 7.3 Hz); 2.17–2.38 (1H, multiplet); 2.50 (1H, broad singlet); 3.82 (1H, doublet of doublets, J=5.2 & 11.3 Hz); 3.98 (1H, doublet of doublets, J=2.8 & 11.3 Hz); 4.77 (1H, doublet, J=14.1 Hz); 4.96 (1H, doublet of doublets, J=1.6 & 14.1 Hz); 5.30 (1H, broad singlet); 6.68–6.79 (2H, multiplet); 7.35–7.46 (1H, multiplet); 7.75 (1H, singlet); 7.92 (1H, singlet).

PREPARATION 36

3-(2,4-Difluorophenyl)-2-ethyl-4-(1H-1,2,4-triazol-1--1,3-butanediol, as an amorphous powder, in a yield of 94%.

Nuclear Magnetic Resonance Spectrum (CDCl$_3$) δ ppm:
0.83 (3H, triplet, J=7.5 Hz); 0.90–1.53 (3H, multiplet); 3.96 (1H, doublet of doublets, J=4.4 & 11.7 Hz); 4.11 (1H, doublet of doublets, J=2.0 & 11.7 Hz); 4.78 (1H, doublet, J=14.1 Hz); 4.95 (1H, doublet of doublets, J=1.2 & 14.1 Hz); 5.20 (1H, broad singlet); 6.68–6.80 (2H, multiplet); 7.31–7.40 (1H, multiplet); 7.74 (1H, singlet); 7.90 (1H, singlet).

PREPARATION 37

3-(2,4-Difluorophenyl)-2,2-dimethyl-4-(1H-1,2,4-triazol-1-yl)-1,3-butanediol, melting at 94°–104° C., in a yield of 92%.

Nuclear Magnetic Resonance Spectrum (CDCl$_3$) δ ppm:
0.93 (3H, doublet, J=2.0 Hz); 1.13 (3H, doublet, J=2.0 Hz); 3.49 (1H, doublet, J=11.5 Hz); 3.55 (1H, doublet, J=11.5 Hz); 4.60 (1H, doublet of doublets, J=2.0 & 13.9 Hz); 5.30 (1H, doublet of doublets, J=2.8 & 13.9 Hz); 5.82 (1H, broad singlet); 6.60–6.85 (2H, multiplet); 7.60–7.67 (1H, multiplet); 7.72 (1H, singlet); 8.02 (1H, singlet).

Mass Spectrum (m/z): 298 (M$^+$+1), 224, 182, 141.

PREPARATION 38

3-(2,4-Difluorophenyl)-2-phenyl-4-(1H-1,2,4-triazol-1-yl)-1,3-butanediol, as an oil, in a yield of 95%.

Nuclear Magnetic Resonance Spectrum (CDCl$_3$) δ ppm:
2.70–4.60 (5H, multiplet); 4.88 (1H, broad singlet); 5.25 (1H, doublet of doublets, J=4.8 & 7.2 Hz); 6.50–7.60 (3H, multiplet); 7.20 (5H, broad singlet); 7.70 (1H, singlet); 7.95 (1H, singlet).

PREPARATION 39

3-(4-Isopropylphenyl)-2,2-dimethyl-4-(1H-1,2,4-triazol-1-yl)-1,3-butanediol, as an oil, in a yield of 98%.

Nuclear Magnetic Resonance Spectrum (CDCl$_3$) δ ppm:
1.10–1.23 (12H, multiplet); 2.04–2.90 (1H, multiplet); 3.44 (1H, doublet, J=13.1 Hz); 3.48 (1H, doublet, J=13.1 Hz); 4.66 (1H, doublet, J=14.1 Hz); 4.98 (1H, doublet, J=14.1 Hz); 7.06–7.30 (4H, multiplet); 7.72 (1H, singlet); 7.96 (1H, singlet).

Mass Spectrum (m/z): 304 (M$^+$), 230, 221.

PREPARATION 40

3-(4-Methoxyphenyl)-2,2-dimethyl-4-(1H-1,2,4-triazol-1-yl)-1,3-butanediol, as an oil, in a yield of 61%.

Nuclear Magnetic Resonance Spectrum (CDCl$_3$) δ ppm:
0.81 (3H, singlet); 1.21 (3H, singlet); 3.54 (1H, doublet, J=11.5 Hz); 3.66 (1H, doublet, J=11.5 Hz); 3.78 (3H, singlet); 4.60 (1H, doublet, J=14.3 Hz); 4.98 (1H, doublet, J=14.3 Hz); 6.72–6.82 (2H, multiplet); 7.15–7.20 (2H, multiplet); 7.72 (1H, singlet); 8.05 (1H, singlet).

PREPARATION 41

2-Ethyl-3-phenyl-4-(1H-1,2,4-triazol-1-yl)-1,3-butanediol, as an oil, in a yield of 24%.

Nuclear Magnetic Resonance Spectrum (CDCl$_3$) δ ppm:
0.84 (3H, triplet, J=7.5 Hz); 1.22–1.40 (2H, multiplet); 1.73–1.87 (1H, multiplet); 3.80 (1H, doublet of doublets, J=4.4 & 5.6 Hz); 4.04 (1H, doublet of doublets, J=2.4 & 2.4 Hz); 4.58 (1H, doublet, J=14.1 Hz); 4.80 (1H, doublet, J=14.1 Hz); 7.19–7.38 (5H, multiplet); 7.98 (1H, singlet); 8.09 (1H, singlet).

Mass Spectrum (m/z): 261 (M$^+$), 240, 207, 188.

PREPARATION 42

3-(4-Chlorophenyl)-2-methyl-4-(1H-1,2,4-triazol-1-yl)-1,3-butanediol, as an oil, in a yield of 34%.

Nuclear Magnetic Resonance Spectrum (CDCl$_3$) δ ppm:
0.85 (3H, triplet, J=7.1 Hz); 2.08 (1H, doublet of triplets, J=3.3 & 7.0 Hz); 2.30–3.20 (2H, broad); 3.64 (1H, doublet of doublets, J=6.8 & 11.1 Hz); 3.85 (1H, doublet of doublets, J=3.3 & 11.1 Hz); 4.56 (1H, doublet, J=14.2 Hz); 4.79 (1H, doublet, J=14.2 Hz); 7.21–7.31 (4H, multiplet); 7.84 (1H, singlet); 8.09 (1H, singlet).

PREPARATION 43

3-(4-Chlorophenyl)-2-ethyl-4-(1H-1,2,4-triazol-1-yl)-1,3-butanediol, as an oil, in a yield of 26%.

Nuclear Magnetic Resonance Spectrum (CDCl$_3$) δ ppm:
0.82 (3H, triplet, J=7.6 Hz); 1.23–1.39 (2H, multiplet); 1.62–1.74 (1H, multiplet); 4.19–4.30 (2H, multiplet); 4.41 (1H, doublet, J=14.4 Hz); 7.22–7.28 (4H, multiplet); 7.78 (1H, singlet); 8.05 (1H, singlet).

Mass Spectrum (m/z): 295 (M$^+$), 222, 213.

PREPARATION 44

2-Ethyl-3-(4-fluorophenyl)-4-(1H-1,2,4-triazol-1-yl)-1,3-butanediol, melting at 65°–75° C., in a yield of 58%.

Nuclear Magnetic Resonance Spectrum (CDCl$_3$) δ ppm:
0.85 (3H, triplet, J=7.5 Hz); 1.30–1.37 (2H, multiplet); 1.70–1.85 (1H, multiplet); 3.51–3.69 (2H, multiplet); 3.77–3.84 (1H, multiplet); 4.02–4.07 (1H, multiplet); 4.57 (1H, doublet, J=14.1 Hz); 4.77 (1H, doublet, J=14.1 Hz); 6.92–7.90 (4H, multiplet); 8.04 (1H, singlet); 8.26 (1H, singlet).

Mass Spectrum (m/z): 279 (M$^+$), 206, 197.

FORMULATION 1

Wettable powder

A mixture comprising 10% of (2R*,3S*)-2-(2,4-difluorophenyl) -3,4-dimethyl-2-[(1H-1,2,4-triazol-1-yl)-methyl]oxetane (prepared as described in Example 1), 0.5% of Emulgen 810 TM (surface active agent, Kao Corporation), 0.5% of Demol N TM (surface active agent, Kao Corporation), 20% of Kunilite 201 (diatomaceous earth, Kunimie Co., Ltd.) and 69% of Zeeklite CA (clay, Zeeklite Mining Co.) was homogenously mixed and pulverized to make a wettable powder.

FORMULATION 2

Wettable powder

A mixture comprising 25% of (2R*,3S*)-2-(2,4-difluorophenyl) -3,4-dimethyl-2-[(1H-1,2,4-triazol-1-yl)-methyl]oxetane (prepared as described in Example 1), 2.5% of sodium dodecylbenzenesulfonate, 2.5% of sodium lignin sulfonate and 70% of diatomaceous earth was mixed and pulverized to make a wettable powder.

FORMULATION 3

Emulsifiable concentrate

A mixture comprising 15% of (2R*,3S*)-2-(2,4-difluorophenyl) -3,4-dimethyl-2-[(1H-1,2,4-triazol-1-yl)-methyl]oxetane (prepared as described in Example 1), 35% of cyclohexanone, 11% of polyoxyethylene nonylphenyl ether, 4% of calcium dodecylbenzenesulfonate and 35% of methylnaphthalene was homogenously dissolved to make an emulsifiable concentrate.

FORMULATION 4

Emulsifiable concentrate

A mixture comprising 30% of (2R*,3S*)-2-(2,4-difluorophenyl) -3,4-dimethyl-2-[(1H-1,2,4-triazol-1-yl)-methyl]oxetane (prepared as described in Example 1), 10% of an emulsifying agent [Sorpol SM100 TM (surface active agent, Toho Chemical Inc.)] and 60% of xylene was well mixed to make an emulsifiable concentrate.

FORMULATION 5

Granules

A mixture comprising 5% of (2R*,3S*)-2-(2,4-difluorophenyl) -3,4-dimethyl-2[(1H-1,2,4-triazol-1-yl)-methyl]oxetane nitrate (prepared as described in Example 1), 2% of sodium dodecyl sulfate, 5% of sodium lignin sulfonate, 2% of the sodium salt of carboxymethyl cellulose and 86% of clay was homogenously mixed and pulverized. 16 parts of water were then added to 100 parts of the resulting mixture. The mixture was kneaded, granulated using a extruding granulator, dried and sieved out by passing it through a 14-mesh sieve and a 32-mesh sieve to make granules.

FORMULATION 6

Granules

A mixture comprising 5% of (2R*,3S*)-2-(2,4-difluorophenyl) -3,4-dimethyl-2-[(1H-1,2,4-triazol-1-yl)-methyl]oxetane nitrate (prepared as described in Example 1), 30% of bentonite, 62% of talc, 2% of sodium lignin sulfonate and 1% of sodium dodecylbenzenesulfonate was homogeneously mixed and pulverized. 18 parts of water were then added to 100 parts of the resulting mixture. The mixture was kneaded, granulated using a extruding granulator, dried and sieved out by passing it through a 14-mesh sieve and a 32-mesh sieve to make granules.

FORMULATION 7

Granules

A mixture comprising 4% of (2R*,3S*)-2-(2,4-difluorophenyl) -3,4-dimethyl-2-[(1H-1,2,4-triazol-1-yl)-methyl]oxetane nitrate (prepared as described in Example 1), 30% of bentonite, 63% of talo, 1% of polyvinyl alcohol and 2% of sodium alkylbenzenesulfonate was homogeneously mixed and pulverized. 20 parts of water were then added to 100 parts of the resulting mixture. The mixture was kneaded, granulated using a extruding granulator, dried and sieved out by passing it through a 14-mesh sieve and a 32-mesh sieve to make granules.

FORMULATION 8

Granules

A mixture comprising 4% of (2R*,3S*)-2-(2,4-difluorophenyl) -3,4-dimethyl-2-[(1H-1,2,4-triazol-1-yl)-methyl]oxetane nitrate (prepared as described in Example 1), 35% of bentonite, 58% of talc, 2% of sodium alkylnaphthalenesulfonate and 1% of dioctyl sulfosuccinate was homogeneously mixed and pulverized. 20 parts of water were then added to 100 parts of the resulting mixture, and the mixture was kneaded, granulated using a extruding granulator, dried and sieved out by passing it through a 14-mesh sieve and a 32-mesh sieve to make granules.

FORMULATION 9

Granules

A mixture comprising 5% of (2R*,3S*)-2-(2,4-difluorophenyl) -3,4-dimethyl-2-[(1H-1,2,4-triazol-1-yl)-methyl]oxetane nitrate (prepared as described in Example 1), 1% of white carbon, 5% of sodium lignin sulfonate, 84% of clay and 5% of the sodium salt of carboxymethyl cellulose was thoroughly pulverized and mixed. 17 parts of water were then added to 100 parts of the resulting mixture, and the mixture was kneaded, granulated using a extruding granulator, dried and sieved out by passing it through a 14-mesh sieve and a 32-mesh sieve to make granules.

FORMULATION 10

Dusts

A mixture comprising 2% of (2R*,3S*)-2-(2,4-difluorophenyl) -3,4-dimethyl-2-[(1H-1,2,4-triazol-1-yl)-methyl]oxetane nitrate (prepared as described in Example 1), 5% of diatomaceous earth and 93% of clay was homogeneously mixed and pulverized to make a dust.

FORMULATION 11

Wettable powder

A mixture comprising 80% of (2R*,3S*)-2-(2,4-difluorophenyl) -3,4-dimethyl-2-[(1H-1,2,4-triazol-1-yl)-methyl]oxetane nitrate (prepared as described in Example 1), 2% of sodium alkylnaphthalenesulfonate, 2% of sodium lignin sulfonate, 3% of synthetic amorphous silica and 13% of kaolinite was mixed, pulverized using a hammer mill, again mixed and packaged.

FORMULATION 12

Granules

A mixture comprising 15% of the wettable powder prepared as described in Formulation 11, 69% of gypsum and 16% of potassium sulfate was mixed in a rotatory mixer or a running floor mixer and granulated by spraying water After most of the granules had attained a diameter of 0.42–1.0 mm, the granules were picked out and dried and those having a diameter of 0.42–1.0 mm were collected by passing through a sieve.

FORMULATION 13

High concentration concentrates

A mixture comprising 98.5% of (2R*,3S*)-2-(2,4-difluorophenyl) -3,4-dimethyl-2-[(1H-1,2,4-triazol-1-yl)-methyl]oxetane nitrate (prepared as described in Example 1), 0.5% of silica aerogel and 1.0% of synthetic amorphous fine silica was mixed and pulverized using a hammer mill to make a highly concentrated concentrate, almost all of which could pass through a sieve having 0.044 mm diameter openings.

FORMULATION 14

Aqueous suspension

A mixture comprising 25% of (2R*,3S*)-2-(2,4-difluorophenyl) -3,4-dimethyl-2-[(1H-1,2,4-triazol-1-yl)-methyl]oxetane nitrate (prepared as described in Example 1), 3% of hydrated attapulgite, 10% of crude calcium lignin sulfonate, 0.5% of sodium dihydrogenphosphate and 61.5% of water was pulverized in a ball mill, a sand mill or a roller mill until the diameter of the solid particles had been reduced to not less than 10 $\mu$m to make an aqueous suspension.

FORMULATION 15

Liquor

A mixture comprising 30% of (2R*,3S*)-2-(2,4-difluorophenyl) -3,4-dimethyl-2-[(1H-1,2,4-triazol-1-yl)-methyl]oxetane (prepared as described in Example 1) and 70% of dimethylformamide was stirred to make a liquor.

FORMULATION 16

Emulsifiable concentrate

A mixture comprising 15% of (2R*,3S*)-2-(2,4-difluorophenyl) -3,4-dimethyl-2-[(1H-1,2,4-triazol-1-yl)-methyl]oxetane (prepared as described in Example 1), 25% of a blend of calcium sulfonate with a nonionic surface active agent and 60% of xylene was dissolved, with stirring, to make an emulsifiable concentrate for agricultural use.

FORMULATION 17

Hard capsules

A mixture comprising 100 mg of (2R*,3R*)-2-(2-chloro-4-fluorophenyl) -3,4-dimethyl-2-[(1H-1,2,4-triazol-1-yl)methyl]oxetane (prepared as described in Example 8), 150 mg of lactose, 50 mg of cellulose and 6 mg of magnesium stearate was packed into each standard hard gelatin capsule divided into two parts. The unit capsules thus prepared were washed and then dried.

FORMULATION 18

Soft capsules 2-(2,4-Difluorophenyl)-3-ethyl-2-[(1H-1,2,4-triazol-1-yl)methyl]oxetane (prepared as described in Example 24) was mixed with an assimilable oil, for example, soy bean oil, cottonseed oil or olive oil, to prepare a mixture, which was put into gelatin using a pump for positive replacement to prepare a soft capsule containing 100 mg of active the component. The capsules were washed and then dried.

FORMULATION 19

Tablets

According to conventional means, tablets were prepared using 100 mg of 3,3,4-trimethyl-2-phenyl-2-(1H-1,2,4-triazol-1-yl) methyloxetane (prepared as described in Example 39), 0.2 mg of colloidal silicon dioxide, 5 mg of magnesium stearate, 275 mg of microcrystalline cellulose, 11 mg of starch and 98.8 mg of lactose. If desired, the tablets may be coated.

FORMULATION 20

Injections

The injections were prepared by stirring 1.5% by weight of 3-t-butyl-2-(4-chlorophenyl)-2-[(1H-1,2,4-triazol-1-yl)methyl]oxetane (prepared as described in Example 37) in 10% by volume of propylene glycol and then diluting this with distilled water for injections to the required volume. The liquid was finally sterilized.

FORMULATION 21

Suspension

The suspensions were prepared so as to contain 100 mg of pulverized 2-(4-chlorophenyl)-2-[(1H-1,2,4-triazol-1-yl) methyl]oxetane (prepared as described in Example 51), 100 mg of sodium carboxymethyl cellulose, 5 mg of sodium benzoate, 1.0 g of a sorbitol solution (Pharmacopeia Japonica) and 0.025 ml of vanillin in 5 ml.

FORMULATION 22

Cream

The cream was prepared by adding 100 mg of pulverized 2-(4-fluorophenyl)-2-[(1H-1,2,4-triazol-1-yl)methyl]oxetane (prepared as described in Example 55) to 5 g of a cream comprising 40% of white petroleum, 3% of microcrystalline wax, 10% of lanolin, 5% of Span 20, 0.3% of Tween 20 and 41.7% of water.

FORMULATION 23

Cream

The cream was prepared by heating a mixture comprising 2 parts of (2R*,3S*,4R*)-2-(4-chlorophenyl)-3,4-dimethyl-2-[(1H-1,2,4-triazol-1-yl)methyl]oxetane (prepared as described in Example 69), 5 parts of 1,2-propanediol, 5 parts of glycerol stearate, 5 parts of spermaceti wax, 10 parts of isopropyl myristate and 4 parts of polysorbate and subsequently adding 69 parts of water to the cooled mixture.

FORMULATION 24

Liquid medicines for topical application

The liquid medicines for application were prepared by mixing 1 part of 2-(2,4-difluorophenyl)-2-[(1H-1,2,4- triazol-1-yl) methyl]oxetane (prepared as described in Example 52) with 99 parts of poly(ethylene glycol) 300.

FORMULATION 25

Plasters

The plasters were prepared by warm-melting a mixture comprising 2 parts of 2-(4-isopropylphenyl)-2-[(1H-1,2,4-triazol-1-yl) methyl]oxetane (prepared as described in Example 53), 40 parts of poly(ethylene glycol) 400 and 58 parts of poly(ethylene glycol) 1500 and then cooling the mixture.

We claim:

1. A compound of formula (I):

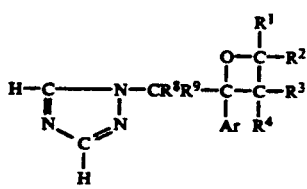

in which:

$R^1$ and $R^2$ are independently selected from the group consisting of hydrogen atoms and alkyl groups having from 1 to 6 carbon atoms, or $R^1$ and $R^2$, together with the carbon atom to which they are attached, form a cycloalkyl group having from 3 to 6 carbon atoms;

$R^3$ and $R^4$ are independently selected from the group consisting of hydrogen atoms, alkyl groups having from 1 to 6 carbon atoms and phenyl groups, or $R^3$ and $R^4$, together with the carbon atom to which they are attached, form a cycloalkyl group having from 3 to 6 carbon atoms;

or $R^1$ and $R^3$ and the carbon atoms to which they attached together form a cycloalkyl group having 5 or 6 ring atoms and fused to the oxetane ring;

Ar represents a phenyl group substituted by $R^5$, $R^6$ and $R^7$, where $R^5$, $R^6$ and $R^7$ are independently selected from the group consisting of hydrogen atoms, halogen atoms, alkyl groups having from 1 to 6 carbon atoms, alkoxy groups having from 1 to 6 carbon atoms, halogenated alkyl groups having from 1 to 6 carbon atoms and halogenated alkoxy groups having from 1 to 6 carbon atoms; and $R^8$ and $R^9$ are independently selected from the group consisting of hydrogen atoms and alkyl groups having from 1 to 4 carbon atoms;

and salts thereof.

2. The compound of claim 1, wherein $R^1$, $R^2$, $R^3$ and $R^4$ are the same or different and each represents a hydrogen atom or an alkyl group containing from 1 to 4 carbon atoms.

3. The compound of claim 1, wherein:
one of $R^1$ and $R^2$ represents a hydrogen atom and the other represents an alkyl group containing from 1 to 4 carbon atoms; and
one of $R^3$ and $R^4$ represents a hydrogen atom or an alkyl group containing from 1 to 4 carbon atoms and the other represents an alkyl group containing from 1 to 4 carbon atoms.

4. The compound of claim 1, wherein:
one of $R^1$ and $R^2$ represents a hydrogen atom and the other represents a methyl or ethyl group; and
one of $R^3$ and $R^4$ represents a hydrogen atom or a methyl group and the other represents a methyl group.

5. The compound of claim 1, wherein $R^1$ and $R^4$ both represent methyl groups and $R^2$ and $R^3$ both represent hydrogen atoms.

6. The compound of claim 1, wherein $R^1$ represents an ethyl group, $R^4$ represents a methyl group and $R^2$ and $R^3$ both represent hydrogen atoms.

7. The compound of claim 1, wherein $R^1$ and $R^2$ both represent hydrogen atoms and $R^3$ and $R^4$ both represent methyl groups.

8. The compound of claim 1, wherein $R^1$, $R^3$ and $R^4$ all represent methyl groups and $R^2$ represents a hydrogen atom.

9. The compound of claim 1, wherein Ar represents a phenyl group substituted by $R^5$, $R^6$ and $R^7$, where $R^5$, $R^6$ and $R^7$ are independently selected from the group consisting of hydrogen atoms, halogen atoms and halogenated alkyl groups having from 1 to 4 carbon atoms.

10. The compound of claim 1, wherein Ar represents a phenyl group substituted by $R^5$, $R^6$ and $R^7$, where $R^5$, $R^6$ and $R^7$ are independently selected from the group consisting of hydrogen atoms and halogen atoms.

11. The compound of claim 10, wherein $R^5$, $R^6$ and $R^7$ are independently selected from the group consisting of hydrogen, chlorine, fluorine or bromine atoms.

12. The compound of claim 1, wherein one of $R^5$, $R^6$ and $R^7$ represents a hydrogen atom and the other two are the same or different and each represents a halogen atom or a halogenated alkyl group having from 1 to 4 carbon atoms.

13. The compound of claim 1, wherein one of $R^5$, $R^6$ and $R^7$ represents a hydrogen atom and the other two are the same or different and each represents a halogen atom.

14. The compound of claim 1, wherein one of $R^5$, $R^6$ and $R^7$ represents a hydrogen atom and the other two are the same or different and each represents a chlorine, fluorine or bromine atom.

15. The compound of claim 1, wherein Ar represents a o-chlorophenyl, p-chlorophenyl, p-fluorophenyl, p-bromophenyl, 2,4-difluorophenyl, 2,6-difluorophenyl, 2,4-dichlorophenyl, 2-chloro-4-fluorophenyl, 4-chloro-2-fluorophenyl, 6-chloro-2-fluorophenyl, 4-trifluoromethylphenyl or 4-trifluoromethoxyphenyl group.

16. The compound of claim 1, wherein Ar represents a p-chlorophenyl, p-fluorophenyl, 2,4-difluorophenyl, 2,4-dichlorophenyl, 2-chloro-4-fluorophenyl or 4-chloro-2-fluorophenyl group.

17. The compound of claim 1, wherein one of $R^8$ and $R^9$ represents a hydrogen atom and the other represents a hydrogen atom or an alkyl group having from 1 to 4 carbon atoms.

18. The compound of claim 1, wherein both of $R^8$ and $R^9$ represent hydrogen atoms.

19. The compound of claim 1, wherein:
$R^1$, $R^2$, $R^3$ and $R^4$ are the same or different and each represent a hydrogen atom or an alkyl group containing from 1 to 4 carbon atoms;
Ar represents a phenyl group substituted by $R^5$, $R^6$ and $R^7$, where $R^5$, $R^6$ and $R^7$ are independently selected from the group consisting of hydrogen atoms, halogen atoms and halogenated alkyl groups having from 1 to 4 carbon atoms; and
one of $R^8$ and $R^9$ represents a hydrogen atom and the other represents a hydrogen atom or an alkyl group having from 1 to 4 carbon atoms.

20. The compound of claim 1, wherein:

one of $R^1$ and $R^2$ represents a hydrogen atom and the other represents an alkyl group containing from 1 to 4 carbon atoms;

one of $R^3$ and $R^4$ represents a hydrogen atom or an alkyl group containing from 1 to 4 carbon atoms and the other represents an alkyl group containing from 1 to 4 carbon atoms;

Ar represents a phenyl group substituted by $R^5$, $R^6$ and $R^7$, where $R^5$, $R^6$ and $R^7$ are independently selected from the group consisting of hydrogen atoms, halogen atoms and halogenated alkyl groups having from 1 to 4 carbon atoms; and one of $R^8$ and $R^9$ represents a hydrogen atom and the other represents a hydrogen atom or an alkyl group having from 1 to 4 carbon atoms.

21. The compound of claim 1, wherein:

one of $R^1$ and $R^2$ represents a hydrogen atom and the other represents a methyl or ethyl group;

one of $R^3$ and $R^4$ represents a hydrogen atom or a methyl group and the other represents a methyl group;

Ar represents a phenyl group substituted by $R^5$, $R^6$ and $R^7$, where $R^5$, $R^6$ and $R^7$ are independently selected from the group consisting of hydrogen atoms and halogen atoms; and both of $R^8$ and $R^9$ represent hydrogen atoms.

22. The compound of claim 1, wherein:

$R^1$ and $R^4$ both represent methyl groups and $R^2$ and $R^3$ both represent hydrogen atoms;

Ar represents a o-chlorophenyl, p-chlorophenyl, p-fluorophenyl, p-bromophenyl, 2,4-difluorophenyl, 2,6-difluorophenyl, 2,4-dichlorophenyl, 2-chloro-4-fluorophenyl, 4-chloro-2-fluorophenyl, 6-chloro-2-fluorophenyl, 4-trifluoromethylphenyl or 4-trifluoromethoxyphenyl group; and both of $R^8$ and $R^9$ represent hydrogen atoms.

23. The compound of claim 1, wherein:

$R^1$ and $R^4$ both represent methyl groups and $R^2$ and $R^3$ both represent hydrogen atoms;

Ar represents a p-chlorophenyl, p-fluorophenyl, p-bromophenyl, 2,4-difluorophenyl, 2,4-dichlorophenyl, 2-chloro-4-fluorophenyl or 4-chloro-2-fluorophenyl group; and both of $R^8$ and $R^9$ represent hydrogen atoms.

24. The compound of claim 1, wherein:

$R^1$ represents an ethyl group;

$R^2$ and $R^3$ both represent hydrogen atoms;

$R^4$ represents a methyl group;

Ar represents a p-chlorophenyl, p-fluorophenyl, p-bromophenyl, 2,4-difluorophenyl, 2,4-dichlorophenyl, 2-chloro-4-fluorophenyl or 4-chloro-2-fluorophenyl group; and both of $R^8$ and $R^9$ represent hydrogen atoms.

25. The compound of claim 1, wherein:

$R^1$ and $R^2$ both represent hydrogen atoms;

$R^3$ and $R^4$ both represent methyl groups;

Ar represents a p-chlorophenyl, 2,4-difluorophenyl, 2,4-dichlorophenyl, 2-chloro-4-fluorophenyl or 4-chloro-2-fluorophenyl group; and both of $R^8$ and $R^9$ represent hydrogen atoms.

26. The compound of claim 1, wherein:

$R^1$, $R^3$ and $R^4$ all represent methyl groups;

$R^2$ represents a hydrogen atom;

Ar represents a p-chlorophenyl, p-fluorophenyl, p-bromophenyl, 2,4-difluorophenyl, 2,4-dichlorophenyl, 2-chloro-4-fluorophenyl or 4-chloro-2-fluorophenyl group; and both of $R^8$ and $R^9$ represent hydrogen atoms.

27. The compound of claim 1, selected from the group consisting of 2-(2,4-difluorophenyl)-3,4-dimethyl-2-[(1H-1,2,4-triazol-1-yl)methyl]oxetane and salts thereof.

28. The compound of claim 1, selected from the group consisting of 2-(4-chlorophenyl)-3,4-dimethyl-2-[(1H-1,2,4-triazol-1-yl) methyl]oxetane and salts thereof.

29. The compound of claim 1, selected from the group consisting of 2-(4-fluorophenyl)-3,4-dimethyl-2-[(1H-1,2,4-triazol-1-yl) methyl]oxetane and salts thereof.

30. The compound of claim 1, selected from the group consisting of 4-ethyl-2-(4-fluorophenyl)-3-methyl-2-[(1H-1,2,4-triazol-1-yl) methyl]oxetane and salts thereof.

31. The compound of claim 1, selected from the group consisting of (2R*,3S*,4R*)-2-(2,4-difluorophenyl)-3,4-dimethyl -2-[(1H-1,2,4-triazol-1-yl)methyl]oxetane and salts thereof.

32. The compound of claim 1, selected from the group consisting of (2R*,3S*,4R*)-2-(4-chlorophenyl)-3,4-dimethyl-2-[(1H-1,2,4-triazol-1-yl)methyl]oxetane and salts thereof.

33. The compound of claim 1, selected from the group consisting of (2R*,3S*,4R*)-2-(4-fluorophenyl)-3,4-dimethyl-2-[(1H-1,2,4-triazol-1-yl)methyl]oxetane and salts thereof.

34. The compound of claim 1, selected from the group consisting of (2R*,3S*,4S*)-4-ethyl-2-(4-fluorophenyl)-3-methyl-2-[(1H-1,2,4-triazol-1-yl)methyl]oxetane and salts thereof.

35. A pharmaceutical composition for the prevention or treatment of fungal infections, which comprises a fungicidally or fungistatically effective amount of an anti-fungal agent, wherein the anti-fungal agent is selected from the group consisting of compounds of formula (I) and pharmaceutically acceptable salts thereof, as defined in claim 1.

36. The composition of claim 35, in which said anti-fungal agent is selected from the group consisting of:

2-(2,4-difluorophenyl)-3,4-dimethyl-2-[(1H-1,2,4-triazol-1-yl)methyl]oxetane;

2-(4-chlorophenyl)-3,4-dimethyl-2-[(1H-1,2,4-triazol-1-yl)methyl]oxetane;

2-(4-fluorophenyl)-3,4-dimethyl-2-[[1H-1,2,4-triazol-1-yl)methyl]oxetane;

4-ethyl-2-(4-fluorophenyl)-3-methyl-2-[(1H-1,2,4-triazol-1-yl)methyl]oxetane;

and pharmaceutically acceptable salts thereof.

37. The composition of claim 35, in which said anti-fungal agent is selected from the group consisting of:

(2R*,3S*,4R*)-2-(2,4-difluorophenyl)-3,4-dimethyl-2-[(1H-1,2,4-triazole-1-yl)methyl]oxetane;

(2R*,3S*,4R*)-2-(4-chlorophenyl)-3,4-dimethyl-2-[(1H-1,2,4-triazol-1-yl)methyl]oxetane;

(2R*, 3S*,4R*)-2-(4-fluorophenyl)-3,4-dimethyl-2-[(1H-1,2,4-triazol-1-yl)methyl]oxetane;

(2R*, 3S*,4S*)-4-ethyl-2-(4-fluorophenyl)-3-methyl-2-[(1H-1,2,4-triazol-1-yl)methyl]oxetane;

and pharmaceutically acceptable salts thereof.

38. A method for the prevention or treatment of fungal infections, which comprises applying or administering a fungicidally or fungistatically effective amount of an anti-fungal agent to an animal, wherein the anti-fungal agent is selected from the group consisting of compounds of formula (I) and pharmaceutically acceptable salts thereof, as defined in claim 1.

39. The method of claim 38, in which said anti-fungal agent is selected from the group consisting of:
2-(2,4-difluorophenyl)-3,4-dimethyl-2-[(1H-1,2,4-triazo-1--yl)methyl]oxetane;
2-(4-chlorophenyl)-3,4-dimethyl-2-[(1H-1,2,4-triazol-1-yl)methyl]oxetane;
2-(4-fluorophenyl)-3,4-dimethyl-2-[(1H-1,2,4-triazol-1-yl)methyl]oxetane;
4-ethyl-2-(4-fluorophenyl)-3-methyl-2-[(1H-1,2,4-triazol-1-yl)methyl]oxetane;
and pharmaceutically acceptable salts thereof.

40. The method of claim 38, in which said anti-fungal agent is selected from the group consisting of:
(2R*,3S*,4R*)-2-(2,4-difluorophenyl)-3,4-dimethyl-2-(1H-1,2,4-triazol-1-yl)methyl]oxetane;
(2R*,3S*,4R*)-2-(4-chlorophenyl)-3,4-dimethyl-2-[(1H-1,2,4-triazol-1-yl)methyl]oxetane;
(2R*,3S*,4R*)-2-(4-fluorophenyl)-3,4-dimethyl-2-[(1H-1,2,4-triazol-1-yl)methyl]oxetane;
(2R*,3S*,4S*)-4-ethyl-2-(4-fluorophenyl)-3-methyl-2-[(1H-1,2,4-triazol-1-yl)methyl]oxetane;
and pharmaceutically acceptable salts thereof.

41. An agricultural composition for the protection of plants and plant reproductive matter from fungal attack, which composition comprises a fungicidally or fungistatically effective amount of a compound of formula (I) or a salt thereof, as defined in claim 1, in admixture with an agricultural carrier or diluent.

42. The composition of claim 41, in which said anti-fungal agent is selected from the group consisting of:
2-(2,4-difluorophenyl)-3,4-dimethyl-2-[(1H-1,2,4-triazol-1-yl)methyl]oxetane;
2-(4-chlorophenyl)-3,4-dimethyl-2-[(1H-1,2,4-triazol-1-yl)methyl]oxetane;
2-(4-fluorophenyl)-3,4-dimethyl-2-[(1H-1,2,4-triazol-1-yl)methyl]oxetane;
4-ethyl-2-(4-fluorophenyl)-3-methyl-2-[(1H-1,2,4-triazol-1-yl)methyl]oxetane;
and salts thereof.

43. The composition of claim 41, in which said anti-fungal agent is selected from the group consisting of:
(2R*,3S*,4R*)-2-(2,4-difluorophenyl)-3,4-dimethyl-2-[(1H-1,2,4-triazol-1-yl)methyl]oxetane;
(2R*,3S*,4R*)-2-(4-chlorophenyl)-3,4-dimethyl-2-[(1H-1,2,4-triazol-1-yl)methyl]oxetane;
(2R*,3S*,4R*)-2-(4-fluorophenyl)-3,4-dimethyl-2-[(1H-1,2,4-triazol-1-yl)methyl]oxetane;
(2R*,3S*,4S*)-4-ethyl-2-(4-fluorophenyl)-3-methyl-2-[(1H-1,2,4-triazol-1-yl)methyl]oxetane;
and salts thereof.

44. A method of protecting plants and plant reproductive matter from fungal attack, which method comprises applying to said plants or plant reproductive matter or to a locus including the same a fungicidally or fungistatically effective amount of a compound of formula (I) or a salt thereof, as defined in claim 1.

45. The method of claim 44, in which said anti-fungal agent is selected from the group consisting of:
2-(2,4-difluorophenyl)-3,4-dimethyl-2-[(1H-1,2,4-triazol-1-yl)methyl]oxetane;
2-(4-chlorophenyl)-3,4-dimethyl-2-[(1H-1,2,4-triazol-1-yl)methyl]oxetane;
2-(4-fluorophenyl)-3,4-dimethyl-2-[(1H-1,2,4-triazol-1-yl)methyl]oxetane;
4-ethyl-2-(4-fluorophenyl)-3-methyl-2-[(1H-1,2,4-triazol-1-yl)methyl]oxetane;
and salts thereof.

46. The method of claim 44, in which said anti-fungal agent is selected from the group consisting of:
(2R*,3S*,4R*)-2-(2,4-difluorophenyl)-3,4-dimethyl-2-[(1H-1,2,4-triazol-1-yl)methyl]oxetane;
(2R*,3S*,4R*)-2-(4-chlorophenyl)-3,4-dimethyl-2-[(1H-1,2,4-triazol-1-yl)methyl]oxetane;
(2R*,3S*,4R*)-2-(4-fluorophenyl)-3,4-dimethyl-2-[(1H-1,2,4-triazol-1-yl)methyl]oxetane;
(2R*,3S*,4S*)-4-ethyl-2-(4-fluorophenyl)-3-methyl-2-[(1H-1,2,4-triazol-1-yl)methyl]oxetane;
and salts thereof.

* * * * *

UNITED STATES PATENT AND TRADEMARK OFFICE
CERTIFICATE OF CORRECTION

PATENT NO. : 5,134,152
DATED : July 28, 1992
INVENTOR(S) : TAKESHIBA et al

It is certified that error appears in the above-identified patent and that said Letters Patent is hereby corrected as shown below:

Title page, insert the following Priority Data:

--[30] Foreign Application Priority Data

Dec. 7, 1989   [JP]   Japan ..... 1-318545--.

Column 3, line 26, delete "r," and insert --or,--.

Signed and Sealed this

Thirtieth Day of August, 1994

Attest:

BRUCE LEHMAN

*Attesting Officer*    *Commissioner of Patents and Trademarks*